US008142630B2

(12) United States Patent
Strand et al.

(10) Patent No.: US 8,142,630 B2
(45) Date of Patent: Mar. 27, 2012

(54) ELECTROPHORESIS DEVICES AND METHODS FOR FOCUSING CHARGED ANALYTES

(75) Inventors: David Strand, Sherborn, MA (US); Dan M. Leatzow, Kalispell, MT (US); Cornelius F. Ivory, Pullman, WA (US)

(73) Assignees: Protasis Corporation, Marlborough, MA (US); Washington State University, Pullman, WA (US)

( * ) Notice: Subject to any disclaimer, the term of this patent is extended or adjusted under 35 U.S.C. 154(b) by 1099 days.

(21) Appl. No.: 10/557,582

(22) PCT Filed: May 19, 2004

(86) PCT No.: PCT/US2004/015935
§ 371 (c)(1),
(2), (4) Date: Dec. 19, 2007

(87) PCT Pub. No.: WO2004/113898
PCT Pub. Date: Dec. 29, 2004

(65) Prior Publication Data
US 2008/0087546 A1    Apr. 17, 2008

Related U.S. Application Data

(60) Provisional application No. 60/471,623, filed on May 19, 2003.

(51) Int. Cl.
*G01N 27/447* (2006.01)
*G01N 27/453* (2006.01)
(52) U.S. Cl. ........ 204/451; 204/601; 204/605; 204/600; 204/450
(58) Field of Classification Search .......... 204/600–605, 204/450–455
See application file for complete search history.

(56) References Cited

U.S. PATENT DOCUMENTS

| | | | |
|---|---|---|---|
| 5,019,232 A | 5/1991 | Wilson et al. | |
| 5,061,361 A * | 10/1991 | Gordon | 204/452 |
| 5,298,143 A | 3/1994 | Ivory et al. | |
| 5,468,365 A | 11/1995 | Menchen et al. | |
| 6,176,991 B1 * | 1/2001 | Nordman | 204/601 |
| 6,186,660 B1 * | 2/2001 | Kopf-Sill et al. | 366/340 |
| 6,277,258 B1 | 8/2001 | Ivory et al. | |
| 6,465,257 B1 | 10/2002 | Parce et al. | |
| 6,991,713 B2 * | 1/2006 | Adourian et al. | 204/453 |
| 7,427,343 B2 * | 9/2008 | Han et al. | 204/600 |
| 2001/0023825 A1 | 9/2001 | Frumin et al. | |
| 2002/0139675 A1 | 10/2002 | Mariella | |
| 2003/0094369 A1 | 5/2003 | Tolley et al. | |

OTHER PUBLICATIONS

International Search Report for PCT/US04/15935, Nov. 16, 2004.

* cited by examiner

*Primary Examiner* — Alex Noguerola
(74) *Attorney, Agent, or Firm* — Banner & Witcoff, Ltd.

(57) ABSTRACT

Devices are provided for separating and focusing charged analytes, comprising a separation chamber and two or more electrodes, for example, an electrode array. A membrane separates the separation chamber and the electrodes. The separation chamber of the device is configured, that is, the separation chamber has a shaped geometry, which serves to induce a gradient in an electric field generated by the electrodes in the electrode chamber. Optionally, molecular sieve is included in the separation chamber that is operative to shift the location at which a stationary focused band of a charged analyte forms under a given set of focusing process parameters. Methods are provided for separating and focusing charged analytes comprising introducing a first fluid comprising at least one charged analyte into the separation chamber of a device as just described, applying an electric field gradient to the charged analyte to focus the charged analyte in the electric field gradient.

21 Claims, 38 Drawing Sheets

Figure 1: Illustration of focusing with a gradient in bulk flow
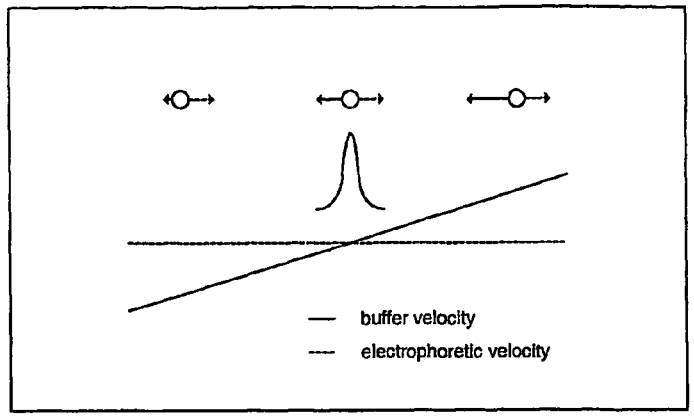
Figure 2: Showing configured sample channel
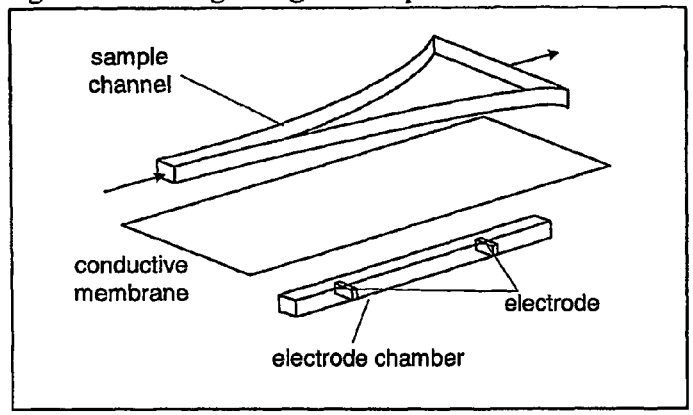
Figure 3: showing configure sample channel
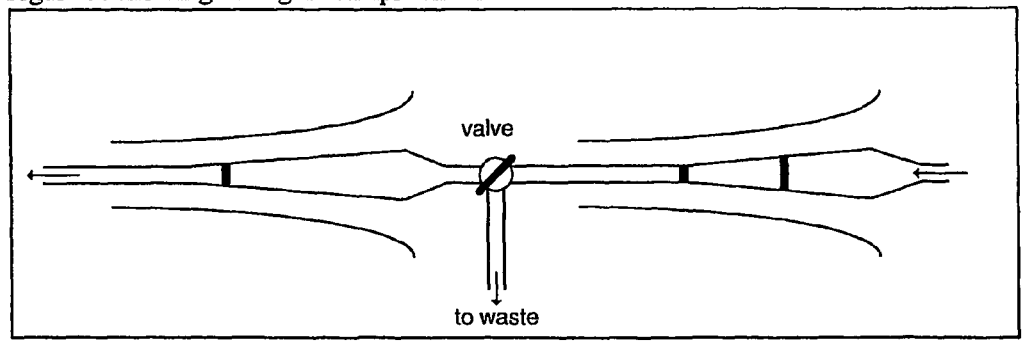

Figure 5: diagram for focusing using a gradient in flow $u_x$: elution velocity of solute    $\mu$ : electrophoretic mobility of solute
$E$ : electric field strength along the column    $\mu E$ : electrophoretic migration velocity of solute

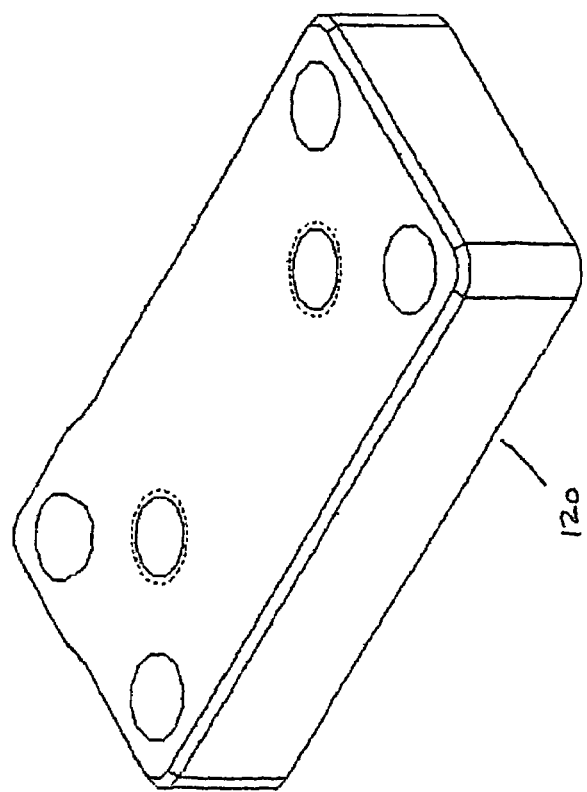
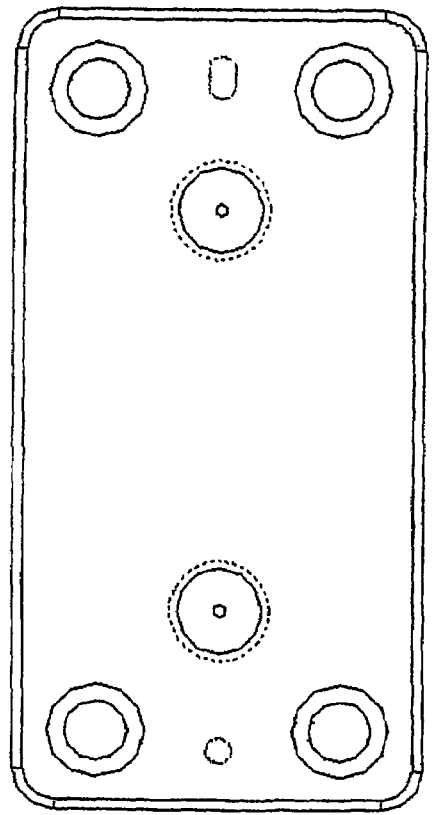

Figure 22B: Configured sample channel
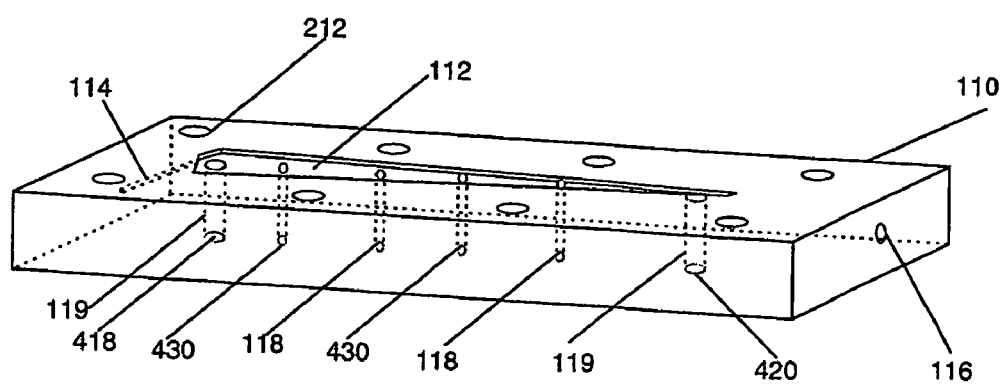

ELECTROPHORESIS DEVICES AND METHODS FOR FOCUSING CHARGED ANALYTES

CROSS-REFERENCE TO RELATED APPLICATIONS

This application is a 35 U.S.C. §371 National Phase filing of PCT Application No. PCT/US04/015935 filed 19 May 2004, which application claimed priority of the following commonly owned U.S. Provisional Patent Application—U.S. Ser. No. 60/471,623, filed 19 May 2003. The PCT application designated the United States and was published in the English language on 29 Dec. 2004 as WO 04/113898 A1.

INTRODUCTION

The present invention is directed to an electrophoretic device, systems incorporating such devices and methods of their use for sample management, for example in the hyphenation of analytical instruments.

BACKGROUND

Electrically driven separations processes for analysis of complex mixtures have become widely accepted throughout the field of biotechnology, and electrophoresis-based devices continue to find widespread use in on-going proteomic investigations. The most prominent technique for proteomic analysis of complex mixtures employs two-dimensional polyacrylamide gel electrophoresis (2D-PAGE), where a complex mixture is loaded onto a gel and resolved along a first axis using isoelectric focusing (i.e., resolving components according to pI) and then along a second axis using SDS-PAGE (i.e., resolving molecules based upon molecular weight). The popularity of electrophoresis stems from the technique's ability to resolve target molecules on the basis of small differences in molecular weight, electrophoretic mobilities, isoelectric points, or combinations of these properties. Although successful, PAGE-based techniques can be time consuming, labor intensive, and do not allow for easy recovery of sample or adjustment of sample loadings to compensate for maldistribution of components commonly observed in biological systems. In addition, integration of 2D-PAGE systems into seamless analytical systems is oftentimes cumbersome.

Chromatographic techniques for analysis of complex mixtures are second only to electrophoresis techniques in terms of resolving power and are more amenable to automation and hyphenation. However, sample concentration issues, flowrate dissimilarities, time-scale differences, or an ability to perform in situ buffer exchange are problematic when integrating LC techniques into hyphenated instrument platforms.

Thus, there is a need for electrically-driven separation devices, systems and methods, suitable for separating and/or concentrating charged analytes, especially for separation and concentration of biomacromolecules, for example, proteins. Accordingly, it is an object of this invention to provide devices, systems and methods for separation and/or concentration of charged analytes.

SUMMARY

In accordance with a first aspect, electrophoretic devices are provided which are capable of separating and focusing one or more charged analytes. The electrophoretic devices comprise a separation chamber having a fluid inlet port and a fluid outlet port, with a flow path from the fluid inlet port to the fluid outlet port defining a fluid flow direction through the separation chamber, and electrodes operative when energized to generate an electric field gradient in the separation chamber, wherein the separation chamber has a non-uniform configuration along at least a portion of the flow path. The non-uniformity of the sample chamber is operative to establish or influence the electric field gradient profile generated by the electrodes. As used here, the term sample chamber and analyte chamber and separation chamber are used interchangeably, although it should be recognized that a sample focusing in accordance with certain exemplary embodiments of the methods and devices disclosed here does not in all cases necessarily involve separation of one analyte from another in a sample fluid.

As used here, a configured or non-uniform separation chamber means a separation chamber having a non-uniform cross-section flow channel. That is, the cross-sectional area, and optionally the shape, of the separation chamber varies significantly along the direction of flow, i.e., varies in a manner which influences the electric field gradient profile sufficiently to usefully impact the location, speed or efficiency of focusing of the target analyte. In this regard, varying cross-sectional area should be understood to mean more significant cross-sectional change than, e.g., the end fairing of typical cylindrical glass lab ware. In operation of such electrophoretic devices in the systems and methods disclosed here, the electrodes generate an electric field into the separation chamber, and the non-uniformity of the separation chamber induces or effectively causes or alters the gradient effect in the electric field (either alone or in combined effect with other features of the device, e.g., the controlled energizing of multiple electrodes of an electrode array). The separation chamber may, for example, be in the form of a non-uniform tube, e.g., a frustro-conical configuration in which cross-sectional area increases or decreases along the direction of sample fluid flow. In certain embodiments further comprising an electrode chamber, the electrophoretic device can have a planar configuration, wherein the membrane between the separation chamber and the electrode chamber is flat or planar and forms a shared wall between the separation chamber and the electrode chamber. The separation chamber in such cases may have a substantially uniform height (height here meaning the direction normal to the plane of the membrane) and a non-uniform or non-constant width (width here meaning the direction perpendicular to the overall direction of sample fluid flow and parallel to the plane of the membrane). In other such embodiments, the separation chamber has a substantially uniform width and a varying or non-uniform height. Other such embodiments employ a separation chamber of non-uniform width and non-uniform height. Other such embodiments employ a separation chamber defined by one or more non-linear or non-flat walls, for example, a wall comprised of a series of faces or facets, some or all having varying dimensions; or wherein the separation chamber has a curved cross-section, such as, for example, a half-circular cross-section, that varies axially, as, for example, a half-cone-shaped chamber. Other suitable configurations will be apparent to those skilled in the art given the benefit of this disclosure. In general, the electrode chamber of the device, if any, optionally is also non-uniform in cross-sectional configuration, e.g., with a configuration the same as or similar to any of the configurations disclosed above for the separation chamber.

The non-uniformly cross-sectioned separation channel are at times herein referred to as "configured." The electrodes generate an electric field which is communicated to or extends into the separation chamber. As noted above, the non-uniformity of the separation chamber induces a gradient in the electric field in the separation chamber. In addition, such non-uniformity of the separation chamber further leads to a gradient in the flow rate or hydrodynamic force of a fluid flowing through the separation chamber. The separation chamber in certain preferred embodiments has a substantially uniform height (height here meaning the direction normal to the plane of the membrane) and a non-uniform or non-constant width (width here meaning the direction perpendicular to the overall direction of flow and parallel to the plane of the membrane). In other preferred embodiments, the separation chamber has a substantially uniform width and a varying or non-uniform height. Still other preferred embodiments employ a separation chamber of non-uniform width and non-uniform height. Other preferred embodiments include a separation chamber defined by one or more non-linear walls, for example, a series of faces or facets, some or all having non-uniform dimensions; or wherein the separation chamber has a curved cross-section, such as, for example, a half-circular cross-section, that varies axially, as, for example, a half-cone-shaped chamber.

In certain preferred embodiments, the electrode chamber has a uniform cross-section flow channel. In other preferred embodiments, the electrode chamber is itself non-uniform, that is, the electrode chamber has a non-uniform cross-section flow channel. The non-uniformity of the electrode chamber will, in combination with the other features of the device, influence the electric field gradient profile in the separation chamber during analyte focusing. The electrode chamber in certain preferred embodiments has a substantially uniform depth (depth here meaning the direction normal to the plane of the membrane) and non-uniform width. In other preferred embodiments, the electrode chamber has a substantially uniform width and a varying or non-uniform depth. Other preferred embodiments include an electrode chamber defined by one or more non-linear walls, for example, a series of faces or facets, some or all having non-uniform dimensions; or wherein the electrode chamber has a curved cross-section, such as, for example, a half-circular cross-section, that varies axially, as, for example, a half-cone-shaped chamber.

In accordance with certain exemplary embodiments, the electric field generated by the electrode(s) may be a constant or linear electric field or may be an electric field gradient of any suitable strength and shape, e.g., parabolic, segmented (i.e., having two or more segments each with a different slope), etc. In certain embodiments of the electrophoretic devices disclosed here, the electrodes may be a pair of electrodes, in which case typically they are located at or near opposite ends of the electrode chamber, or may comprise an array of electrodes (meaning more than two electrodes) spaced along the length of the flow path through the separation chamber. In embodiments comprising an electrode array, the array comprises more than two electrodes, for example, 3 or more electrodes, e.g., about 3 to 50 electrodes or more. The electrodes, typically are arranged uniformly or non-uniformly along the axial length of the first chamber, e.g., the electrodes of the array may be spaced evenly throughout the electrode chamber or can have any suitable spacing selected by a user. It will be within the ability of those skilled in the art, given the benefit of this disclosure, to select a suitable number and spacing of electrodes, chamber shape (for both the separation chamber and the electrode chamber) to achieve the desired electric field shape and strength and the desired degree of control of electric field shape and strength. The electrodes can be microfabricated electrodes, e.g., microfabricated bio-electrodes. The electrodes can be protected electrodes, requiring no membrane between the separation chamber and the electrode chamber or simply positioned in the separation chamber. Each such electrode generally has a protective coating or membrane exclusionary of the target analyte and sufficiently permeable to electric current to establish the desired electric field in the separation chamber, optionally a porous membrane, e.g., an ion-exchange membrane. A via or porous material can be used to release gasses evolved at the electrode during operation. The electrode array preferably includes, or is adapted to be connected to, power and control circuitry configured to individually energize each electrode independently of the others. Thus, in such embodiments each electrode can be energized at a level selected independently of the energizing level of other electrodes in the array in order to achieve a desired electric field gradient profile in the separation chamber, and, optionally, to control and change the profile over time as an analyte is focused in the separation chamber from a sample fluid flowing through the chamber. The shape and/or strength of the gradient, as indicated above, will also be influenced by the non-uniformity of the separation chamber and by any non-uniformity of the electrode chamber. In certain preferred embodiments, the electrode array is operative to generate an electric field gradient profile in the separation chamber, which can be dynamically controlled. In such embodiments, typically, each electrode will optionally be capable of being individually controlled, i.e., energized at a level selected independently of the energization level of other electrodes in the array. In certain aspects, the electrode array is independently operative to generate an electric field gradient profile, that is to say, the electrode array can create a gradient in the electric field, the shape and/or strength of which is then acted upon by the non-uniformity of the separation chamber, the electrode(s), or both. In certain examples, the electrode array is operative to generate an electric field gradient profile in the chamber that can be dynamically controlled. In other examples, the voltages of the electrodes of the electrode array typically are individually monitored and controlled to influence the shape and/or strength of the electric field gradient, with or without adjustment or change during the focusing process. Optionally, for example, the voltage applied to each electrode is controlled by a computer-controlled circuit board or suitable processor or the like in operative connection to a suitable voltage source. In certain examples, the electrode array is used to dynamically control the electric field gradient during migration of one or more analytes, for example, to shift the location of a stationary focused band within the first chamber to bring the band over an optional sampling port located on the first chamber from which the band(s) can be selectively removed.

Certain preferred embodiments, encompassing those described above that comprise either a uniform electrode chamber or a non-uniform electrode chamber, further comprise molecular sieve in the separation chamber. The molecular sieve is operative to shift the location at which a stationary focused band of charged analyte forms in the separation chamber under a given set of focusing parameters. The molecular sieve advantageously enables separation of two or more molecules, for example, two or more proteins or other biomacromolecules, which have the same or similar charge to mass ratios or electrophoretic mobilities but different size. The molecular sieve in certain preferred embodiments comprises a gel, for example an organic or an inorganic gel or a mixture thereof. The molecular sieve may be fixed in the sample chamber or may be soluble. Fixed molecular sieve may occupy any suitable portion of the volume of the separation chamber, preferably substantially the entire volume of the separation chamber. Soluble molecular sieve preferably is incorporated into a fluid sample containing the target analyte to be focused. Materials suitable for use as the molecular sieve in a device as disclosed here are further discussed below and, in general, are operative in conjunction with the other components of the device, for the intended analyte(s), under a suitable set of focusing process parameters, to shift the location at which a charged analyte is focused and held in the focusing chamber as a function of the size or molecular weight of the molecule.

In a method aspect, electrophoretic methods for focusing an analyte are provided. In such methods, a device in accordance with the disclosure above is provided, a first or sample fluid comprising at least one analyte, e.g., a charged analyte or an uncharged or inadequately charged analyte in affiliation with suitable lipids or other charged carrier species (as discussed further below) is introduced into the separation chamber and an electric field gradient is established by energizing at least some of the electrodes of eh device. The electric field gradient opposes the hydrodynamic force gradient applied to the analyte by the flow of the sample fluid through the separation chamber. Typically, the electric field strength increases downstream, i.e., increases with distance of flow through the separation chamber. The opposed forces balance each other at a location along the flow path in the separation chamber and the analyte focuses at that location. The electric field gradient arises at least in part due to the cross-sectional non-uniformity of the separation chamber and resultant nonuniformity of current density throughout the separation chamber. The gradient in the electric field can in certain preferred embodiments be influenced by a nonuniformity in the electrode chamber. In other preferred embodiments, the electric field gradient in the separation chamber is influenced by the pattern selected for energizing the individual electrodes of an electrode array, in which the voltages of the electrodes typically are individually monitored and controlled to influence the shape and/or strength of the gradient in the electric field, with or without adjustment or change during the focusing process. Optionally, for example, the voltage applied to each electrode is controlled by a computer-controlled circuit board or suitable processor or the like in operative connection to a suitable voltage source. In certain preferred embodiments, an electrode array is used to dynamically control the electric field gradient during the focusing process, for example, to shift the location of a stationary focused band within the separation chamber to bring the band over an optional offtake port located on the separation chamber from which the band can be selectively removed. Other preferred embodiments use, in addition to the non-uniform separation chamber, both a non-uniform electrode chamber and a controlled electrode array to influence the shape and strength of the electric field gradient in the separation chamber. The gradient in the hydrodynamic force applied to the analyte arises from the flow of fluid through the non-uniform separation chamber. Certain preferred embodiments of the methods disclosed here simultaneously focus multiple analytes from a fluid sample. Each of the analytes is focused in the chamber at a stable position spatially separated from the focusing location of the other.

In accordance with another method aspect, electrophoretic devices as disclosed above are employed with molecular sieve in the separation chamber for focusing a charged analyte in the separation chamber at a stable position that, for a given set of focusing process parameters (e.g., sample fluid flow rate, composition and/or pH, electric field gradient strength and/or configuration, chamber configuration, etc.) is shifted from the location at which it would focus under the same set of process parameters absent the molecular sieve. In certain preferred embodiments, a fluid sample containing multiple charged analytes of different molecular weights but having the same or similar charge to mass ratio or electrophoretic mobility is caused to flow through the separation chamber with a fixed or soluble molecular sieve, such that hydrodynamic force of the fluid flow is opposed by a gradient in the electric field and by the molecular sieve. It should be understood that reference above and elsewhere herein to a fluid sample can mean a single fluid sample comprising multiple analytes passed one or more times through the separation chamber or a series of two or more fluid samples, each comprising one or more analytes, passed in turn through the chamber.

In accordance with certain preferred embodiments, devices and methods are provided, whereby two or more proteins or other biomacromolecules which have the same or similar charge to mass ratios or electrophoretic mobilities but different size, can be focused from the same fluid sample in the separation chamber of a device as disclosed above. Each such biomacromolecule is concentrated at a location in the channel spatially separated from the locations at which others of the biomacromolecules are focused. In accordance with the principles disclosed above, the focusing locations of the different biomacromolecules are stable during the focusing process, that is, each of such analytes can be held at its respective focusing location in the channel during and after the focusing process.

In accordance with another aspect, a processing system is provided for electrofocusing of target molecules, e.g., proteins, etc., comprising one or more electrophoresis devices as disclosed above. In accordance with certain preferred embodiments, such processing systems comprise automated sample injection, a pump or pump module for generation of the focusing chromatographic flow, a cooling and degassing module, and a separation chamber with associated electrode chamber and conductive membrane.

In accordance with another aspect, methods are provided employing the electrophoresis devices and/or the processing systems disclosed above, for sample collection, sample conditioning, sample fractionation, and/or sequential sample withdrawal or release. Certain especially preferred embodiments are operative to capture a dilute sample peak and to focus to a concentrated band, e.g., to capture proteins with mobilities spanning the range 2.0% 10-5-5% 10-4 cm2/V sec, which encompasses a great percentage of molecules with biological interest. Certain especially preferred embodiments are operative to capture sequential injections of dilute sample peaks with subsequent focusing into a single band, e.g., with a total sample loading up to 50 micrograms of protein in a total volume of 2 μL. Certain especially preferred embodiments are operative to capture multiple bands and selectively release a single focused band.

BRIEF DESCRIPTION OF THE DRAWINGS

FIG. 1 is a graph illustrating the principles of EFGF;

FIG. 2 is an exploded view of an exemplary device;

FIG. 3 is a schematic of a system capable of functioning as a "notch filter;"

FIGS. 11-16 are not used.

FIGS. 22B-22E are schematic perspective views of selected components of the device illustrated in FIG. 22A;

DETAILED DESCRIPTION OF CERTAIN PREFERRED EMBODIMENTS

Figure 4:
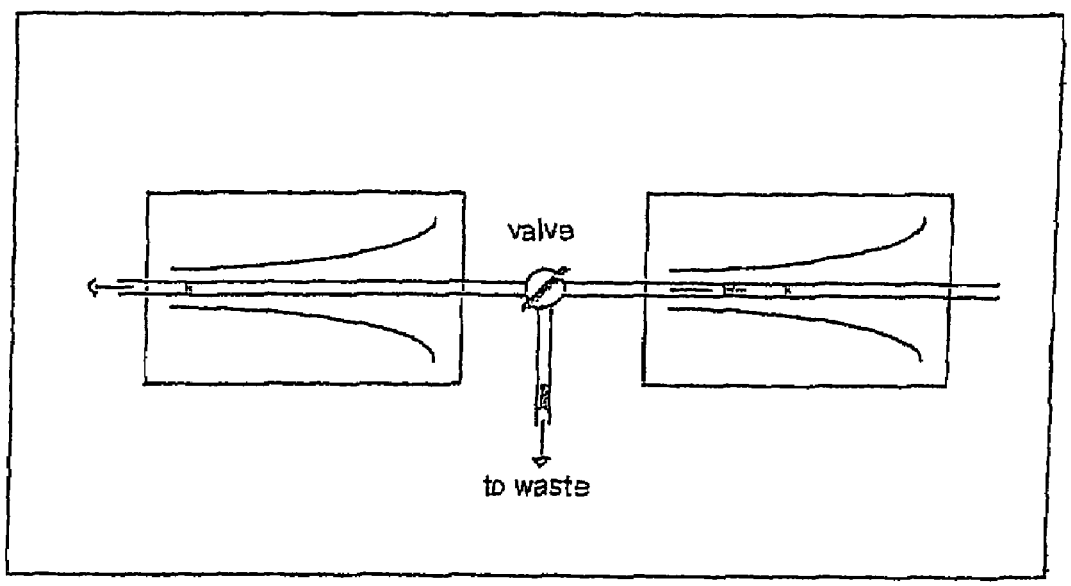
FIG. 4—NOT BEING USED

Unless otherwise indicated or unless otherwise clear from the context in which it is described, aspects or features disclosed by way of example within one or more aspects or preferred embodiments should be understood to be disclosed generally for use with other aspects and embodiments of the devices and methods disclosed herein. It should be understood that the mere usage of the phrase "at least one" or like phrases, in certain instances, is alone not an indication that usages of the individual article "a" in other instances means only one. It should be understood that, as used here and in the appended claims, unless clear otherwise from the context of a particular usage, words such as "a" and "an" and "the" etc. are used in accordance with convention and tradition to mean at least one. Likewise, a device or system or the like that "comprises" a certain feature or element can have one or more than one such feature or element and can also have any other elements or features, etc. Likewise, a device or system comprising two of something can have two or more than two of that thing, a device or system comprising three can have three or more than three, etc.

"Electrophoretic device" as used herein refers to any device which employs opposing hydrodynamic and electrophoretic forces to affect the location of a charged analyte within the device. As used here, the term "focus" and other forms of that word are used generally to mean concentrating and holding a desired analyte (i.e., a target species dissolved or suspended in a sample fluid) in the separation chamber of an electrophoresis device in accordance with the above disclosure. It will be readily understood that this inherently includes separating that analyte from the carrier fluid and optionally from one or more other analytes that do not concentrate at the same location in the channel under the focusing process parameters employed. The term "separating" and other forms of that word, unless otherwise indicated by context or the like, generally are used to describe the result of the present invention, optionally employing molecular sieve in the separation chamber, i.e., separating the desired analyte from the sample fluid and, in certain preferred embodiments, from other analytes. As noted above, the electrode chamber includes electrodes for generating a focusing electric field gradient. The separation chamber is in electrical communication and mass or ionic communication with the electrode chamber through the porous, conductive membrane. In those embodiments described here that comprise a porous membrane, the membrane is at least conductive in that it does not prevent the electric field in the chamber and it is porous in the sense that it is permeable to buffer species or the like without allowing contact of the target analyte with the electrodes. In certain embodiments, the membrane does not substantially affect the electric field generated by the electrodes and does not affect the electric field experienced by the separation chamber. "Communication" or "electrical communication" as used herein refers to the ability of the electric field that is generated by the electrode array to be transferred, or to have an effect, within the separation chamber, and may be by any means which accomplishes this. The porous membrane retains analytes in the separation chamber and is permeable to certain molecules such that the electrode chamber and separation chamber are in communication as noted above. Generally, an eluant is introduced into and flows through the separation chamber containing the charged analyte. The eluant flow is opposed to the direction of electrophoretic migration of the analyte. As noted above, a "configured" chamber refers to a chamber, i.e. a separation chamber or an electrode chamber, that has a non-uniform cross-section flow channel, that is to say, the cross-sectional area of the separation chamber varies axially along the chamber. It will of course be apparent to one skilled in the art that such configuration or non-uniformity occurs within the electric field, that is to say, the electric field generated by the electrodes encompasses a portion of the separation chamber that is configured.

In accordance with a first aspect, electrophoresis devices are provided that are operative to perform electric field gradient focusing (EFGF), employing a counter-balance of chromatographic flow against electromigration to create high resolution, free-solution separation and focusing functionality for a broad range of analytes in buffer systems, including simple buffer systems. Such devices comprise a non-uniform cross-section separation chamber as a focusing chamber and an electrode chamber separated from the separation chamber by a membrane, typically a permeable or porous membrane e.g., a suitably functionalized dialysis membrane, Nafion® or other ion exchange membrane, which in certain preferred embodiments is substantially planar in configuration. Electrodes are positioned proximate the electrode chamber, i.e., in or near the non-uniform electrode chamber such that the electrode chamber is operative to establish an electric field, which is communicated to the separation chamber, where the non-uniformity of the separation chamber establishes a gradient in the electric field as a function of position along the separation chamber. The membrane is effective to pass electrical current and electrolye ions (e.g., tris-phosphate buffer ions), but not the analyte, i.e., not the target molecule of interest being focused or concentrated in the separation chamber. Certain preferred embodiments of the electrophoresis devices disclosed here are operative to capture and concentrate a sample, as well as route (i.e., release) the sample from the chamber, and have applicability to processes in biotechnology, pharmaceutical or other scientific research and development areas as well as industrial production and testing applications. Certain preferred embodiments of the electrophoresis devices disclosed here provide a dynamic platform for preconcentration and routing of target solutes for subsequent analysis, and can serve as a sample preparation tool. Certain preferred embodiments of the electrophoresis devices disclosed here are substantially planar in configuration, the conductive, porous membrane being substantially flat with the sample flow channel above and the electrode chamber below.

The separation chamber is non-uniform axially, that is to say, the cross-section of the separation chamber varies along the axial length of the channel, such that a gradient is established in an electric field that is generated in the separation chamber by the electric field in the electrode chamber. The separation channel in certain preferred embodiments has a substantially uniform height (height here meaning the direction normal to the plane of the membrane) and a non-uniform or non-constant width (width here meaning the direction perpendicular to the overall direction of flow and parallel to the plane of the membrane). In other preferred embodiments, the separation channel has a substantially uniform width and a non-uniform height. In yet other preferred embodiments, the width and the height are both non-linear, and may include side walls and a top wall that are each nonlinear in the same fashion or to differing degrees, multiple facets that are each non-linear to the same or different degrees, or may form a cone-like shape wherein the walls are curved in a direction normal to the axial direction and non-linear in the axial direction. Combinations of these are also possible. As discussed further below, it will be within the ability of those skilled in this technology area, given the benefit of this disclosure, to employ suitable separation channel geometry, sample flow-rate, sample loading, as well as field strength in the electrode chamber to achieve good separation resolution in a short processing or "focusing" time. The electrode chamber in this aspect is preferably a uniform cross-section flow channel or chamber. In other preferred embodiments, the electrode chamber non-uniform and can comprise any of the embodiments described above for the separation chamber.

In certain preferred embodiments, the focused analytes can be eluted from the electrophoretic focusing device through one or more separation ports positioned midway along the separation chamber, typically between the inlet port and the outlet port. Basically, the desired analyte can be focused to a region of the chamber from which the analyte can be eluted through a port. Analytes can be eluted from the separation chamber by electric field, pressure, vacuum, or other motive force.

In operation under suitable focusing process parameters, the channels or chambers of the devices disclosed above typically are filled with liquid sufficiently electrically conductive to establish an electric field gradient in the separation chamber or chamber when the electrodes of the electrode chamber are energized. The porous, conductive membrane between the chambers preferably is operative to establish selective communication between the separation chamber and the electrode chamber, at least sufficiently to provide selective mass transport between the chambers, but prevents the target analyte from passing to the electrode chamber. The chambers typically are elongate and partly or wholly overlying one another in their longitudinal dimension. The electrodes of the electrode chamber are operative to establish an electric field in the electrode chamber, which is communicated through the porous conductive membrane to the separation chamber. A gradient is induced in the electric field by the non-uniformity of the separation chamber, either alone or, where existent, in combination with the non-uniformity of the electrode chamber and/or the electrode array. Additionally, a gradient is induced in the flow rate of a fluid flowing through the separation chamber. The charged analyte focuses at the point at which the electrophoretic force balances with the opposing hydrodynamic force exerted on the analyte.

In operation, the device includes the flow of a first or sample fluid, typically a liquid, through the separation chamber, and the flow of a second or electrode fluid, also typically a liquid, through the second, or electrode chamber. Generally, the first liquid is an electrophoretic eluant (e.g., buffer solution) and the second liquid is a coolant. Suitable liquids include simple liquids such as buffered water, complex fluids, for example mixtures of water and solvent, etc. The first liquid can be the same as or different from the second liquid. During focusing and separation, and depending on the requirements of the particular separation, the composition of either the first and/or the second liquid can be changed to achieve the desired result. As noted above, liquid flow through the separation chamber preferably opposes the direction of electrophoretic migration of the analyte and can be driven by any one of a variety of forces including electric field, pressure, vacuum, or other motive force. In a preferred embodiment, the direction of liquid flow through the separation chamber is opposite that through the electrode chamber.

In accordance with certain preferred embodiments, a fluid gradient can be used to provide increased separation between different bands of analytes. As used here, fluid gradient refers to variation in the composition of the fluid flowing through the separation chamber during the separation of the analytes. For example, in a separation using two solvents, A and B, the separation may begin with 100% solvent A. As the separation progresses, the amount of solvent B can be increased, e.g., linearly, step-wise, logarithmically, etc., such that the solvent compositions introduced into the chamber includes both A and B. Typically, the amount of each solvent in the solvent gradient is controlled by varying the amount of solvent introduced into the chamber. The solvents typically are introduced into the chamber through one or more pumps or other suitable devices. In certain embodiments, it may be necessary to provide a mixing chamber so that the solvent can be mixed prior to introduction of the solvents into the devices described here. In certain embodiments, the solvent gradients are computer controlled to provide high precision for the separations. One skilled in the art, given the benefit of this disclosure, will be able to select suitable solvent gradients for use in the devices and methods disclosed here.

In certain preferred embodiments, a hydrodynamic force is applied to the first fluid by pumping the first fluid through the first chamber. The first fluid typically is a liquid with flow rates ranging, e.g., from 0.1 to 10 µL/min. for analytical applications, and, e.g., from 10 to 200 µL/min. for preparative applications. "Flow rate," as used herein, refers to the initial flow rate, that is, the rate of flow into the separation chamber. It will of course be recognized that the flow rate within the chamber will be influenced by the non-uniformity of the separation chamber and thus be different at different locations within the chamber. The flow rate is chosen to provide the desired separation, in other words so that the hydrodynamic force, when combined with the effect of the molecular sieve in embodiments comprising such, counters the electric field gradient at a position between the weakest and the strongest part of the electric field. In this fashion, the analyte will be retained within the separation chamber. Factors that affect the choice of flow rate include, for example, the viscosity and density of the fluid, strength of the electric field gradient, net charge of the analyte, hydrodynamic radius of the analyte, etc. Suitable flow rates can be readily determined by routine trial and error.

As discussed above, the electrodes in certain preferred embodiments' are separated from the separation chamber by a membrane. Suitable membranes allow an electric field to be generated through the membrane material in the separation chamber while desired analytes, for example, macromolecules such as biomacromolecules, are retained in the separation chamber, that is, are not able to directly contact the electrodes. In certain preferred embodiments, the membrane is conductive to heat but not to bulk fluid flow. The membrane advantageously serves to isolate the electrodes from the separation chamber and optionally to avoid disruption of the laminar flow by gas generation or denaturation of charged analyte by contact with the electrodes. Suitable conductive materials include Nafion, cellulose based membranes, membranes having a MWCO of 100-1000, etc. In certain preferred embodiments, the separation and electrode chambers are separated by the membrane. In such embodiments, the membrane is typically a permeable material. As used herein, a permeable material is one that allows communication through the permeable material while (1) desired analytes, for example macromolecules such as biomacromolecules, are retained in the separation chamber; (2) undesired contaminants can be dialyzed out of the separation chamber; and (3) desired molecules, for example buffer ions, etc., can be dialyzed into the separation chamber. In certain preferred embodiments, the permeable material is conductive to heat and buffer ions but not to bulk fluid flow. The permeable material advantageously serves to isolate the electrodes from the separation chamber to avoid disruption of the laminar flow by gas generation or denaturation of charged analyte by contact with the electrodes. Suitable permeable materials include permeable membranes such as dialysis membranes and ion exchange membranes. Other suitable permeable materials will be readily apparent to those of ordinary skill in the art, given the benefit of the present disclosure.

In accordance with certain preferred embodiments, solvents that are used in the devices and methods disclosed here may be degassed prior to separation of analytes. Without wishing to be bound by any particular scientific theory, it is believed that dissolved gases in the solvents can affect the reproducibility of the flow rates of the solvents. Thus, to achieve constant and reproducible flow rates, it may be necessary to remove at least some of the dissolved gases from any solvents prior to introduction of the solvents into the devices described here. The person of ordinary skill in the art, given the benefit of this disclosure, will be able to select suitable techniques for degassing the solvents including, but not limited to, vacuum filtration of the solvents, e.g., filtration through a fritted funnel, bubbling of inert gases, such as, for example, argon and nitrogen, through the solvents, and the like.

In accordance with certain preferred embodiments, a solvent gradient may be used to provide increased separation between different bands of analytes. As used here, solvent gradient refers to variation in the composition of the solvent during the separation of the analytes. For example, in a separation using two solvents, A and B, the separation may begin with 100% solvent A. As the separation progresses, the amount of solvent B can be increased, e.g., linearly, stepwise, logarithmically, etc., such that the solvent composition introduced into the chamber includes a mixture of both solvents A and B. Typically, the amount of each solvent in the solvent gradient is controlled by varying the amount of solvent introduced into the chamber. The solvents typically are introduced into the chamber through one or more pumps or other suitable devices. In certain embodiments, it may be necessary to provide a mixing chamber so that the solvents can be mixed prior to introduction of the solvents into the devices described here. In certain embodiments, the solvent gradients are computer controlled to provide high precision for the separations. One skilled in the art, given the benefit of this disclosure, will be able to select suitable solvent gradients for use in the devices and methods disclosed here.

In accordance with certain preferred embodiments, lipids may be introduced either in the solvent or in the loaded sample. Without wishing to be bound by any particular scientific theory, lipids typically are either hydrophobic, having only nonpolar groups, or can be amphipathic, having both polar and nonpolar groups. In embodiments where one or more analytes are uncharged, it may be necessary to introduce an amphipathic lipid into the sample. Again without wishing to be bound by any particular scientific theory, the nonpolar group of the lipid can associate with one or more uncharged analytes, e.g., through hydrophobic interactions, hydrogen bonding, dipolar interactions, and the like, while the polar group of the lipid typically remains free to provide an overall charge to the lipid-analyte complex. In certain embodiments, lipids are selected from phosphatidic acid, phospholipids and glycerophospholipids such as, for example, phosphatidylcholine, phosphatidylethanolamine, phosphatidylserine, cardiolipin, phosphatidylglycerol, phosphatidylinositol, and the like. In other embodiments, the lipids may include ether glycerophospholipids, cerebrosides, sphingolipids, and the like. One skilled in the art, given the benefit of this disclosure, will be able to select these and other suitable lipids for use in the devices and methods disclosed here.

In accordance with certain embodiments, the lipids can form micelles that may associate with one or more analytes. Without wishing to be bound by any particular scientific theory, because many lipids include a nonpolar group and a polar group, e.g., amphipathic lipids, when the lipids are placed into an aqueous environment, the lipids typically spontaneously associate with each such that the polar groups are positioned outward towards aqueous solvent and the nonpolar groups are positioned inward away from aqueous solvent. Typically, it is necessary to provide the lipids in a sufficient amount, e.g., a critical micelle concentration (CMC), such that micelles can spontaneously form. That is, when the lipids are present at concentration below the CMC, the predominate form is individual free lipids. When the lipids are present at a concentration greater than or equal to the CMC, the predominant form is micelles. Suitable CMC concentrations will be readily selected by those skilled in the art, given the benefit of this disclosure, and the CMC concentration typically depends on the type of lipid selected.

In accordance with certain preferred embodiments, the lipids may form vesicles, e.g., unilamellar (large unilamellar vesicles (LUVs), small unilamellar vesicles (SUVs)) or multilamellar vesicles. Such vesicles are typically characterized as including one or more bilayers formed when the nonpolar groups of the lipids associate with each other. Suitable methods for preparing vesicles will be readily selected by those skilled in the art, given the benefit of this disclosure, and include but are not limited to extrusion, sonication/extrusion, and the like.

In accordance with other preferred embodiments, in the presence of lipids, micelles and/or vesicles, the analytes can partition between the bulk solvent and the lipids, micelles and/or vesicles. For example, one or more portions of the analyte molecule can interact with a portion of the lipid to form an analyte-lipid complex. Typically an equilibrium is established between free analyte and analyte complexed with lipid. It may be possible to favor this equilibrium depending on the nature of the analyte and the nature of the lipid selected. For example, it is possible to favor the lipid-analyte complex by adding lipid in amounts far in excess of the analyte concentration to shift the equilibrium to form additional analyte-lipid complex. When the predominant form in solution is analyte-lipid complex, the position at which the analyte is focused typically will differ from the position at which free analyte will focus. In certain embodiments, lipid-analyte complex will focus at a position substantially less than free analyte, i.e., under similar separation conditions, free analyte typically can migrate further than analyte-lipid complex. One skilled in the art given the benefit of this disclosure will be able to select suitable lipids and suitable amounts of the lipids to favor, or disfavor, lipid-analyte complexes.

In accordance with certain preferred embodiments, lipids, micelles and/or vesicles can be added to a sample to separate analytes of similar molecular weights and/or similar overall charges. Without wishing to by bound by any particular scientific theory, in many instances analytes having similar molecular weights and/or similar overall charges will be difficult to separate from each other and typically will appear as a single band. To facilitate separation of such analytes, lipids, micelles and vesicles can be used. Because there is likely to be some differences between the analytes, e.g., differences in hydrophobicity, composition, three-dimensional structure, surface area properties, and the like, the analytes should interact differently with the lipids, micelles and/or vesicles. For example, if one of the analytes includes a large number of hydrophobic groups, such as amino acids leucine, alanine, valine, etc., then it is possible that these hydrophobic groups will interact more frequently with hydrophobic lipids to reduce entropically disfavored interactions with polar bulk solvent. Accordingly, the use of lipids, micelles and/or vesicles can provide for the ability to baseline separate two or more analytes that behave similarly in the devices provided here.

In accordance with other preferred embodiments, the lipids, micelles and/or vesicles can be used to focus an analyte in a different position than in the absence of any lipids, vesicles or micelles. This result may be desirable for low molecular weight analytes or highly charged analytes, for example, which are difficult to focus at or near a sampling port. For example, without wishing to be bound by any particular scientific theory, it may be difficult to prevent certain analytes from migrating out of the device due to small size, high charge, etc. In the presence of lipids, micelles and vesicles, the analyte-lipid complex can increase the effective size of the analyte, which can reduce its rate of migration in the devices disclosed here. After removal of the analyte-lipid complex, e.g., through an exit port or a sampling port, the analyte-lipid complex can be dissociated and the analyte can be isolated using methods routinely used by the person of ordinary skill in the art, e.g., centrifugation, dialysis, etc. It will be within the ability of the person of ordinary skill in the art, given the benefit of this disclosure, to select and use suitable lipids, micelles and vesicles, and suitable amounts of these compounds, to control migration of one or more analytes in the devices disclosed here.

In accordance with yet other preferred embodiments, the lipids, micelles and/or vesicles can be used to separate two or more analytes having very similar migration behavior, e.g. two or more analytes that focus at the same position within the chamber. This result may be desirable for samples comprising two or more analytes that are similarly charged, for example, and difficult to separate from each other. For example, without wishing to be bound by any particular scientific theory, it may be difficult to separate analytes having similar charges even if those analytes have different physical or physicochemical properties, e.g., different hydrophobicities, secondary or tertiary structures, etc. In the presence of lipids, micelles and vesicles, the analyte-lipid complex can increase the effective size of the analyte, which, in certain embodiments, can reduce its rate of migration in the devices disclosed here. Because different analytes may interact differently with the lipids, due to the differences in the physical properties of the analytes, for example, it may be possible to favor the lipid-analyte complex for one analyte and favor free analyte for another analyte so that the two analytes may be separated from each other. After removal of the analyte-lipid complex, e.g., through an exit port or a sampling port the analyte-lipid complex can be dissociated and the analyte can be isolated using methods routinely used by the person of ordinary skill in the art, e.g., centrifugation, dialysis, etc. It will be within the ability of the person of ordinary skill in the art, given the benefit of this disclosure, to select and use suitable lipids, micelles and vesicles, and suitable amounts of these compounds, to control migration of one or more analytes in the devices disclosed here.

In certain preferred embodiments, electrophoretic devices and methods are provided for focusing a charged analyte and for simultaneously focusing and separating multiple charged analytes. The device comprises non-uniform separation chamber, in accordance with those described above, comprising an inlet for introducing a first liquid into the separation chamber and an outlet for exiting the first liquid from the separation chamber; an electrode chamber comprising a pair of electrodes and an inlet for introducing a second liquid into the electrode chamber and an outlet for exiting the second liquid from the electrode chamber; permeable material separating the first and second chambers; and optionally molecular sieve in the separation chamber operative to separate bands of charged analyte of similar electrophoretic mobilities and different molecular weights. The method of separating charged analytes comprises introducing a first fluid comprising a plurality of charged analytes into a device such as that just described and applying an electric field gradient and a hydrodynamic force gradient to the charged analyte to focus the charged analyte in the electric field into stationary focused bands of charged analyte, wherein the molecular sieve operates to separate the stationary focused bands of charged analyte of similar electrophoretic mobilities and different molecular weights. It will be understood that the focusing and separation of these devices and methods occur simultaneously. Charged analytes have similar electrophoretic mobilities for the purposes of this aspect if they cannot be separated without the molecular sieve, that is, if they focus at the same location within the separation chamber in the absence of molecular sieve. The molecular weights are different if they are sufficiently different to permit separation by devices and methods disclosed here utilizing molecular sieves. As used here, two analytes are said to concentrate or focus at the same location in the separation chamber, under the processing parameters employed, when they focus at locations wholly or partially overlapping one another or so close as to unduly inhibit isolating one species from the other such as by drawing a first one of the analytes out of the chamber via a main flow exit port or via a selectively opened side port or the like.

A given set of focusing process parameters, as noted above, includes all parameters, both dynamic and non-dynamic, that affect the location of a focused band of charged analyte in the separation chamber, other than the influence of the molecular sieve. With the influence of the molecular sieve, the focusing location is different than it would be in the absence of the molecular sieve. All such parameters are encompassed by the term "focusing process parameters" unless otherwise noted or otherwise clear from context. Such factors include, for example, dynamic factors, or factors that are capable of being changed, such as the particular characteristics such as the shape and strength of the electric field gradient, to the extent it is dynamically controlled, for example, to the extent it is influenced by an electrode array; the composition, concentration and pH of the first fluid; the flow rate of the first fluid; the composition, concentration and pH of the second fluid; the flow rate of the second fluid; and other such dynamic factors. The parameters that make up the focusing process parameters further include nondynamic factors such as the dimensions (i.e. size and shape) of the separation chamber and the electrode chamber; and other such nondynamic factors.

In simultaneous focusing in a separation chamber of multiple charged analytes having the same or similar charge to mass ratios, the composition and amount of molecular sieve is chosen such that the location of the stationary focused band of each such analyte is shifted in the chamber to a different degree. It should be understood, however, that reference here to each of multiple analytes being shifted to a different degree does not exclude the possibility that in any given stationary focused band there may be more than one analyte, that is, there may be analyte mixtures for which the devices and methods disclosed here are operative to establish focuses bands of subsets of the analytes, each subset containing one or more of the analytes. Typically the analytes are separated on the basis of their molecular weights or masses. This is particularly useful for separating analytes that have the same or similar mobilities that would not adequately separate in a traditional EFGF device absent the sieve.

Molecular sieves include any medium or substance, for example suitable organic or inorganic polymer or the like, by which such shifting of the focusing location is achieved. The molecular sieve is selected for its ability to shift the location of the stationary focused band of analyte for simultaneous focusing of multiple charged analytes. Preferably, a molecular sieve is chosen such that the amount to which the stationary focused bands of analyte are shifted for a given set of focusing conditions varies with the size or molecular weight of the analyte. Preferably the degree of shift varies proportionally with the molecular weight of the analyte, for example, such that each stationary focused band of charged analyte is focused at a stable location separate from the other charged analytes. Factors that affect the selection of a particular molecular sieve at a particular concentration include, for example, the size of the molecules to be separated and focused, the pH at which the system is operated, and other such relevant factors that will be apparent to those skilled in the art, given the benefit of this disclosure. In certain preferred embodiments, the molecular sieve comprises a gel, which may be either an organic gel or an inorganic gel or a combination of organic and inorganic gel. The gel may be a fixed gel. A fixed gel optionally may be polymerized within the first chamber, such that it does not substantially flow or move when fluid sample is flowed through the first chamber. Alternatively, the gel may be a soluble gel that is dissolved in the first liquid, such that the gel flows with the first liquid when the first liquid flows through the first chamber. In certain embodiments, the soluble gel is introduced into the chamber and resides there during focusing. As used herein, the term "soluble gel" refers to a gel that is soluble or dissolved in a liquid or fluid, and further refers to gels that form suspensions, emulsions, colloids, and the like. Typically, soluble gels comprise polymers having little or no crosslinking. In certain preferred embodiments, the gel will be comprised of molecules having a molecular weight of between about 2000 and about 100,000. Suitable gels include, for example, linear polyacrylamide, polyvinyl alcohol, methyl cellulose and other derivatized celluloses, and the like. Other suitable molecular sieves include microporous structures composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate, and the like. Those of ordinary skill in the art will be able to select suitable gels and sieves through routine experimentation, utilizing known methods, for example by the methods described in Ackers et al., "Determination of stoichiometry and equilibrium constants for reversibly associating systems by molecular sieve chromatography," *Proc. Nat. Acad. Sci. USA* 53: 342-349 (1965), the entire disclosure of which is hereby incorporated by reference for all purposes. Other suitable sieves will be readily apparent to those of ordinary skill in the art, given the benefit of the present disclosure.

Molecular sieve thus enables simultaneous focusing of multiple charged analytes having the same or substantially similar charge to mass ratios. These can be focused from the same fluid sample in the separation chamber of any of the devices disclosed above. Each such molecule is concentrated at a location in the channel spatially separated from the locations at which others of the biomacromolecules are focused. Without wishing to be bound by theory, the molecular sieve in preferred embodiments can be said to apply a focus position-shifting force on the analyte along the direction of fluid sample flow, where the magnitude of such force for a particular molecular sieve material is generally proportional to the size or molecular weight of a target analyte being focused (or held) in the separation chamber and where the magnitude of such force is not (or not as) related to the charge-to-mass (or charge per unit of molecular weight) of the analyte. Charged analytes in a fluid sample can in this way be retained and focused in the separation chamber at locations spatially separated from each other sufficiently to permit each to be readily drawn off or removed from the chamber with little or none of the other focused analytes. Typically, the charged analytes are separated by the molecular sieve, in conjunction with the other focusing process parameters and conditions, and focused at positions along the length of an elongate separation chamber in the general order of their apparent molecular weights. It will be within the ability of those skilled in the art, given the benefit of this disclosure, in some cases with routine trial and error or similar selection aids, to select materials suitably operative as molecular sieves for the intended target analyte(s) under a given set of process parameters. Accordingly, in certain preferred embodiments of the methods and devices disclosed here, each of multiple analytes having the same or similar charge to mass ratios or electrophoretic mobilities and different molecular weights, can be simultaneously focused from a fluid sample at different, separate locations along the length of an elongate separation chamber. Each such analyte can be held indefinitely at its respective focusing location against the flow of the fluid sample. In accordance with certain preferred embodiments, spaced focusing positions of such target analytes can be moved in the chamber to different, stable, separate locations, by suitable control of one or more of the operative focusing forces, e.g., by adjusting the electric field gradient strength or configuration, or the hydrodynamic force of the sample fluid flow, such as by changing its flow rate, or by changing the characteristics of the molecular sieve.

Certain preferred embodiments of the devices and methods herein are suited for focusing and separating charged analytes. Charged analytes that can be focused include, e.g., charged polymers, carbohydrates, and biological analytes, such as proteins, peptides, oligonucleotides, polynucleotides, hormones, biomarkers, and the like, and mixtures of any of these. In particular, charged analytes that have similar charge to mass ratios, such as DNA, RNA, etc., can be separated and focused on the basis of differences in their respective molecular weights. Absent the presence of the molecular sieve of the current devices and methods, such analytes are difficult to fully separate due to the similar charge to mass ratios.

Materials with little or no net charge can be sorbed into charged carriers, for example micelles and liposomes, and focused and separated with devices in accordance with those disclosed herein. For example, proteins that exhibit little net charge can be sorbed into a charged carrier such that the protein acquires the charge of the charged carrier. In certain preferred embodiments, a detergent, for example sodium dodecyl sulfate (SDS), is used as the charged carrier. Without wishing to be bound to a theory, it is presently believed that the SDS binds strongly to protein molecules and "unfolds" them into semi-rigid rods whose lengths are proportional to the length of the polypeptide chain, and hence approximately proportional to molecular weight. Because of the magnitude of the charge of the bound detergent molecules, the protein complexed with such a detergent takes on a high net charge. Furthermore, the total charge is approximately proportional to molecular weight, as the detergent's charge vastly exceeds the protein's own intrinsic charge. Thus, the charge per unit length of a protein-SDS complex is essentially independent of molecular weight. This feature gives protein-SDS complexes essentially equal electrophoretic mobility in a non-restrictive medium. Separation and focusing is then brought about, by the molecular sieve (acting in conjunction with the other focusing process parameters) on the basis of the molecular weights of the protein-SDS complexes.

As noted above, the electrode chamber may include an electrode array. As used herein, the term "electrode array" refers to a plurality of electrodes, that is, more than two electrodes, arranged so as to generate an electric field gradient in the separation chamber. The electric field generated by the electrode array can be DC, AC, or otherwise modulated in time including asymmetric (out of phase) field modulation. The specific nature of the electrode (i.e., size and shape) is not critical. Suitable electrodes include pin-shaped and staple-shaped electrodes, among others. In one preferred embodiment, the electrode array includes a linear array of electrodes (e.g., 50 electrodes arranged linearly) along an axis parallel to the direction of analyte migration. In addition to arrays having electrodes arranged in line with even spacings from one to the next, suitable arrays also include arrays in which the electrodes are not in line and which are not separated by even spacings. Other configurations of electrodes, including two-dimensional electrode arrays, are also within the scope of the devices and methods. Two-dimensional arrays include arrays having rows and columns of electrodes. The electrode chamber in certain preferred embodiments includes more than one electrode array, for example two electrode arrays on opposite sides of the electrode chamber. Suitable electrode array configurations will be readily apparent to those of ordinary skill in the art, given the benefit of the present disclosure, for example electrode array configurations presented in U.S. Pat. No. 6,277,258, hereby incorporated herein in its entirety for all purposes.

Figure 20:
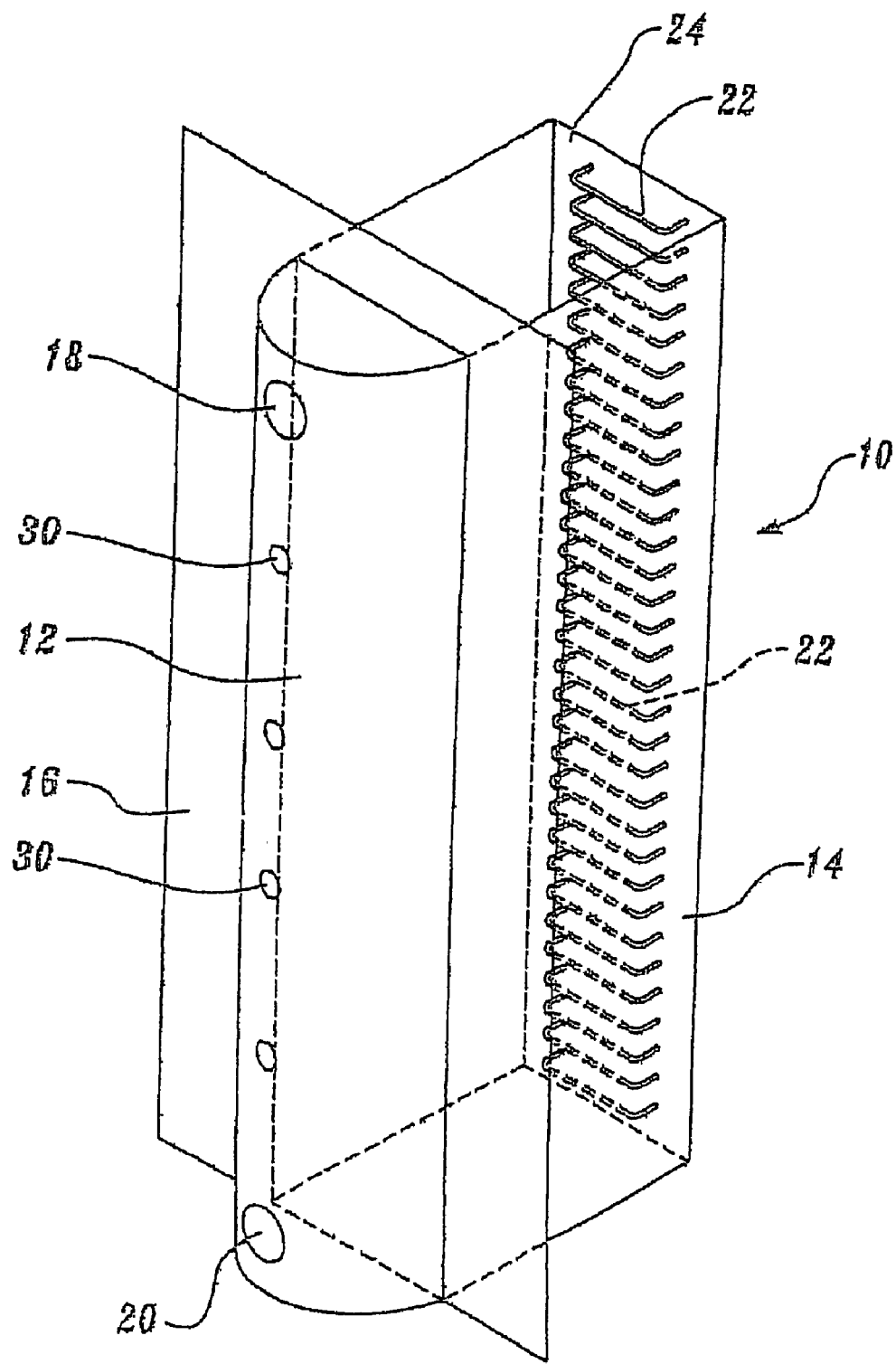
FIG. 20 is a schematic perspective view of a first embodiment of the devices disclosed here.
Figure 21:
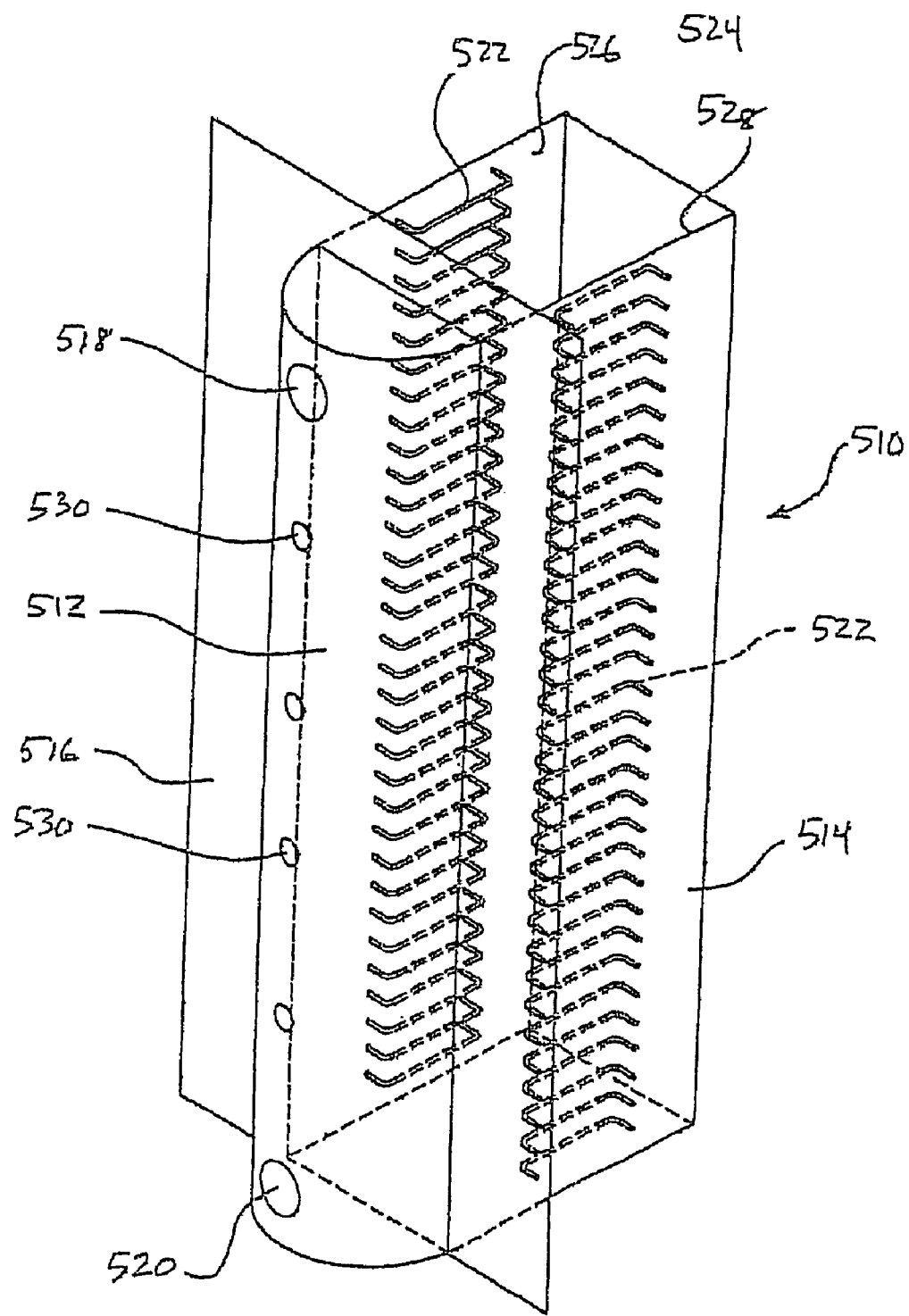
FIG. 21 is a schematic perspective view of another embodiment of the devices disclosed here.
Figure 22A:
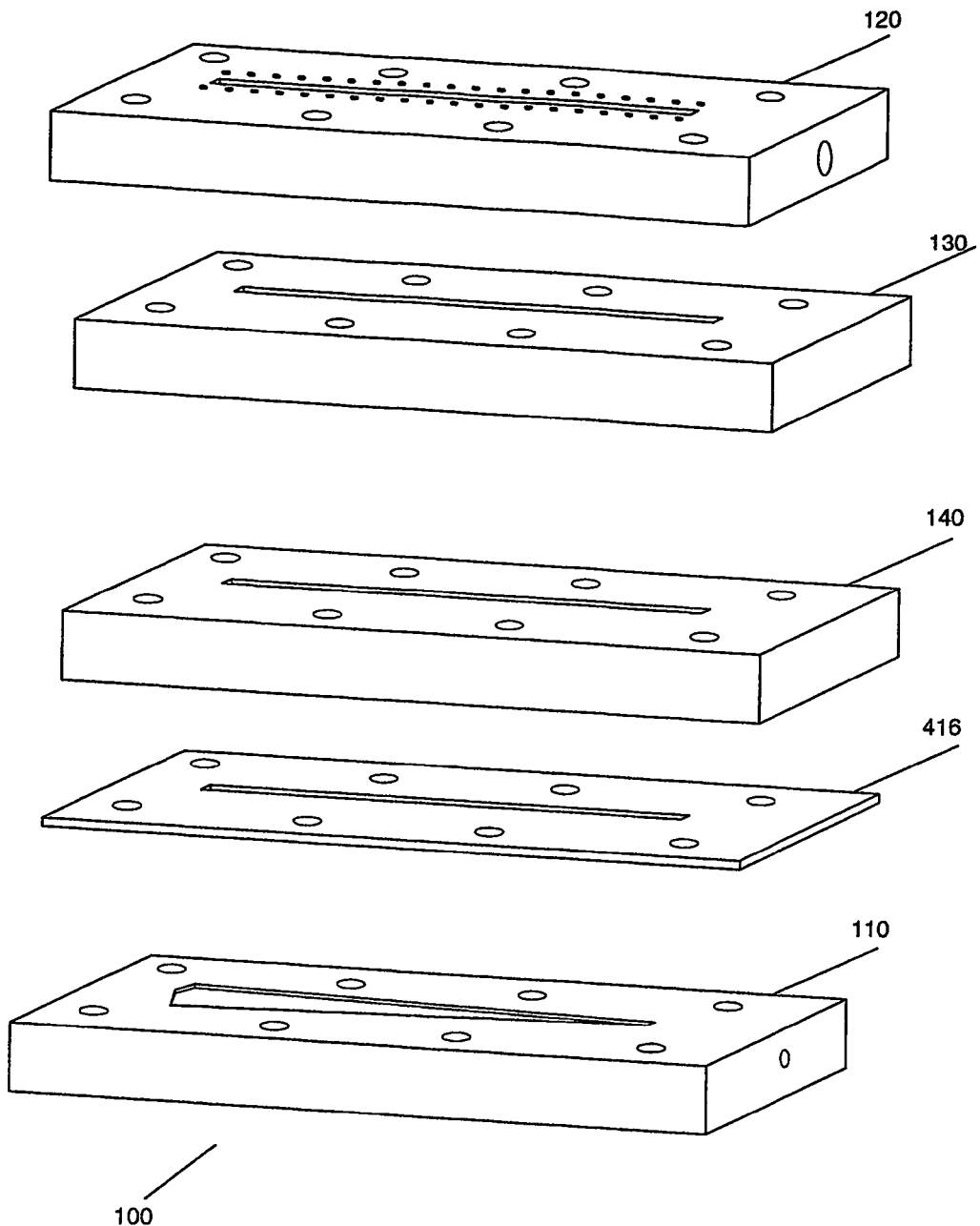
FIG. 22A is an exploded view of another embodiment of the devices disclosed here.
Figure 22C:
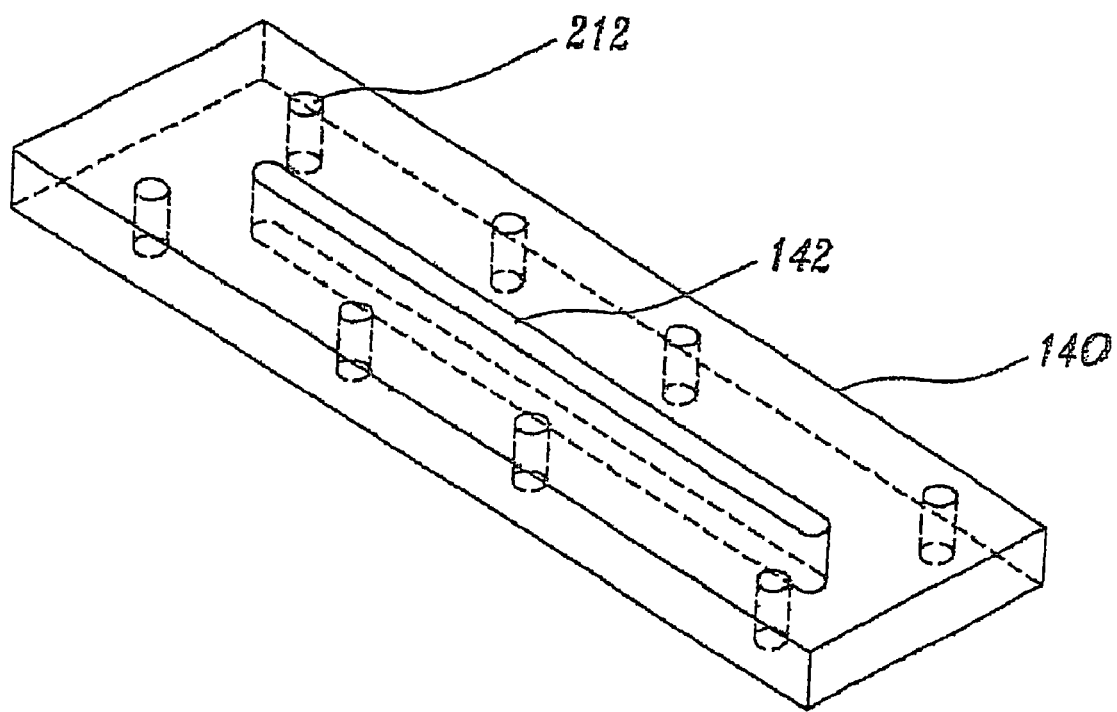
Figure 22D:
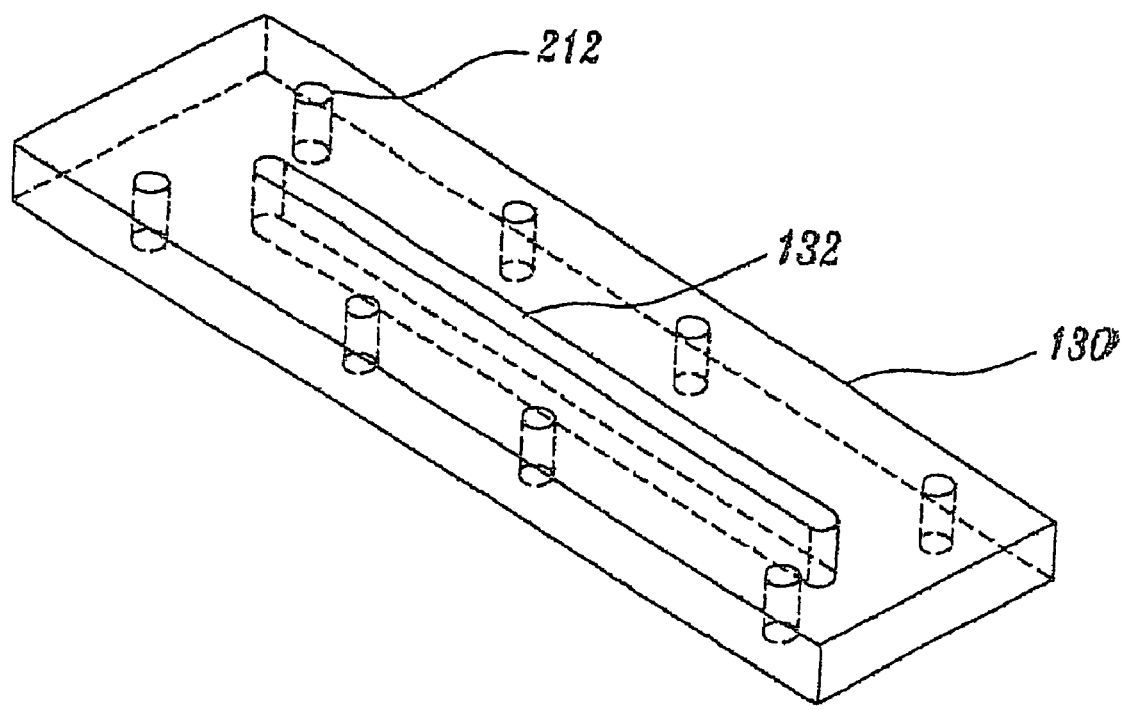
Figure 22E:
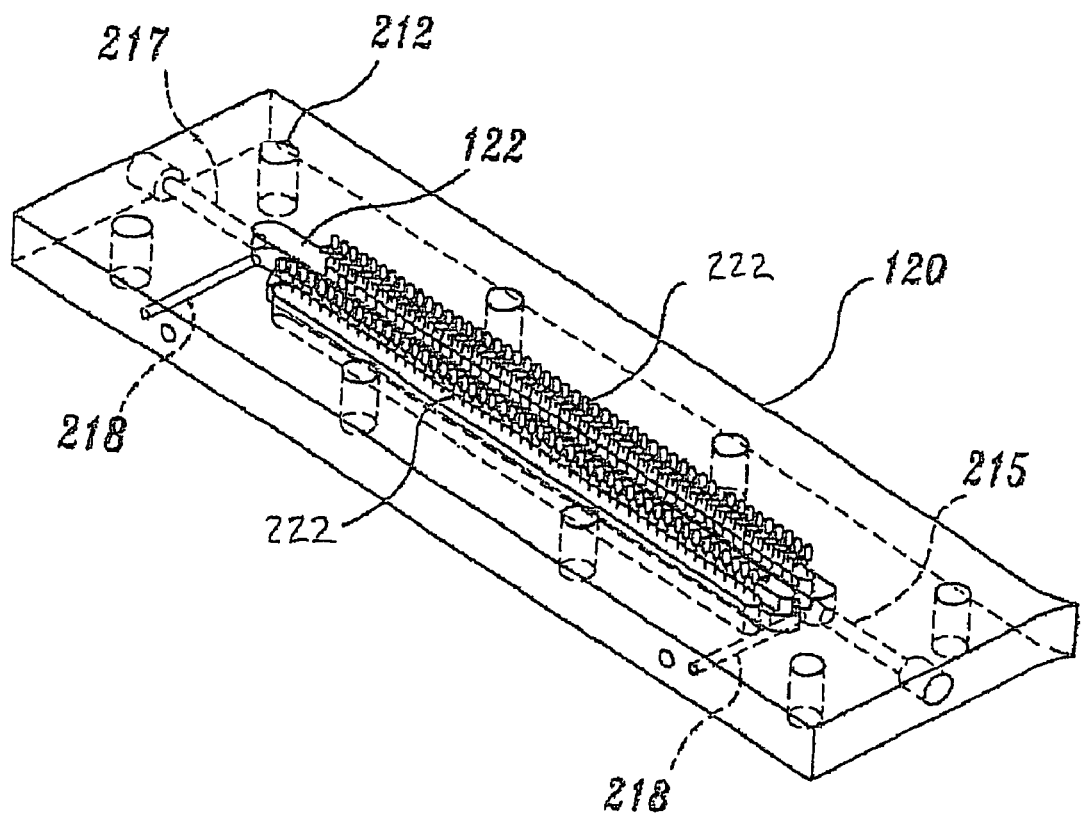

A focusing chamber comprising an electrode array is shown schematically in FIG. 20. Referring to FIG. 20, focusing chamber 10 includes separation chamber 12 and electrode chamber 14 separated by permeable member 16. The separation chamber 12 shown in FIG. 1 is uniform axially; in practice, the electrode chamber would of course be non-uniform axially. Separation chamber 12 includes elution buffer inlet 18 and outlet 20. In operation, in one embodiment, elution buffer flows downward from inlet 18 through chamber 12 exiting outlet 20, and coolant buffer flows through electrode chamber 14, preferably upwardly. Electrode chamber 14 includes an array of electrodes 22. As shown in FIG. 20, the electrode array can be positioned on the electrode chamber surface 24 opposing separation chamber 12 and permeable member 16. The device can further include one or more ports 30 for eluting analytes from the separation chamber. Alternatively, as shown in FIG. 21, the electrode chamber 514, which again is shown for clarity purposes to be uniform axially, includes a pair of electrode arrays 522. Referring to FIG. 21, in this embodiment, the electrode array includes an electrode array positioned on electrode chamber surfaces 526 and 528 adjacent separation chamber 512 and permeable member 516. Device 510 can further include one or more ports 530 for eluting analytes from the separation chamber.

In certain preferred embodiments, each electrode of the array is individually controlled to provide an electric field gradient that can be dynamically controlled (i.e., maintained and adjusted during the course of analyte focusing and/or separation). Techniques involving such dynamic control of the electric field gradient are referred to herein as "Dynamic Field Gradient Focusing" or "DFGF." Control can be manual from the device controller, manually from the device's associated computer, or automatically from the computer once the computer has received feedback from a monitor, such as an optical monitor, for example a video signal, or other suitable monitoring device, following analyte focusing. The controller can sense the electrode's voltage and reset its voltage to its initial setting. Such monitoring allows for computer detection of various peaks, optimization of the separation by locally adjusting the field gradient to tease separated peaks apart, and then pull off those peaks that were selected by the operator either before or during a separation. Suitable configurations of the electrodes, controls, computer equipment and the like will be readily apparent to those of ordinary skill in the art, given the benefit of the present disclosure, for example configurations presented in U.S. Pat. No. 6,277,258, which as noted above is incorporated herein in its entirety for all purposes. The inclusion of an electrode array is particularly advantageous in that the strength and shape of the electric field gradient can be altered during the run, for example, to elute focused bands of analyte off one by one, thus permitting each band to be subject to individual treatment following separation in the device. In accordance with certain preferred embodiments of the device and methods, the electronically generated field can take on arbitrary shapes including exponential profiles, steps, and even locally reversed gradients, for example, to elute proteins. The field shape can be monitored and maintained by computer and modified "on-the-fly" on a point-by-point basis, both spatially and temporally. During a run the operator can optimize the local properties of the field to sharpen an individual band, move a band to an offtake port or set up a moving gradient to elute one or more bands from the separation chamber. With online monitoring, for example optical such as UV/Visible monitoring, or potentiometric monitoring, in place, the operator could be replaced by a computer programmed to detect focused peaks and automatically adjust the field shape to optimize the separation and, when necessary, offload products. Suitable monitoring systems and configurations will be readily apparent to those of ordinary skill in the art, given the benefit of the present disclosure.

Although the above examples illustrate the use of linear electric field gradients, the software can be modified to allow point-by-point adjustment of the field including reversing the field to aid in elution of fractionated bands, isolating and mobilizing a single protein band, or stepping the gradient to improve processing capacity. In addition, because the electronic controller and the technique are largely independent of chamber capacity, there is no reason it cannot be applied at larger or smaller scales.

The dynamic electric field gradient focusing provided by the methods and devices optionally relies in part on field gradient control, which includes hardware and software. Representative gradient control hardware and software are discussed below.

Figure 29:
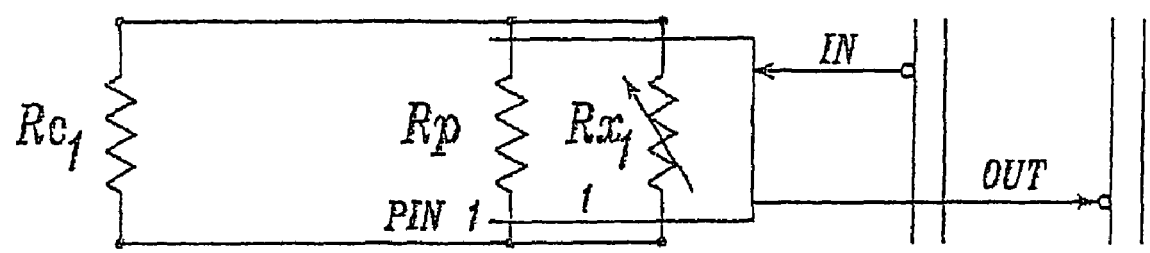
FIG. 29 is a schematic representation of the resistance between two adjacent electrodes in another embodiment of the methods and devices disclosed here.
Figure 30:
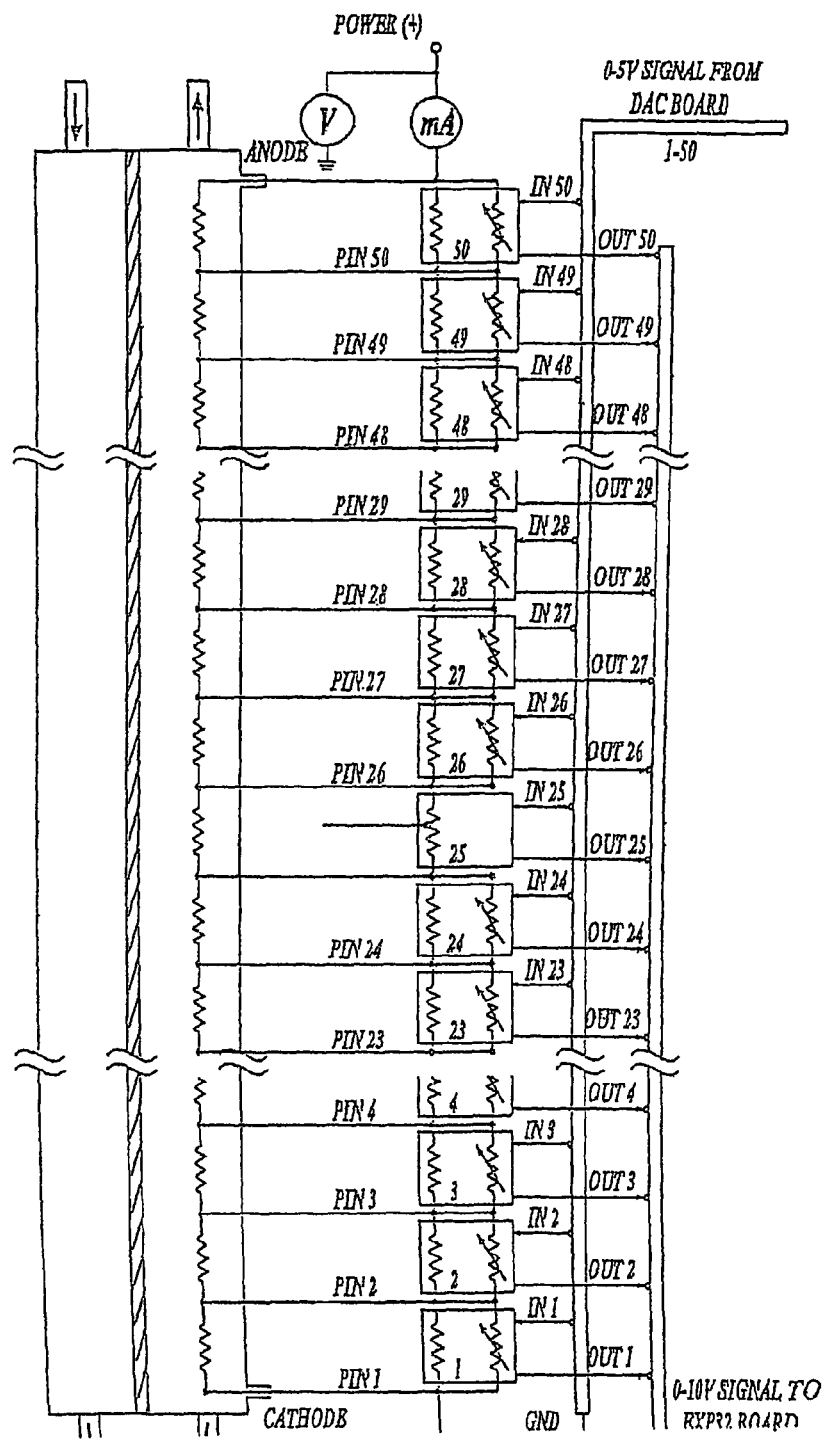
FIG. 30 is a schematic diagram of a representative electric field gradient focusing gradient control model of an embodiment of the methods and devices disclosed here.

The control circuits are designed to manipulate the field gradient by adjusting the effective electrical resistance between each two adjacent electrodes (see FIG. 29). In one embodiment, each pair of electrodes is connected to one of the 50 controller units. A schematic of such an embodiment is shown in FIG. 30, in which the blocks with dash line frames are controller units and each of the controller units handles the data acquisition and the resistance control of two adjacent electrodes.

The electrical resistance between two adjacent electrodes $R_i$ is determined by the sum of the resistance of three parallel resistors, $Rc_i$, $Rp_i$, and $Rx_j$. Note that the buffer between electrodes is considered as a resistor $Rc_i$.

$$R_i = \frac{Rc_i \cdot Rp_i \cdot Rx_i}{Rc_i \cdot Rp_i + Rc_i \cdot Rx_i + Rp_i \cdot Rx_i} \quad (1)$$

The resistors $Rp_i$ are used for protective purpose and have 1 MΩ resistance. Because $R_p \gg Rc_i$, $R_p \gg Rx_1$. Equation (1) can be simplified as $$R_i = \frac{Rc_i \cdot Rx_i}{Rc_i + Rx_i} \quad (2)$$

By changing each $Rx_i$, the circuits adjust each $R_i$ indirectly. By Ohms Law, the potential drop between two electrodes is determined by the resistance between them if the total current going through is constant. The potential drop between the two adjacent electrodes is given by $$V_i = V_{total} \cdot \frac{R_i}{\sum_{i}^{50} R_i} \quad (3)$$

Since the field strength is proportional to the potential drop with the electrodes equally spaced, we can manipulate the field strength point by point by adjusting each $Rx_i$, independently.

$$E_i = \frac{V_i}{d} = \frac{V_{total}}{d} \cdot \frac{R_i}{\sum_{i}^{50} R_i} \quad (4)$$

Where d is the distance between the two adjacent electrodes. An electric field gradient in any shape, linear or non-linear, continuous or stepwise, can be produced with a limitation to the conductivity of the buffer. Note that the resistance between two parallel-connected resistors is always less than any one of them, in other words, $R_i < Rc_i$ must be satisfied. There is more than one group of $R_i$ that satisfies Equation 4, in other words, different groups of $Rx_i$ can be used to establish the same field gradient with the total current going through the chamber arbitrarily. There is no unique equilibrium state. To solve the problem, a small modification to unit No. 25 is made by disabling its control function and replacing $Rp_{25}$ with a 5 kΩ resistor. The total current going through the chamber was fixed, and given by $$I = \frac{V_{25} \cdot Rp_{25} \cdot Rc_{25}}{(Rp_{25} + Rc_{25})} \quad (5)$$

$V_{25}$ has a unique value for a specific field gradient, and can be calculated from the total potential drop across the chamber. $Rc_i$ is determined by the conductivity of the buffer. Therefore, there is a unique value of $Rx_i$ that satisfies Equation 4.

Figure 27:
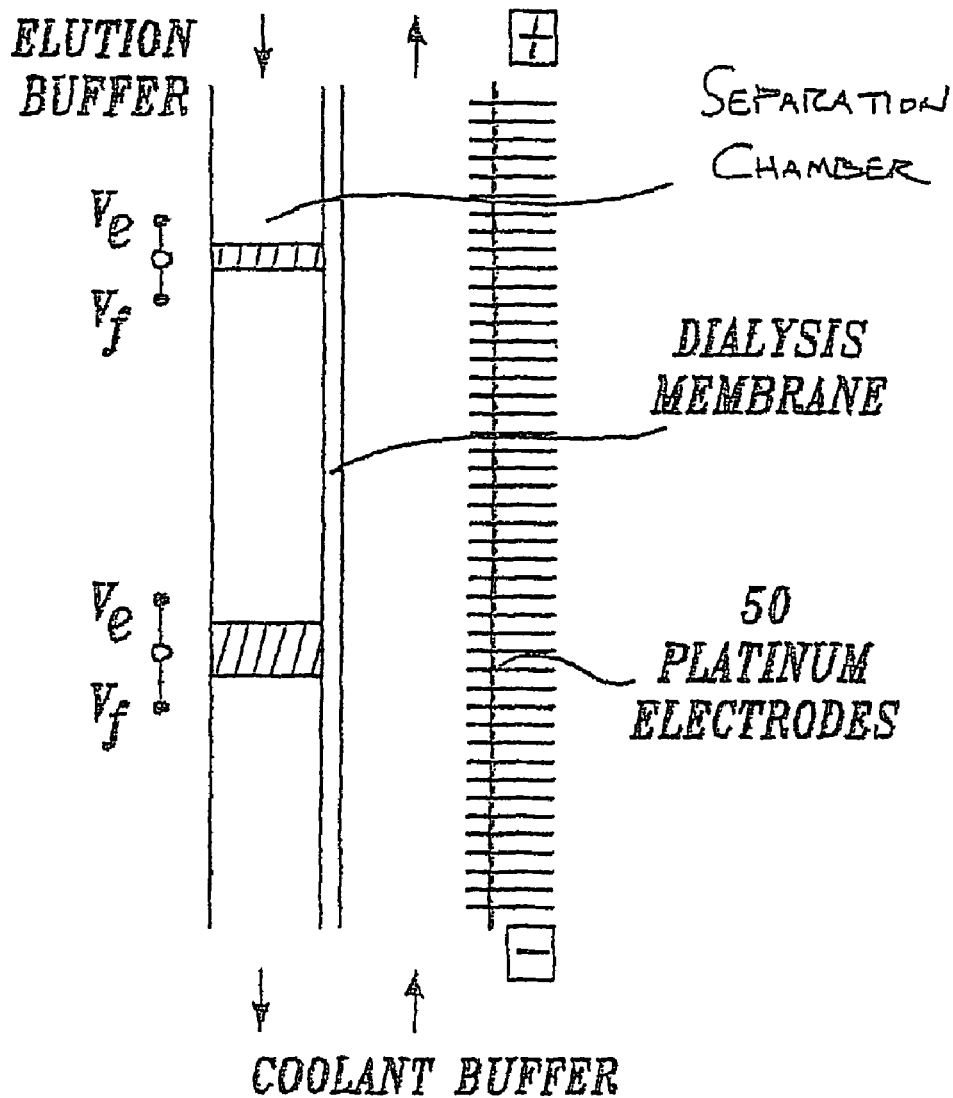
FIG. 27 is a schematic drawing of another embodiment of a device in accordance with the present disclosure.
Figure 28A:
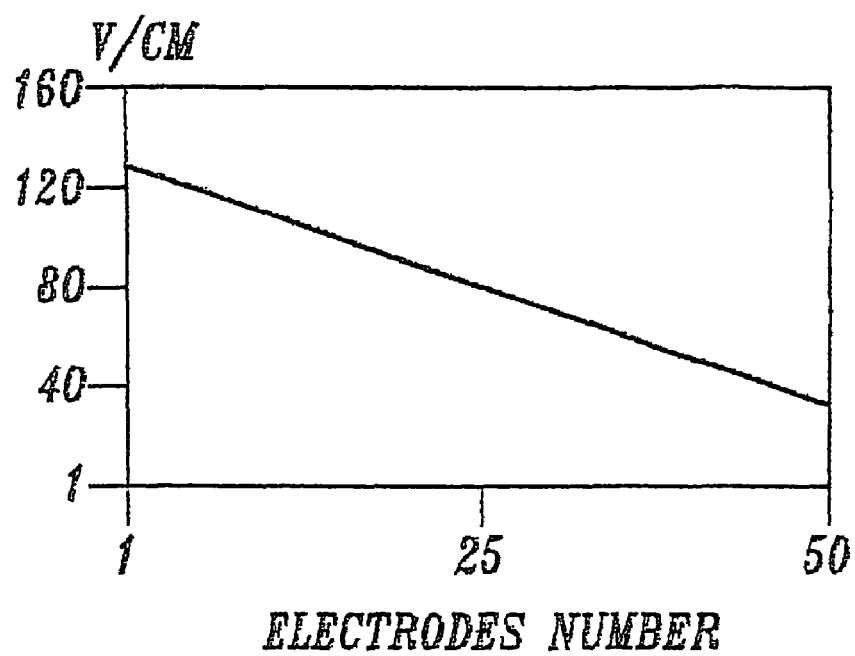
FIGS. 28A and 28B each is a graphical representation of the field strength profile and potential profile, respectively, of a linear field gradient (15.5 v/cm$^2$) in accordance with another embodiment of the methods and devices disclosed here.
Figure 28B:
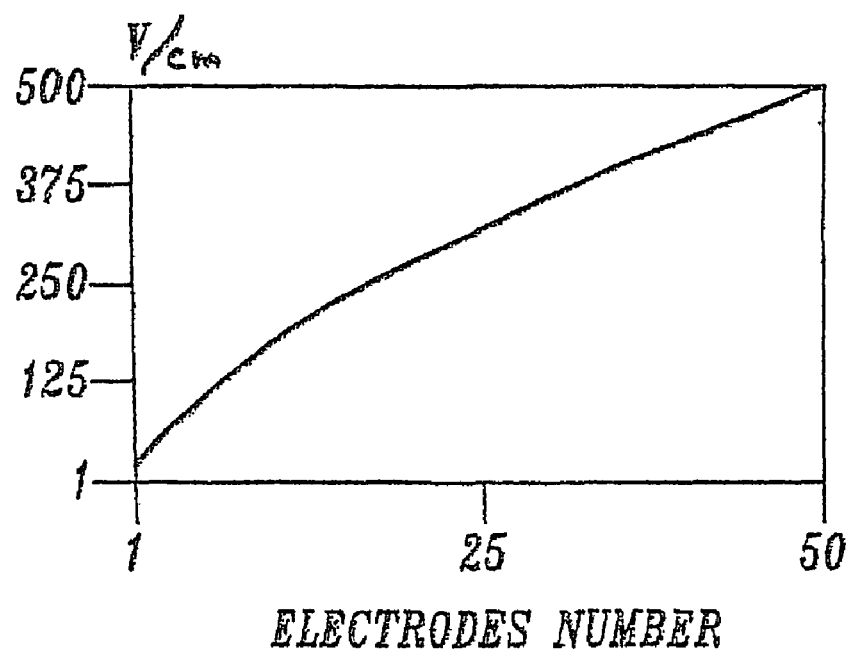

In certain preferred embodiments, dynamic electric field gradients are created by a computer-controlled external circuit, which manipulates the field strength between each pair of adjacent electrodes, as exemplified in FIG. 27. Varying field strength along the separation chamber can thus be achieved. FIGS. 28A and 28B are graphical representations of linear electric field gradients so generated.

Figure 31:
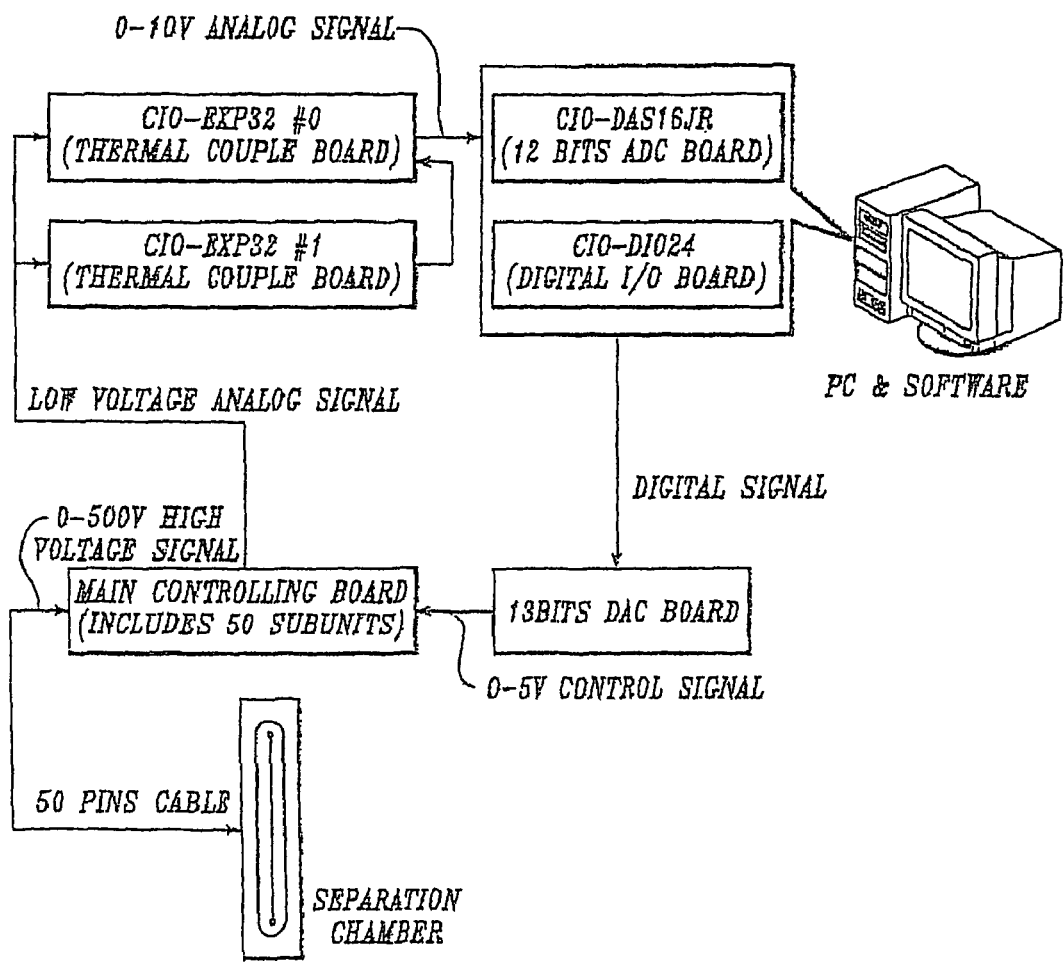
FIG. 31 is a schematic diagram of a representative electric field gradient focusing gradient control circuits.

Representative gradient control circuits are shown schematically in FIG. 31. The blocks represent electronic boards, the lines represent standard ribbon cables. Referring to FIG. 31, the PC monitor/controller board and the 13 bit DAC board were built in our laboratory. Some modifications have been made for better performance. The data channels between the two CIO-EXP32 boards and the CIO-DAS16Jr boards are programmed rather than being physically connected. CIO-DAS16Jr and CIO-DIO24 are plugged into extension slots of the PC. The two thermocouple boards CIO-EXP32, the 16-channel ADC board CIO-DAS16/Jr and the 24-channel Digital I/O board CIO-DIO24 were purchased from ComputerBoards, Inc. Standard SCSI ribbon cables are used to connect all the boards. There are 50 controller units plugged into the mother board. Each unit corresponds to one pair of electrodes. The whole system was grounded to protect the circuits from unexpected shock.

Figure 32:
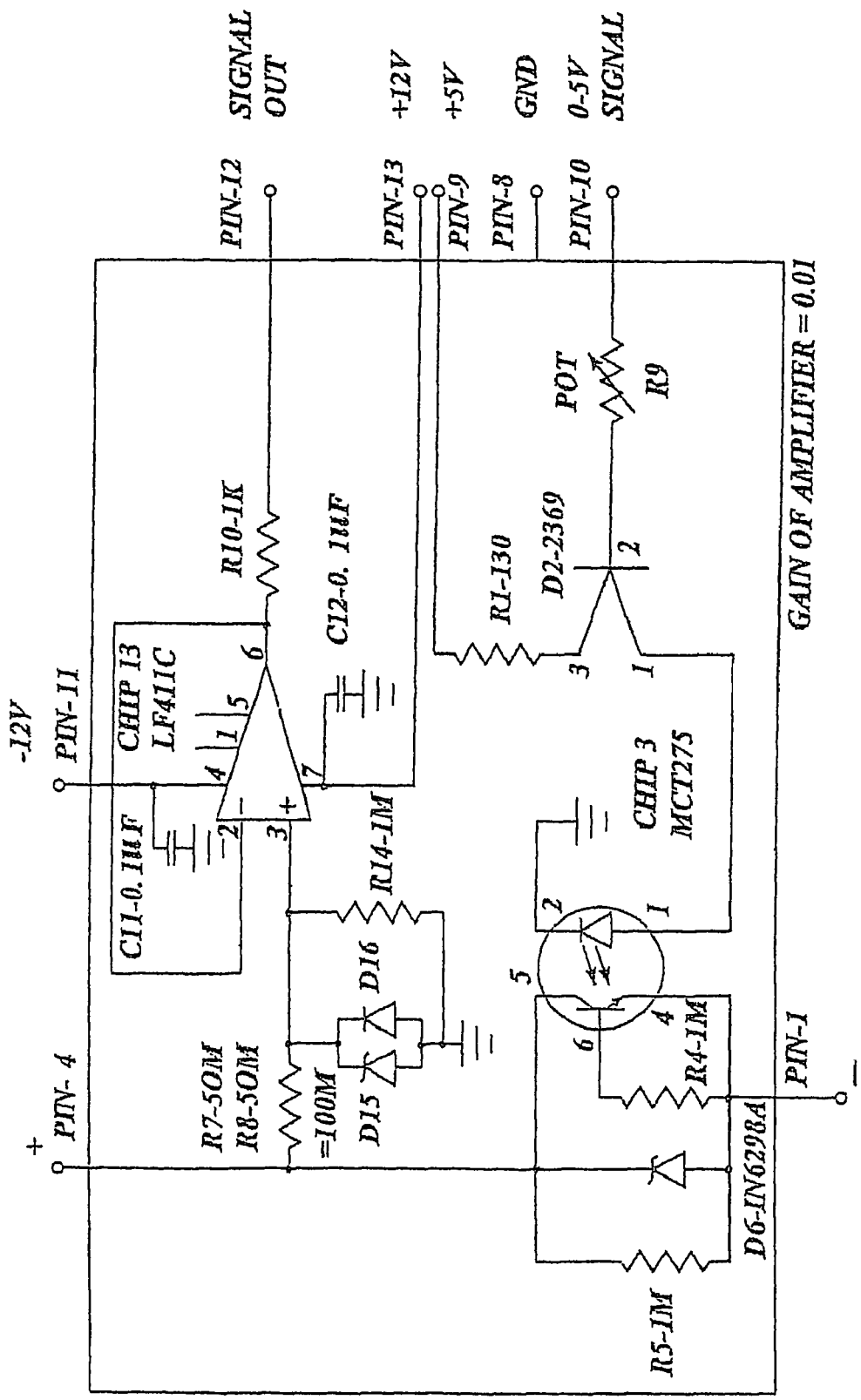
FIG. 32 is a circuit diagram of a representative controller unit.
Figure 33:
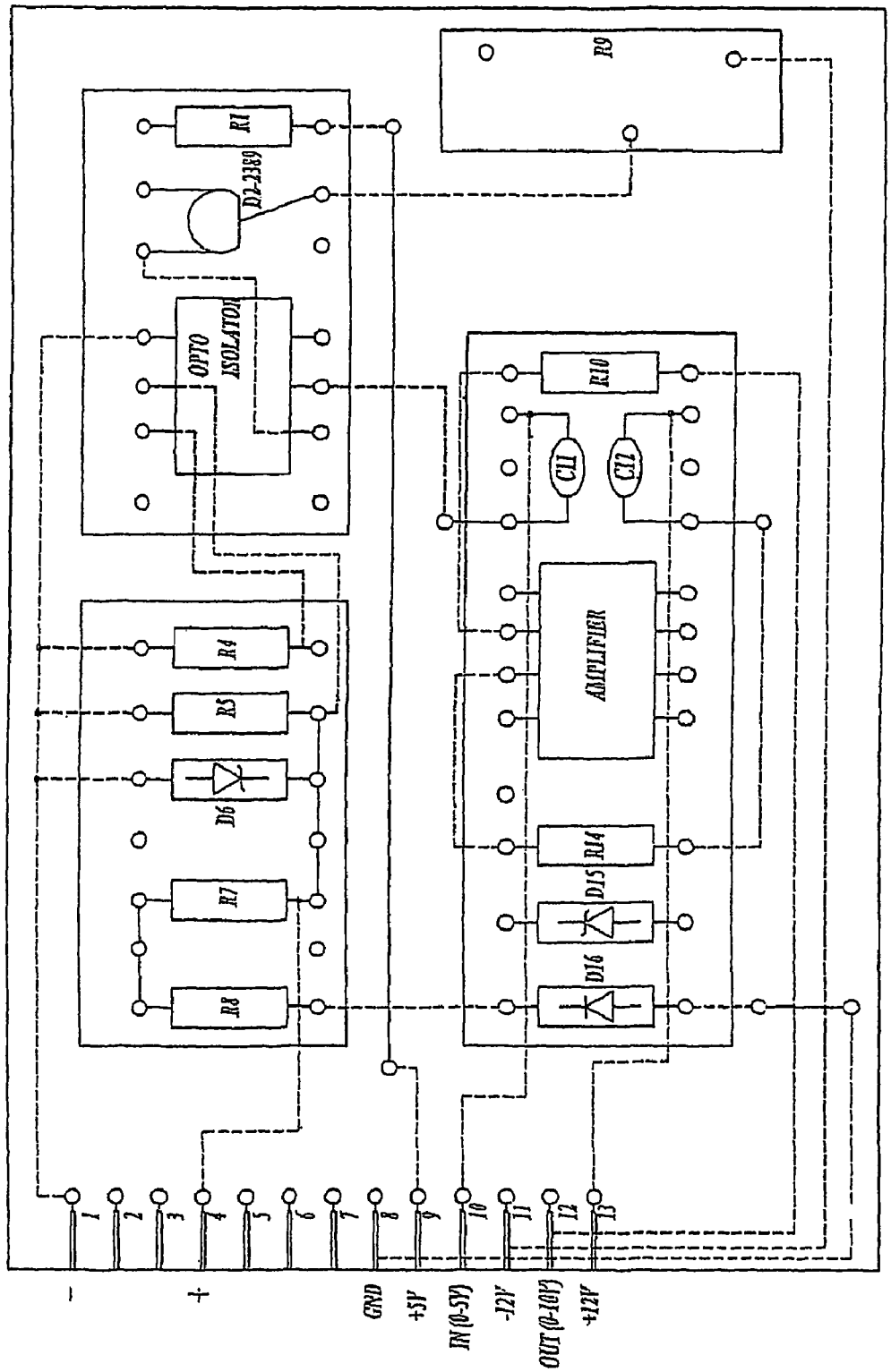
FIG. 33 is a circuit diagram of a representative controller unit.
Figure 34:
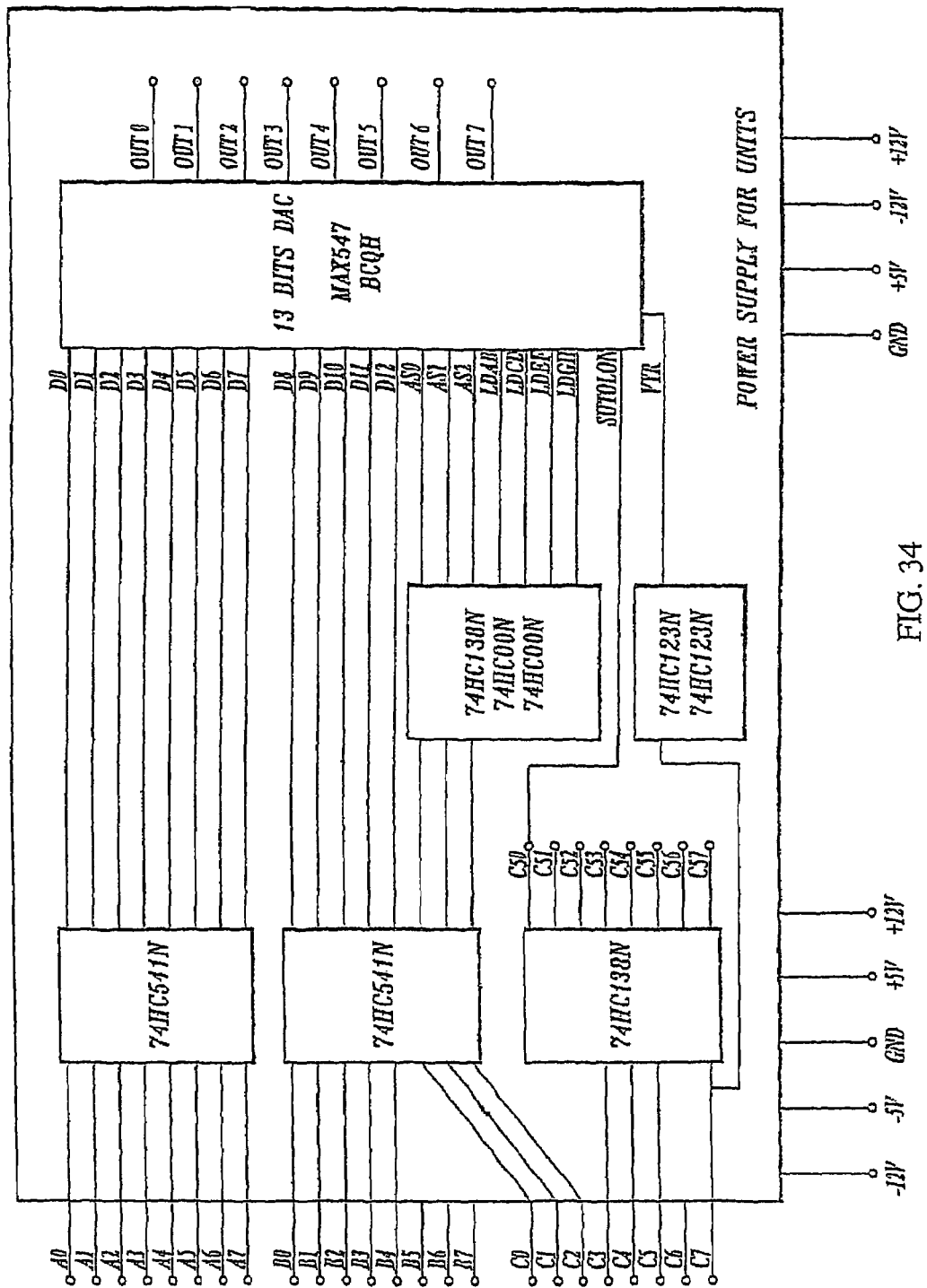
FIG. 34 is a schematic illustration of a representative DAC board circuit diagram illustrating connections.
Figure 35A:
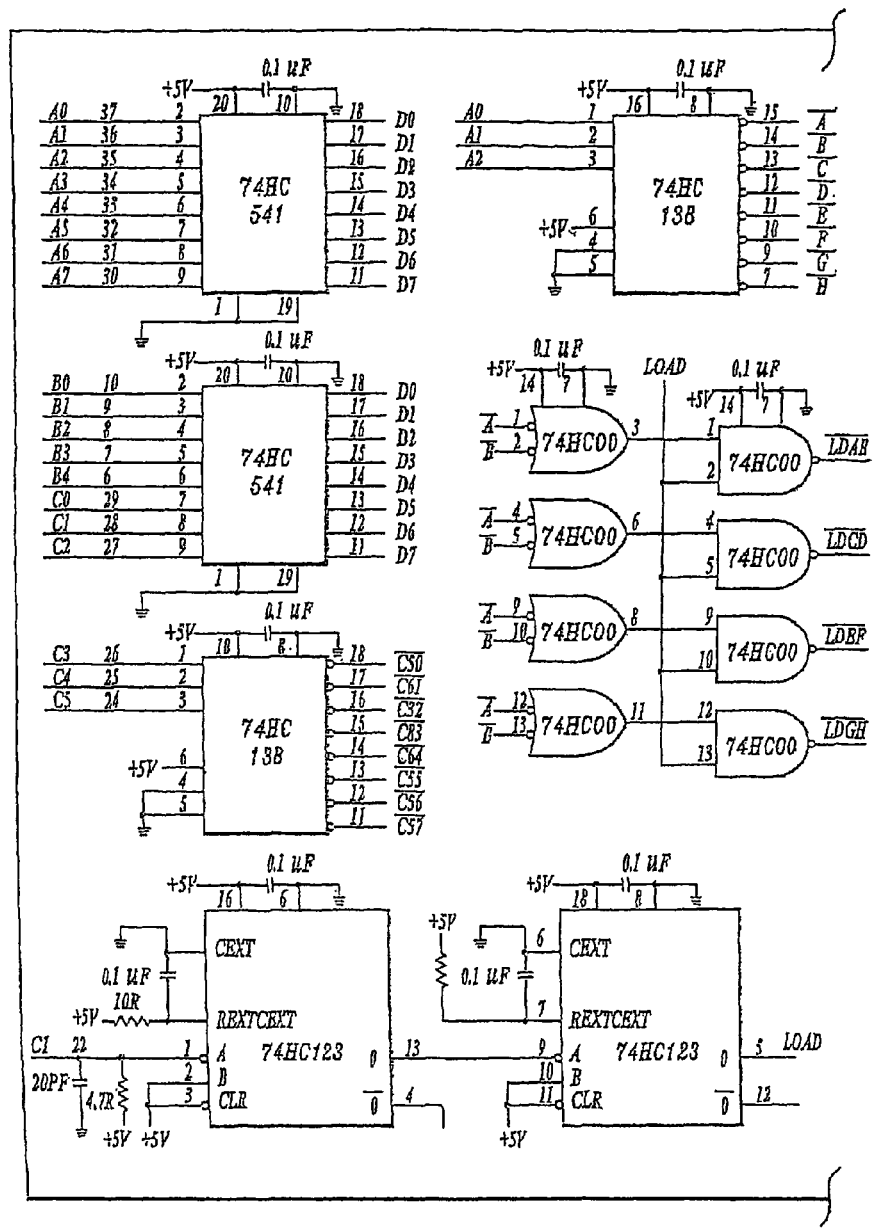
FIGS. 35A and 35B are schematic illustrations of a representative DAC board circuit diagram illustrating components.
Figure 35B:
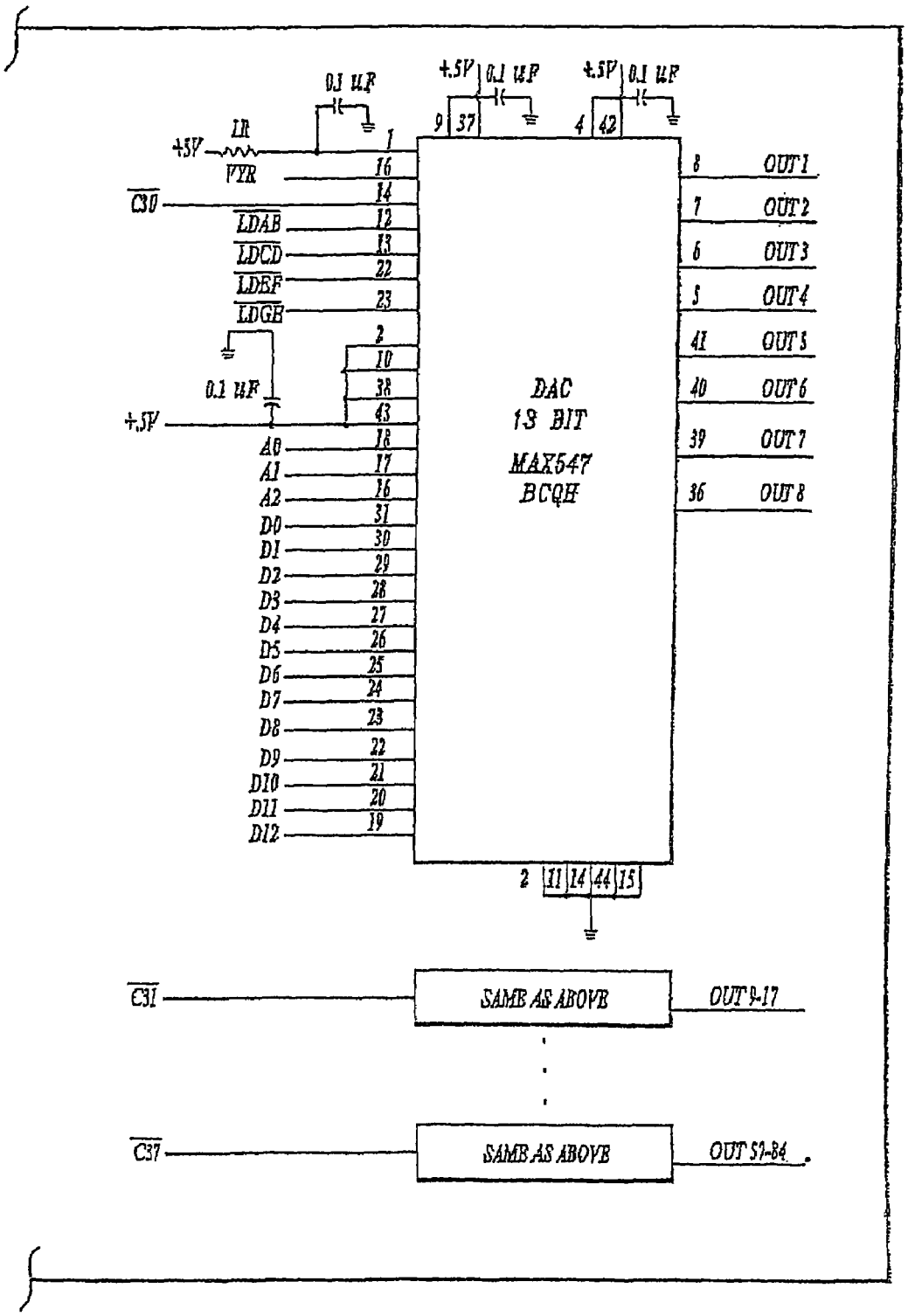

The gradient control is accomplished with PC-controlled circuits, diagrammed in FIG. 32, which are composed of electronic circuit boards. Pin 1 and 4 are connected to electrodes and neighboring units. The electrical potential on the electrode is reduced by $1/100$, then enters amplifier LF411C where the load of the signal is increased. The signal is then sent to EXP32 board through pin 12, and the control signal (pin 10, 0-5 V) from the DAC board adjusts the current going through the optical isolator MCT275. A circuit diagram of the controller unit is shown in FIG. 33. A logic diagram for circuit diagram for ADC board is shown in FIG. 34. A circuit diagram for the ADC board with components identified is shown in FIG. 35. The circuits scan all 50 electrodes and scale the signals down by $1/100$. Then the signals were sent to ADC board where 0-10V analog signals are digitized. The computer compares these readings with the programmed gradient, then sends its commands in digital signals to DAC board via the Digital I/O boards. In the DAC board, the command signals are converted to 0-5V analog signals, then sent to the 50 units on the PC monitor/controller board. Those units adjust the current going through the units, or we can say change the values of resistance $Rx_i$. Note that the $Rx_i$ do not exist physically, and they are the resistance to current going through the chip MCT275, an optically isolated controller. The scan/response cycle for the circuits is set at about 0.5 sec, and could be adjusted by the program.

A 600V DC power supply (Xantrex) supplies power to the chamber. The power to all the boards is supplied by the computer. As noted above, the second chamber can include more than one electrode array. For example, two electrode arrays can be associated with a single separation chamber in a configuration in which the separation chamber is positioned in between the two arrays. Similarly, the second chamber can include, for example, four arrays positioned about a separation chamber in a quadrupole-type configuration. Other preferred embodiments can include more than one second chamber, each having one or more electrode arrays.

In certain preferred embodiments, a pair of electrodes or optionally an array of electrodes is utilized to generate the electric field, with a gradient arising by means of the configuration of the separation chamber, optionally in conjunction with a configured electrode chamber and/or electrode array, as described above. In such embodiments, the configuration of the separation chamber and/or the electrode chamber is itself subject to dynamic control, either by the user or by computer control. Such embodiments employ, for example, movable or pivotable walls such that the shape and size of the chamber can be altered during the course of a focusing run to provide dynamic control over the strength and/or shape of the electric field gradient. Where the separation chamber configuration is dynamic, the gradient in the hydrodynamic force is advantageously subject to dynamic control, providing still more flexibility to the separation methods available. Suitable configurations employing dynamically-controlled chamber configurations will be readily apparent to one skilled in the art, given the benefit of the present disclosure.

Without wishing to be bound by theory, it is presently understood that the device is based on the principle of opposing two counteracting forces to create a dynamic equilibrium point. The force in one direction is a resultant of bulk fluid flow, commonly referred to a chromatographic flow, which imposes a hydrodynamic velocity on solutes in the stream. In the opposite direction, an electrophoretic velocity is induced with the application of a voltage to the stream containing solutes. The magnitude of the hydrodynamic velocity is proportional to the hydrodynamic radius or apparent size of the solute, and is adjustable with changes in the rate of chromatographic flow and/or with changes in the shape and/or size of the separation chamber. The hydrodynamic velocity, as noted above, will vary throughout the separation chamber as a result of the non-uniformity of the separation chamber. As such, the hydrodynamic velocity is also dependant upon the shape and size of the separation chamber. In the opposite direction, an electrophoretic velocity is induced with the application of a voltage to the stream containing solutes. The electrophoretic velocity is proportional to the molecular charge of the solute, which is adjustable with changes in solvent pH or composition. The hydrodynamic radius of an analyte is independent of the charge, and thus is independent of the electrophoretic velocity of the analyte. Thus, the provision of a gradient in the electric field and in the flow rate advantageously provides two independent means of achieving separation of charged analytes, thus increasing the likelihood of being able to separate multiple analytes. At a point in the separation path where the opposing velocities are equal in magnitude, yielding a net zero velocity, is the focal point for a particular solute. The focal point is one of a dynamic equilibrium for the solute, whereby any movement from that point results in a non-zero velocity and a restoring force. In establishing a desired electric field gradient, those skilled in the art will recognize that some compensation must be made in the gradient-establishing parameters (i.e. the shape of the electrode chamber or the settings for the electrode array) to address the perturbation or influence in the electric field caused by the non-uniformity of the separation chamber. That is to say, once a particular separation chamber configuration is desired, such that a desired hydrodynamic force gradient is established, that configuration must be taken into account when determining the appropriate configuration of the electrode chamber to achieve the desired shape of the electric field gradient. For example, while a hyperbolic electrode chamber would, in conjunction with a uniform or non-configured separation chamber, lead to a linear field gradient, the electrode chamber must deviate from hyperbolic to achieve a linear field gradient in the presence of a non-uniform separation chamber. Determination of suitable chamber configurations will be readily apparent to those of skill in the art, given the benefit of the present disclosure.

When the collected and held-in-place solute or analyte is to be released, the electrical field can be decreased or eliminated or the flow rate increased. The concept of electric field gradient focusing is illustrated in FIG. 1, where a constant bulk fluid flow is counteracted by a linear gradient in the electric field strength. A bulk buffer flow pushes solute to the right, while being counteracted by an electrophoretic force in the opposite direction. The magnitude of the electrophoretic force varies along the axis of the separation chamber. FIG. 26 further illustrates this concept. First, negatively charged proteins focus in an increasing field gradient with the electric field in the same direction as the convective flow of buffer (A, C, E). Second, positively charged proteins focus in a decreasing field gradient with the electric field in opposite direction as the convective flow (B, D, F). The amount of charge carried on protein molecules are closely related to the pH of the buffer and are generally different from species to species. The migration rate is directly proportional to the amount of charge carried which is generally different from specie to specie. Therefore, distinct stationary accumulation zones for differently charged species are generated along the column. In order to focus the charged protein in the chamber, the direction of electric field, the slope of field gradient and the pH of the elution buffer must be matched. Otherwise, the target protein will be flushed out or concentrated at the very top of the column, allowing no separation at all.

Certain preferred embodiments of the electrophoretic devices comprise a layered assembly. The separation chamber and the electrode chamber are separated by a porous membrane. The separation chamber is a conduit that has a shaped geometry, where sample peaks are loaded, held and off-loaded or eluted. The electrode chamber may have a shaped geometry and has at least one built-in electrode pair, where there is one anode and one cathode. Application of a DC voltage to the electrodes results in an electric field, with an intensity inversely proportional to the combined separation chamber and electrode chamber cross-section at a given point. The electric field strength will vary along the axis of flow. To generate a linear electric field gradient, the combined chambers typically will have a hyperbolic shape, but nonlinear fields are possible by selecting the appropriate combined chamber geometry. The magnitude or slope of the field gradient may be manipulated by adjusting the voltage applied to the electrodes. The porous membrane must conductive for the passage of small ionic species and electrical current, thereby communicating the electric field to the separation chamber. The pore size of the membrane is such that all molecules designated as samples will be retained in the sample chamber. A buffer system typically is required for the device to maintain stable pH and provide sufficient conductivity to carry the electrical current throughout the fluidic passages of the electrode chamber and separation chamber. FIG. 2 is an exploded view of an exemplary device with an electrode pair, as well as the representative orientation of device components. The arrow heads indicated the direction of buffer flow. The electric field gradient would cause solute to migrate in the opposite direction to buffer flow.

Electrophoresis devices are provided in accordance with another aspect. The devices comprise a non-uniform separation chamber and two or more electrodes separated from the chamber by a membrane. The electrodes are operative to generate an electric field in the separation chamber, wherein the non-uniformity of the separation chamber is operative to establish a gradient in an electric field generated in the separation chamber by electrodes and to generate a gradient in the hydrodynamic force along the separation chamber. In certain preferred embodiments, the separation chamber comprises a non-uniform tube, with electrodes plated on the interior surface of the tube and coated with a porous, conductive coating membrane, The porous coating is chosen such that it allows small molecules such as buffer ions to pass but prohibits molecules of the size of the analytes from passing through and contacting the electrodes. In other preferred embodiments, the separation chamber comprises a porous, non-uniform tube, with electrodes plated on the exterior of the tube. The porous tube is likewise chosen to be porous to small molecules and to prohibit passage of molecules of the size of the analyte(s). Other suitable configurations of devices that lack an electrode chamber will be readily apparent to those of skill in the art, given the benefit of the present disclosure.

The separation chamber can either be an open channel or can be packed with a media, such as a gel or granular packing, to reduce the convective dispersion and help maintain sharp peaks. In certain preferred embodiments, the separation chamber contains a fluid medium. Suitable fluid media include simple fluids such as, for example, buffered water. Also included are complex fluids, for example, a water/acetonitrile/methanol mixture, or polymer solutions such as, for example, linear polyacrylamide, polyvinyl alcohol, methyl cellulose solutions and the like. The fluid media in certain preferred embodiments further comprises a chromatography support medium or packing. Suitable packings can be of any size or type provided that the solute being focused does not irreversibly bind to the packing. Suitable packings include porous and nonporous, pellicular and tentacle, glass, plastic, ceramic, and any nonconductor or semiconductor. Other suitable packings include ion-exchange, affinity, reverse phase size exclusion, gel filtration and hyperbolic interaction supports.

The electrode chamber can have a constant cross-section or, like the separation chamber in accordance with principles disclosed here, can have a variable configuration, that is, a configuration other than a constant cross-sectional shape and one that can be adjusted during operation of the device. Height and/or depth can be varied in the sense of being non-uniform along the flow path and/or in the sense of being adjustable or controllable during operation.

EXAMPLE

It will be apparent to those skilled in the art, given the benefit of this disclosure, that the electrophoresis devices, processing systems and methods disclosed here have application in a wide variety of research, development and industrial applications. The following preferred embodiments are discussed below for illustration and as examples, and not necessarily to limit the scope of the invention.

In accordance with one exemplary embodiment, a substantially planar electrophoresis device in accordance with those disclosed herein has the following attributes:

Exemplary operating electric field strength of 200 V/cm, with applied voltages depending on the length of the chamber.

Electrode buffer flowrate of 0-10 L/min.

Separation chamber buffer counterflow flowrate 0-20 microliters/min

Buffer conductivity 0-1 S/cm. The conductivity of 20 mM Tris-phosphate at pH 7.25 is approximately $1.025 \times 10^3$ microSiemens/cm.

Dimensions of the separation chamber are 1 mm wide×0.5 mm deep. The length may vary from about 2.54 cm to 12.7 cm long.

Depth of the electrode chamber is 3.2 mm.

Distance between the main pair of electrodes varies from 2.54 cm. to 12.7 cm.

Width of the electrode chamber is 1.6 mm at the most narrow point to 1.6 cm at the widest.

The focusing chamber has an active region of from 1 cm to 12.7 cm for varying scales of the device, e.g., 2.54 cm for the other attributes listed here.

The separation chamber is defined by side walls (i.e., walls substantially perpendicular to the plane of the porous, conductive membrane) with a hyperbolic shape resulting in a linear electric field gradient (see FIGS. 1 and 2). The separation chamber shape can be tailored to generate a specified electric field (e.g. non-linear) to perform a custom separation.

A single separation chamber suitable for focusing either positively or negatively charged molecules.

The following are adaptations of the device configuration and the application identified:

A single chamber with a switchable power supply to select focusing either positively or negatively charged molecules.

Two chambers configured in a serial fashion, at least one of which is in accordance with the devices disclosed herein, with a three-way diverter valve positioned at an intermediate point, to allow "filtering" and isolation of target molecule(s). (See, e.g., FIG. 3.)

Two chambers, at least one of which is in accordance with the devices disclosed herein, configured in a serial fashion to focus both positive and negative molecules simultaneously.

The device can be constructed of any suitable material that is compatible with either aqueous or organic solvents, or both, depending on the intended application and environment of use. Exemplary materials include PEEK, TEFLON, acrylic, etc. Thus, for example, the separation chamber can be etched or otherwise formed as a configured groove or channel in a substrate of such material. The membrane seated against the substrate completes the separation chamber, leaving the ends open (preferably valved) for flow. The device may be constructed of material that is optically clear over the UV-Vis-IR spectral range to permit imaging or detection of isolated molecules in the chamber. This may include UV transparent acrylic, quartz, TEFLON AF, etc.

Detection strategies for such devices may also include monitoring the entering and exiting streams for tracking of materials. These would be considered point detectors. If the device is constructed of optically clear material, as mentioned above, point detectors could be spatially distributed along the length of the chamber, as opposed to imaging the entire chamber. Point detectors may be distributed throughout the system for overall tracking of material (e.g., at the exit of a switching valve to monitor routing of peaks).

As disclosed and described above, the electrophoresis device uses a porous layer to separate the electrode chamber from the separation chamber. The porous layer may be a dialysis membrane, ceramic membrane or other porous material that allows conduction of ions and electrical current. The molecular weight cut-off (MWCO) for the porous layer may range from 100-30,000 MW. Typically, small molecule applications may require a porous layer having a 100-200 MWCO and proteins applications may require a porous layer having a MWCO>1000.

An exemplary system in accordance with the present disclosure may employ auxiliary equipment such as any or all of the following:

A dynamic power controller unit to provide a supply of up to 300 V on 25 independently controlled channels, the user optionally having full control over voltage settings, with built in data acquisition for recording of voltage settings.

Capillary-scale UV-Vis flowcell to allow UV-Vis interrogation of streams for performing absorbance spectrophotometry across the spectral range 200-1100 nm.

UV-Vis light source with fiber-optic coupling capability to provide illumination energy for absorbance spectrometry over the range 200-1100 nm.

HTSL-1100 microfluidic sample loader to provide the ability to automatically inject microliter quantities of sample into a precision controlled flow stream with flowrates of 1-20 microliters/min.

A GUI software control bench to interface the HTSL for flexible control of sample loader operations.

A suitable computer, such as, for example, a Pentium IV 2.0 GHz computer, 512 MB Ram, 30 GB HD, CD-RW to provide computational power to execute and manage the HTSL and spectrometer software and data acquisition.

Figure 5:
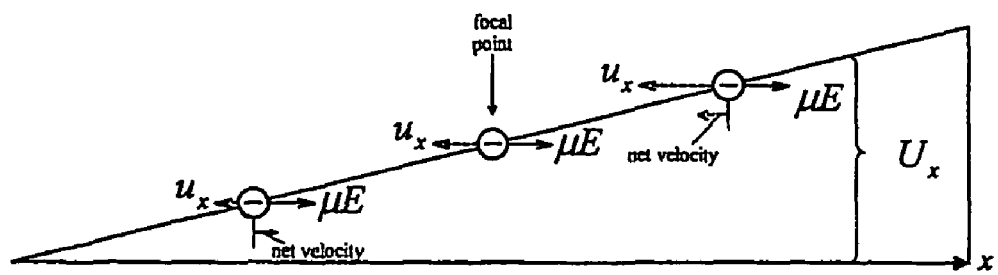
FIG. 5 is a graph further illustrating the principles of EFGF.

FIG. 5 is a further illustration of electric field gradient focusing. In FIG. 5 a charged solute is pushed from left to right by a chromatographic flow. The electric field will impose an electrophoretic migration velocity proportional to the mobility of the solute. At the point where the elution and migration velocities balance is considered the equilibrium focal point for a solute.

EFGF enables focusing of target molecules at pH values distant from their isoelectric points (pI) and in simple buffer systems. Therefore, EFGF has a distinct advantage over isoelectric focusing (IEF), which has the following inherent limitations: many solutes have low solubilities at their isoelectric points, entire classes of solutes cannot be focused by this method either because they degrade at their isoelectric point (pI), e.g., nucleic acids, or they do not have a readily accessible pI, e.g., polystyrene latexes, and the use of ampholytes for generating the pH gradient can increase the cost per separation substantially. Compared to chromatographic techniques, the equilibrium focusing technologies allow a sample to be "held-in-place", rather than flow-thru elution, providing a method to collect peaks from multiple injections or trials without having to manually combine collected fractions. Furthermore, the chamber configurations for EFGF allow the separation conditions (e.g., field gradient, buffer composition, pH) to be altered in situ, providing a means to adjust separation resolution or evaluate behavior of target analytes in a changing environment. There is additional benefit of the device with use of an electric field gradient and a hydrodynamic force gradient as separation driving forces, which promotes flexibility for target molecule elution from the chamber. The slope of the electric gradient can be decreased in a stepwise fashion, and/or the hydrodynamic force can be increased in a stepwise fashion, to selectively release solutes "trapped" within a "mobility window" (i.e., the field strength of the lower gradient setting is insufficient to retain molecules having electrophoretic mobilities within the "step"). Since the holding force on the sample peaks is an electrophoretic migration, devices in accordance with those described herein will act on charged molecules or any neutral molecules labeled with charged groups or modified to possess an apparent charge. Given that the majority of DNA, proteins, and other small molecules (e.g., metabolites) are charged in an aqueous environment, these devices and methods will have application to separation or management of a very broad range of biological samples. In general, the field gradient focusing technologies have been described as providing separation strategies that are orthogonal to IEF and various chromatographic techniques, therefore, devices and methods in accordance with those described herein may provide researchers with an attractive alternative to LC and PAGE for separation of complex mixtures.

In accordance with certain preferred embodiments, the features, attributes, and benefits that can be provided by devices and methods in accordance with those described herein include:

Sample concentration or preconcentration into small microliter volumes

In-line buffer exchange

Capability to capture peaks from multiple trials

Alternative mode of action for separations

Simple buffer systems

Broad range of analytes and application for separations

Operates as stand-alone or integrated component

Small device footprint

Figure 6:
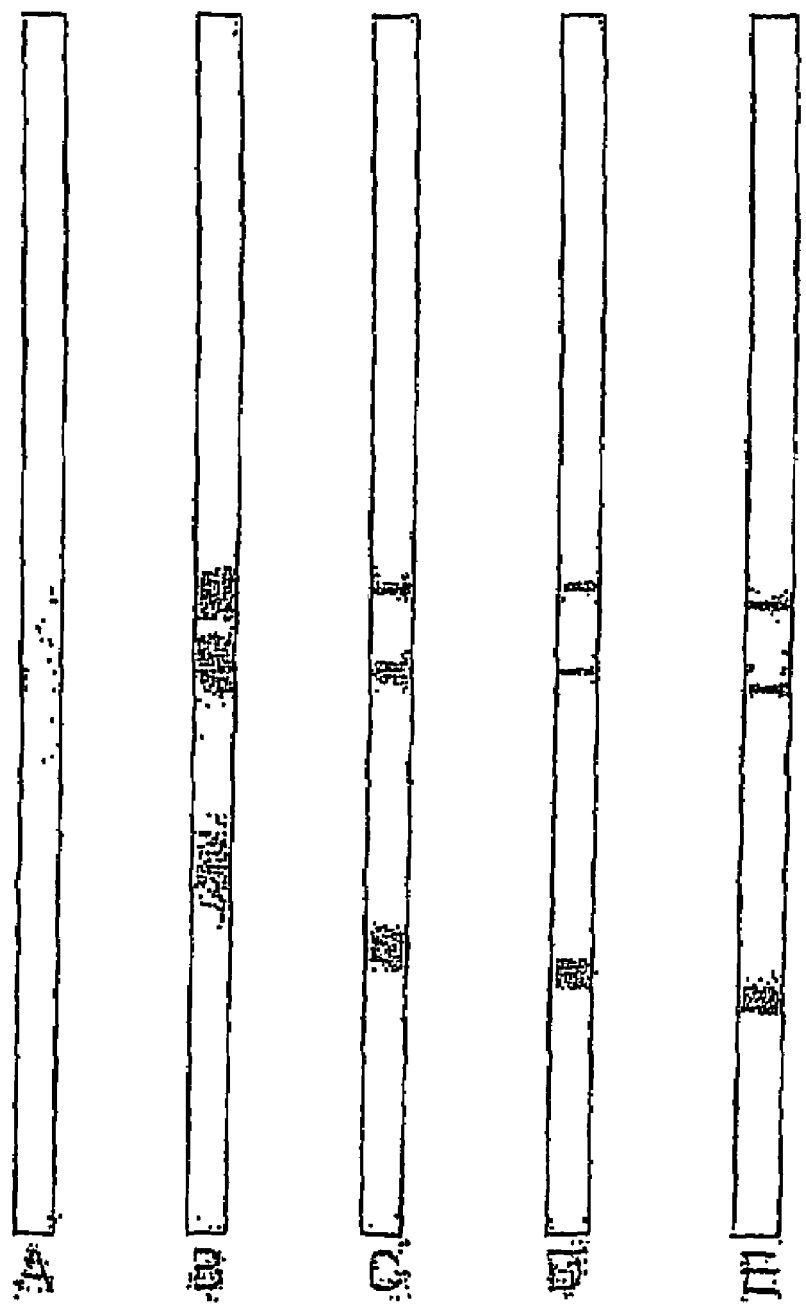
FIG. 6 is a series of images showing three injected proteins coming into focus.

Systems and devices disclosed here can be packaged as a stand-alone device or as a value added accessory to other separation devices to expand the repertoire of options for resolving complex mixtures. The inclusion of advanced detector markets (e.g., mass spectrometry and nuclear magnetic resonance) enhances the functionality of said methods and devices The inherent simplicity of preferred embodiments, e.g., as illustrated in FIG. 2, is advantageous in many applications. Referring again to FIG. 2, the conductive layer (e.g., a dialysis membrane) separates the separation chamber, which is tailored with a hyperbolic curvature to form a linear field gradient, from the electrode chamber. The conductive layer should allow passage of buffer ions and electric current, but should have pore structure that restricts translocation of target molecules from the focusing channel. FIG. 6 presents a series of images extracted from a simulation of a focusing system where three proteins have been injected as a dilute, homogenous mixture. According to model results, a high mobility molecule (small or strongly charged) moves fast to its equilibrium point. Therefore, a focused band can be established in a relatively short amount of time. For a low mobility molecule (big and weakly charged), focusing to equilibrium occurs on a longer time scale. As an example, with field strengths ranging from 20-200 volt/cm, at opposite ends of the chamber, a molecule with an electrophoretic mobility of 5×10-5 cm2/volt.sec can focus into a 2 mm band in approximate 12 minutes, while a molecule with a mobility of 5×10-6 cm2/volt.sec will reach its focal point in approximately 2 hours. Slower moving analytes create a challenge for equilibrium focusing techniques, but an increase in focusing speed may be achieved at higher flow rates and higher field strengths. Since it is relatively easy to increase the system flow rate, extension of the operational range primarily focuses on increasing the field strength. The limiting factor to operational conditions may be joule heating and subsequent heat dissipation. It is presently understood that a small-scale device will be capable of 200 V/cm in a 20 mM Tris-phosphate buffer. These field strengths are similar to those used in conventional capillary-scale instruments. It would be advantageous to focus at higher field strengths, but it is believed that in at least certain embodiments fields of 250 V/cm or higher may yield uncontrollable temperature effects and 500 V/cm may prove unrealistic at this scale. FIG. 6 shows results of a simulation showing the focusing of a protein mixture. A) A faint smear can be seen near the mid-point of the column as two high mobility proteins begin to focus. B) Three distinct bands, representing R-phycoerythrin (pink), phycocyanin (blue), and myoglobin (brown), are observed at 2.5 min after applying the field gradient. C) and D) show the bands becoming more concentrated at 5 and 7.5 min into the focusing trial. E) Elution of the bands is initiated resulting in a shift downward towards the focusing chamber exit.

A general hyperbolic channel shape for a typical separation chamber would generate field strengths ranging from 20 to 200 V/cm at the widest and most narrow points of the channel, respectively, at an applied voltage of 300 V between a single electrode pair. Although a linear field gradient may be preferred for general focusing application, the field shape is not constrained to linear. As a matter of fact, the shape of the separation chamber, and where appropriate the electrode chamber, can be tailored to create a nonlinear field to address specific needs, and an electrode array could further shape the electric field gradient. A linear gradient would typically be the starting point for a separation.

Figures 7A, 7B, 7C:
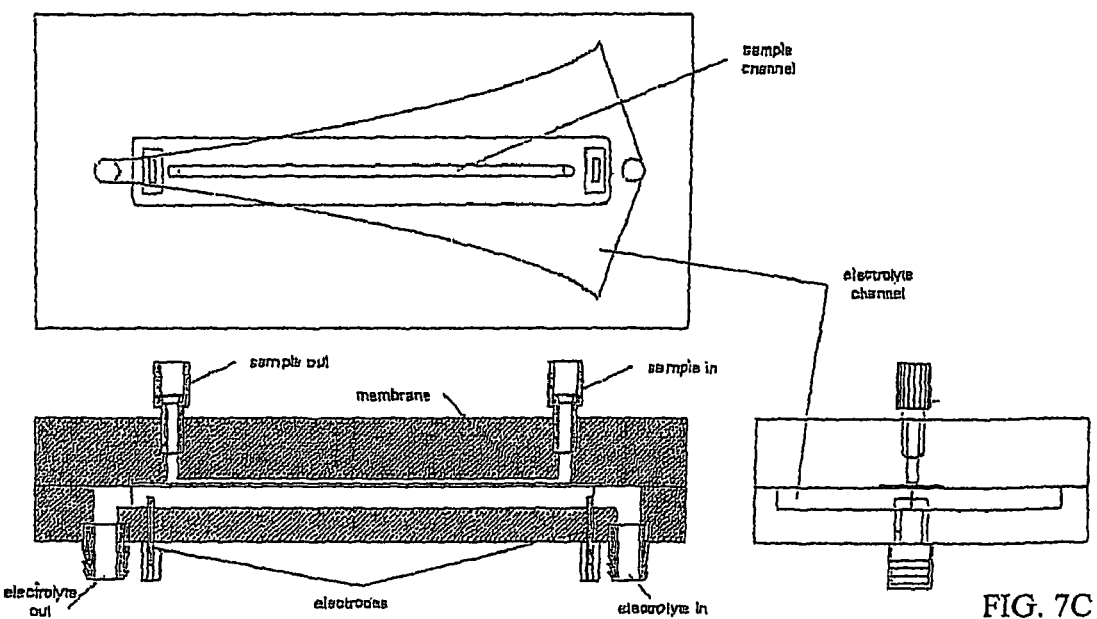
FIG. 7A-C are top views, a cross sectional side view, and a cross-sectional end view, respectively, of an exemplary device.

An exemplary chamber for the devices and methods disclosed here is illustrated in FIG. 7. Electrolyte sweeps through the electrode chamber to remove electrolysis products and joule heat. The separation chamber may be packed with a chromatographic media to stabilize convective perturbations. The chamber, itself, is seen to be an assembly of three functional layers including the sample focusing channel (upper most layer), the "conductive" membrane, and the electrode chamber (lower most layer). The two chamber layers may be fabricated from common plastics (e.g., acrylic or PEEK with TEFLON AF or quartz components) to allow visualization of the separation processes, however chemical compatibility will be a consideration in material selection. The electrodes, housed in the lower layer, are single electrode elements consisting of either gold or platinum metal to prevent hydrolysis-induced breakdown. Trade-offs in the focusing systems have been observed in balancing the operational range and resolution against the ability to dissipate heat.

The range of proposed electrophoretic mobilities accessible by devices and methods in accordance with those disclosed herein includes a wide range of the peptides that may be encountered when peptide mapping, thereby expanding the application base of the device, method and systems disclosed here.

Figure 8:
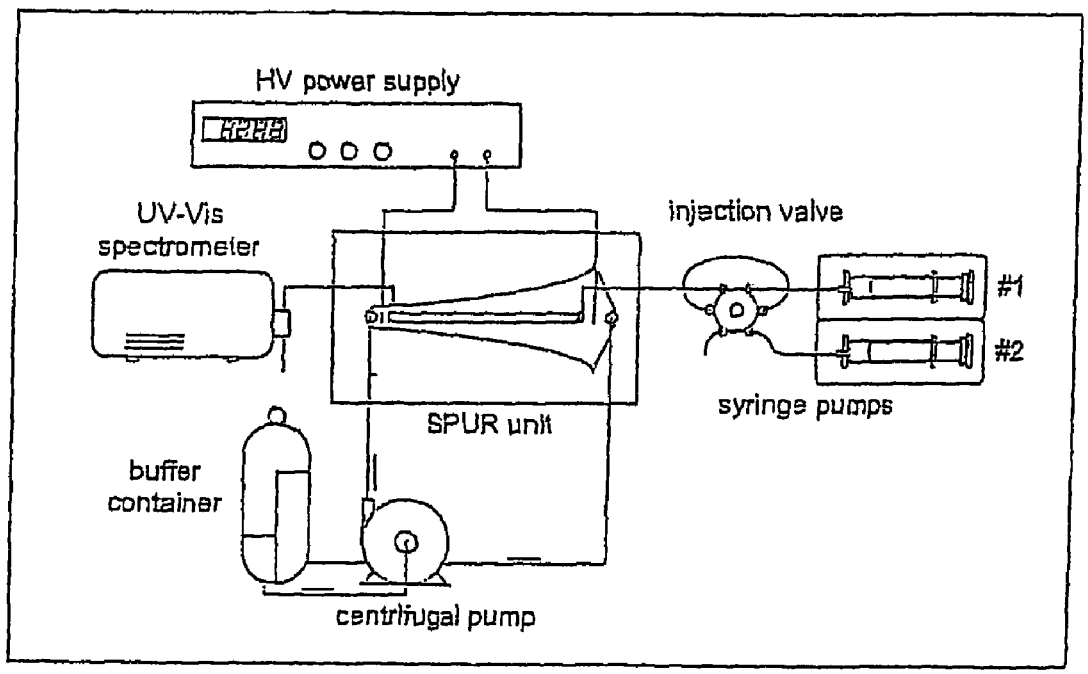
FIG. 8 is a schematic illustration of an exemplary system.
Figure 9:
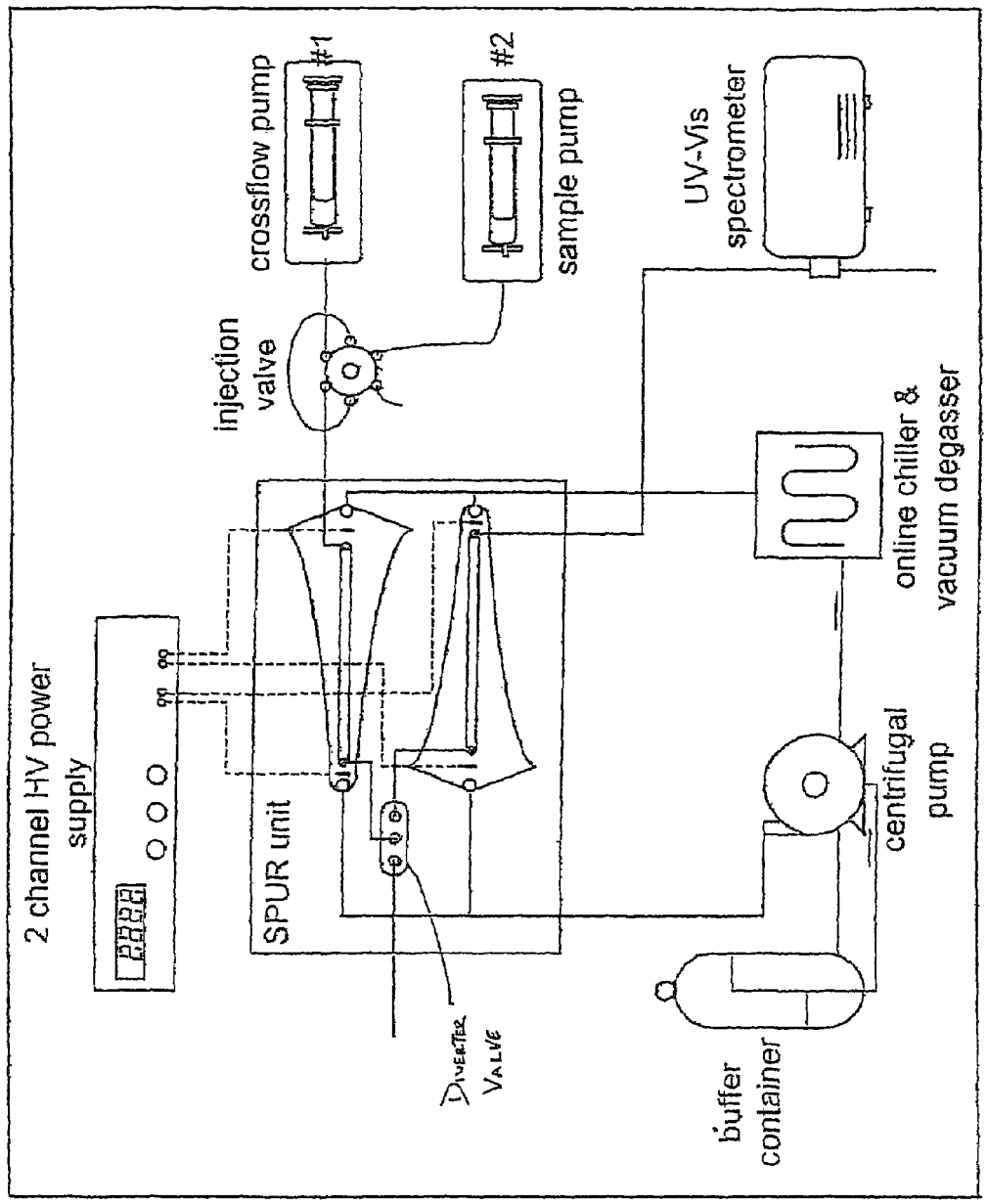
FIG. 9 is a schematic illustration of an exemplary dual-device system.

FIGS. 8 and 9 are schematic illustrations showing exemplary systems comprising devices in accordance with those disclosed herein, with FIG. 8 representing a single electrophoretic device and FIG. 9 representing an apparatus containing two electrophoretic devices. The devices can be controlled via RS-232, LAN, or contact closure interfaces and advantageously can be used with commercially available liquid handlers to allow unattended analyte preconcentration. Fluidic samples, for example, aqueous-phase samples, are injected into the first analytical or sample chamber with the trapping electric field turned on, and the sample is allowed to separate and focus into one or more bands of focused analyte. The electric field is then lowered to allow a low mobility band of analyte to exit or elute from the chamber. As exemplified in FIG. 8, the eluted band then passes to a suitable detector, here a UV-Vis spectrometer, for detection and quantification, and then exits to pass into any other desired sample treatment or detection apparatus. As exemplified in FIG. 9, eluted bands may be passed from the first electrophoretic chamber into a second electrophoretic chamber. In this fashion, bands can be located within either chamber by separately manipulating the strength of the electric field in each chamber. Such a design is advantageous in that it permits the removal of bands of intermediate mobility while allowing the apparatus to retain bands of higher and lower mobility in the electrophoretic chambers. For example, desired bands of low mobility can be eluted from the first chamber and permitted to flow into the second chamber while retaining the remaining bands on the first chamber. Subsequently, the undesired intermediate bands can be eluted from the first chamber and diverted, for example by means of a diverter valve, out of the device, for example into a separate detection and/or sample treatment apparatus or to a waste port. The remaining bands of high mobility can then be flowed into the second chamber and then to the detection/treatment systems as desired. Typical operating parameters of an apparatus of this type with a 1-inch chamber are shown in Table 1:

| | |
|---|---|
| Sample Amount | 10 micrograms total load |
| Focusing Time | 10 minutes |
| PH Range | 3-9, programmable |
| Temp. Range | 10-25° C. |
| Number of Electrodes | 2 |
| Eluent Flowrate | 1 µL/min. |
| Buffer Flowrate | 1 mL/min. |
| Maximum Voltage | 350 Volts |
| Maximum Current | 45 mA |
| Maximum Field Strength | 200 Volts/cm |

In each of FIG. 8 and FIG. 9, syringe pump #2 represents a device for the introduction of sample to the apparatus. It will be understood that such a device may comprise means for the introduction of free-standing sample, for example a syringe, or may instead comprise the output of an upstream instrument. Further, the UV-Vis spectrophotometer can be replaced by or be followed by any suitable downstream instrument or other sample detection, treatment, or collection device. In this fashion, the apparatus can be used to link up separate instruments in a hyphenated fashion, whereby the sample flows directly from one instrument into the apparatus and then into the next instrument. Additional injections may be used in certain preferred embodiments to accumulate or concentrate low abundance materials while holding previous samples in either the first or, where one is present, the second chamber. Alternatively, continuous flow of sample may be so used, or a combination of continuous flow and additional injections. Further, additional such electrophoretic devices may be used in serial or in parallel networks to provide additional separation flexibility for accumulating multiple analytes for collection or analysis. Additional peripherals may be added for any desired follow-on sample analysis, treatment, collection and the like. Other suitable apparatus designs will be readily apparent to those of skill in the art, given the benefit of this disclosure.

In certain preferred embodiments, the separation chamber comprises a cartridge-like insert that is capable of being easily removed and replaced. The separation chamber insert typically resides between an inlet and an outlet for flowing a fluid into and out of the insert chamber. The shape of the separation chamber is determined by the configuration of the insert. Such a configuration is particularly advantageous in that the configured chamber can be swapped out for chambers of different configurations, making a variety of electric field gradient shapes and strengths available in a single instrument. In other preferred embodiments, the electrode chamber comprises a cartridge-like insert that can be swapped out, for example, to permit changing between a non-configured separation chamber and a configured separation chamber. Typically, the electrode chamber insert will comprise the electrodes. In yet other preferred embodiments, both the separation chamber and the electrode chamber comprise cartridge-like inserts. Suitable cartridge configurations will be readily apparent to those of skill in the art, given the benefit of the present disclosure.

Figure 10:
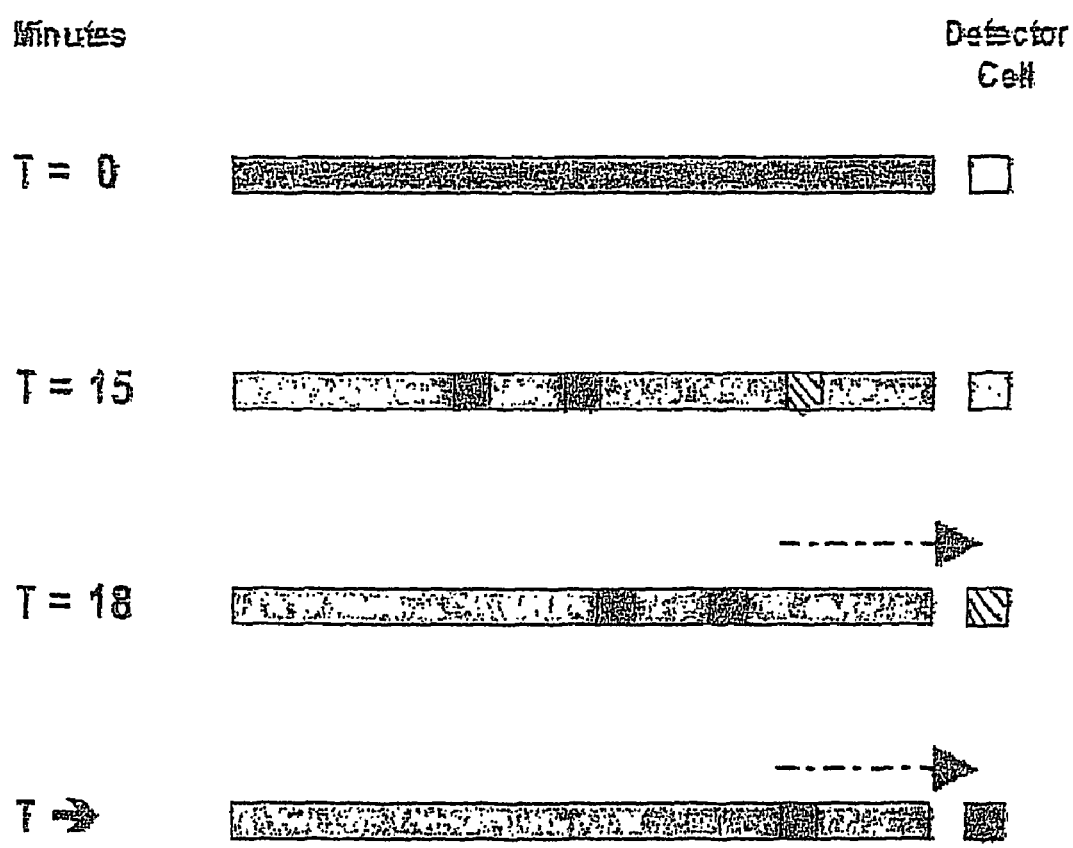
FIG. 10 is a series of images showing focused bands being eluted from an exemplary separation chamber.
Figure 11B:
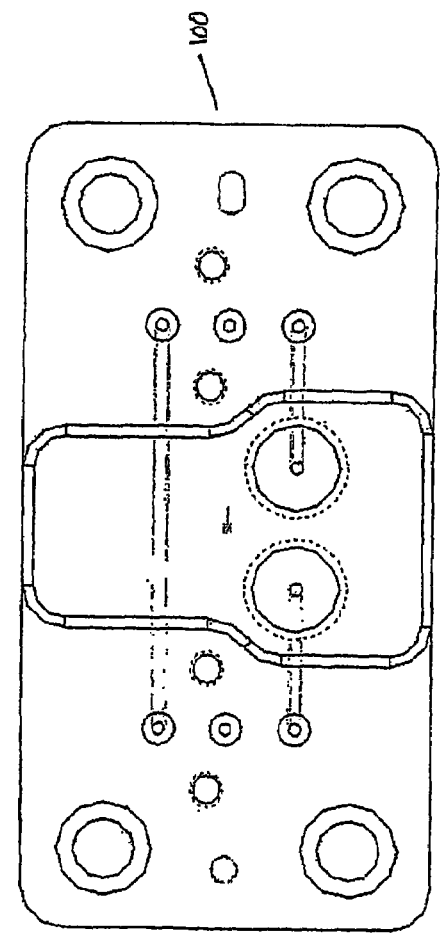
Figure 11A:
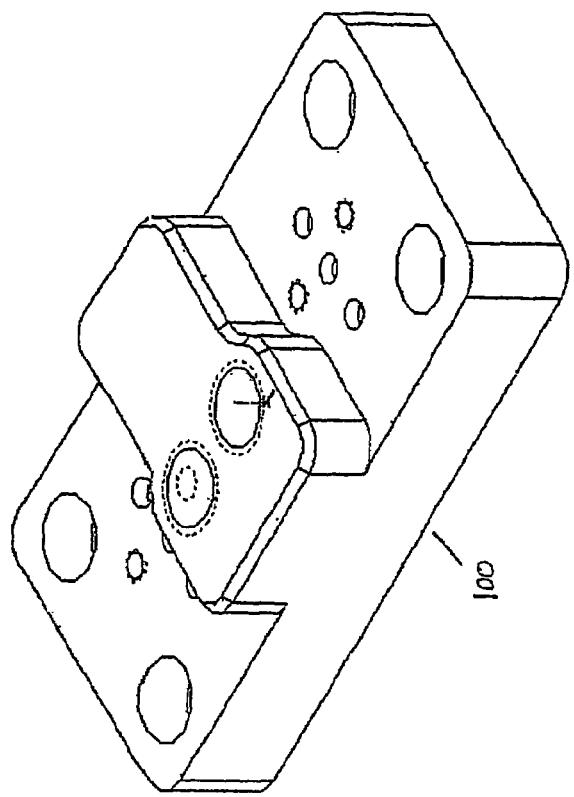
Figure 13B:
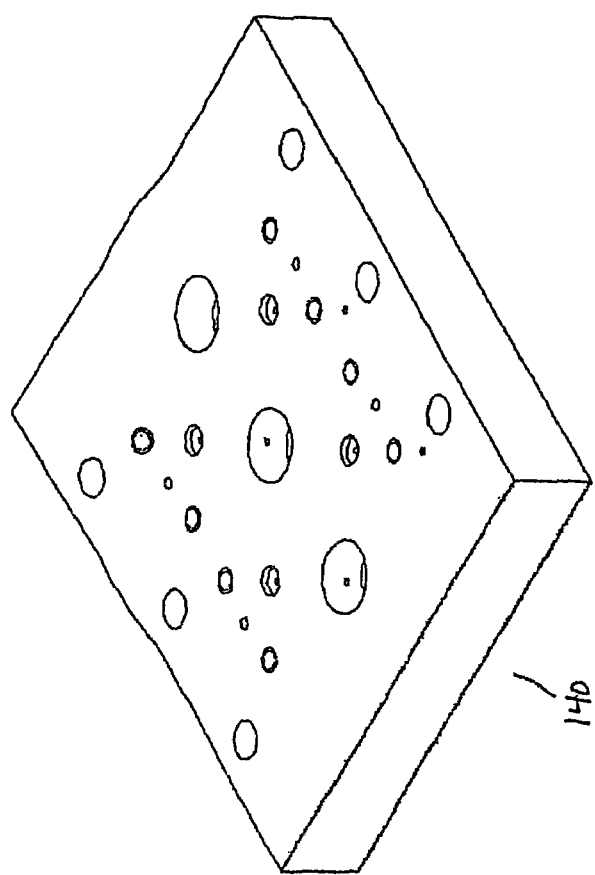
Figure 13A:
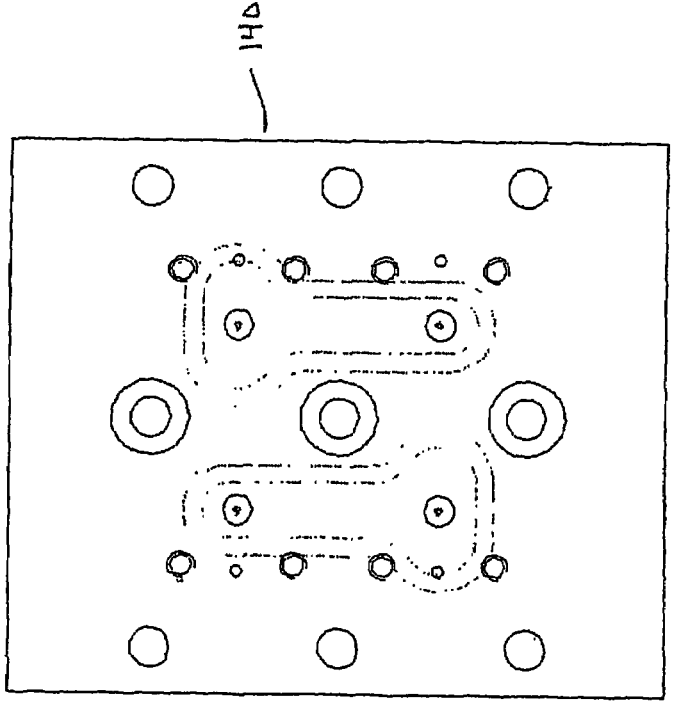
Figure 14:
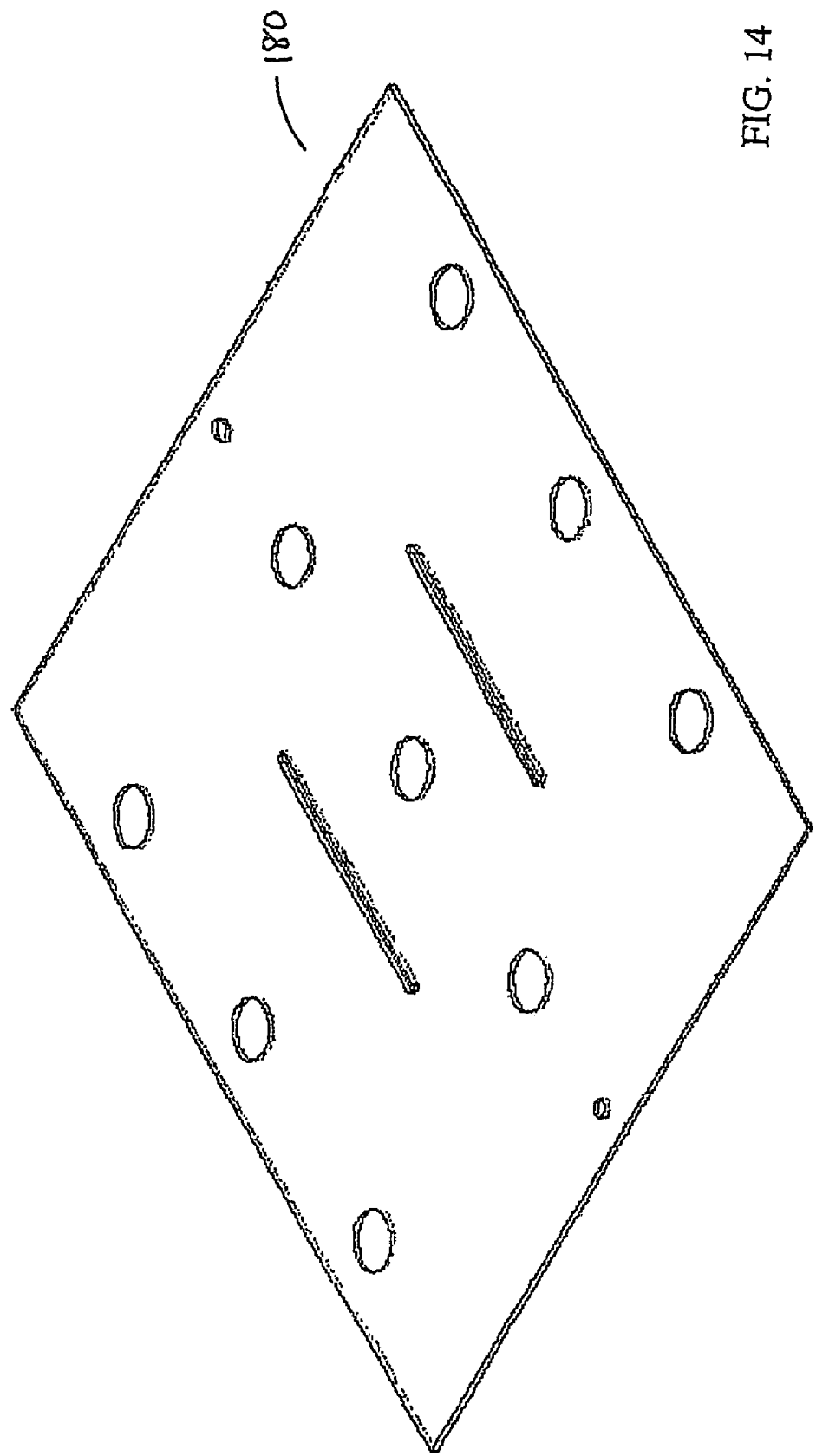
Figure 15B:
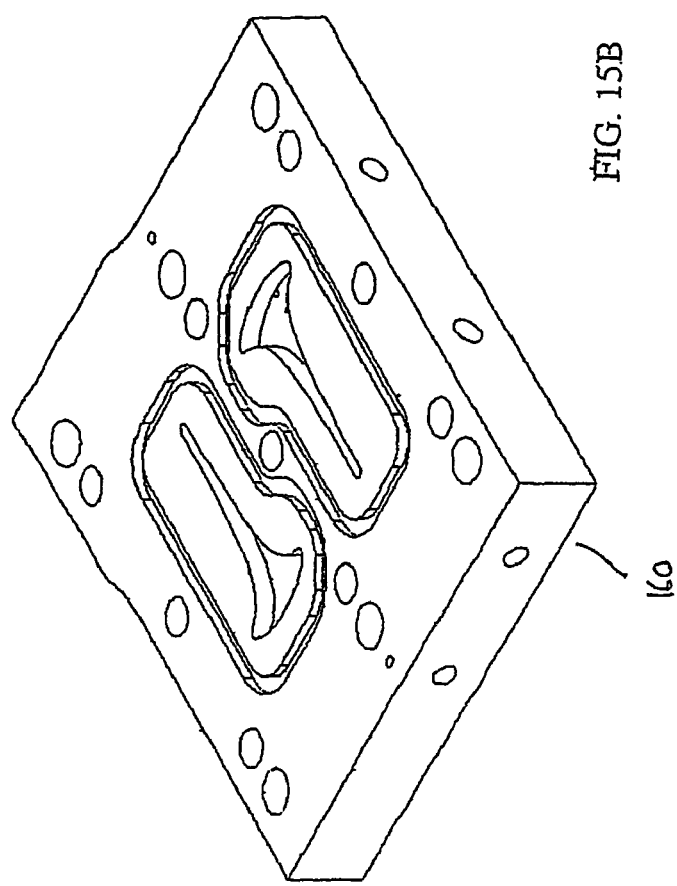
Figure 15A:
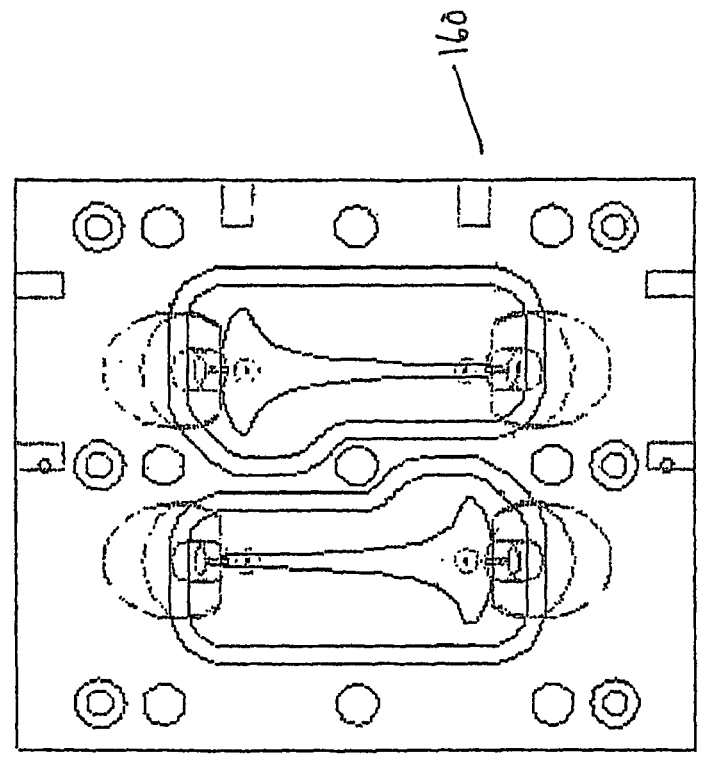
Figure 16:
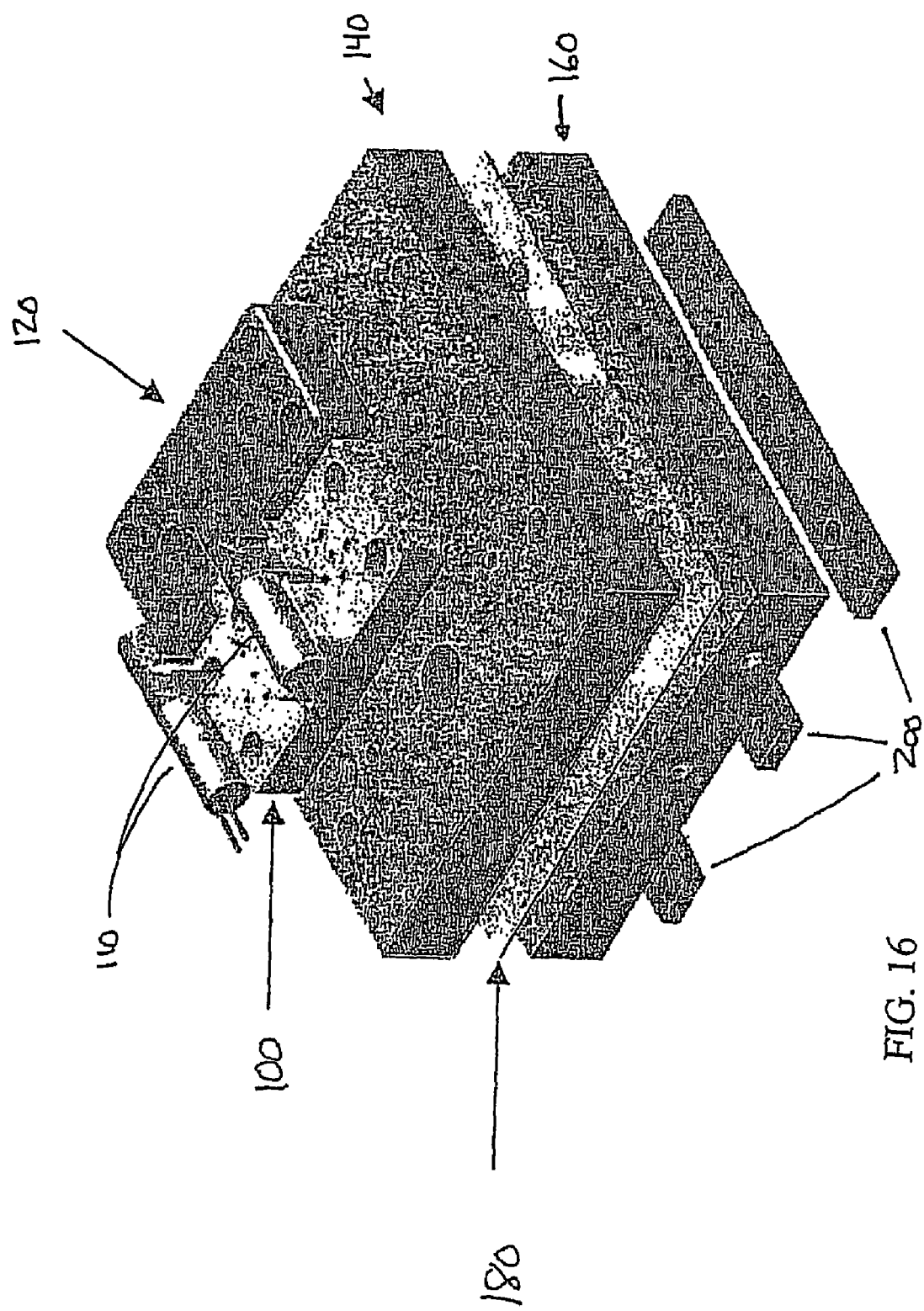

FIG. 10 presents a series of images extracted from a simulation of a focusing system, in which three analytes have been injected as a dilute, homogenous mixture, that illustrate a usage of a device in accordance with the disclosure herein to separate, retain, concentrate, and elute analytes. At the outset, sample is loaded into the device and the electric field is applied. At 15 minutes, the sample has separated and focused into three separate analyte bands, each of which may contain more than one species of analyte. The electric field is then lowered, here at 18 minutes, reducing the electrophoretic force that counters the chromatographic force to an extent sufficient to elute the band of analyte that has the lowest mobility to any suitable downstream detector or further sample treatment device, for example, into an optical flowcell for detection and quantification. Advantageously, the remaining bands of interest can be retained in the electrophoretic device by maintaining the electric field at the lower power level while the first band is analyzed. Each of the remaining peaks can then be eluted in the same fashion into the same downstream detector or further sample treatment device, or can be diverted into any other appropriate downstream device. Further, if desired, following elution of the band of lowest mobility additional sample can be loaded into the electrophoretic device for concentrating the remaining species; the two retained species will concentrate while the eluted species will not be retained in the device. As such, the device can be used to purify as well as to concentrate the species of interest. Other suitable applications of the device will be readily apparent to those of skill in the art, given the benefit of the present disclosure.

Figure 17:
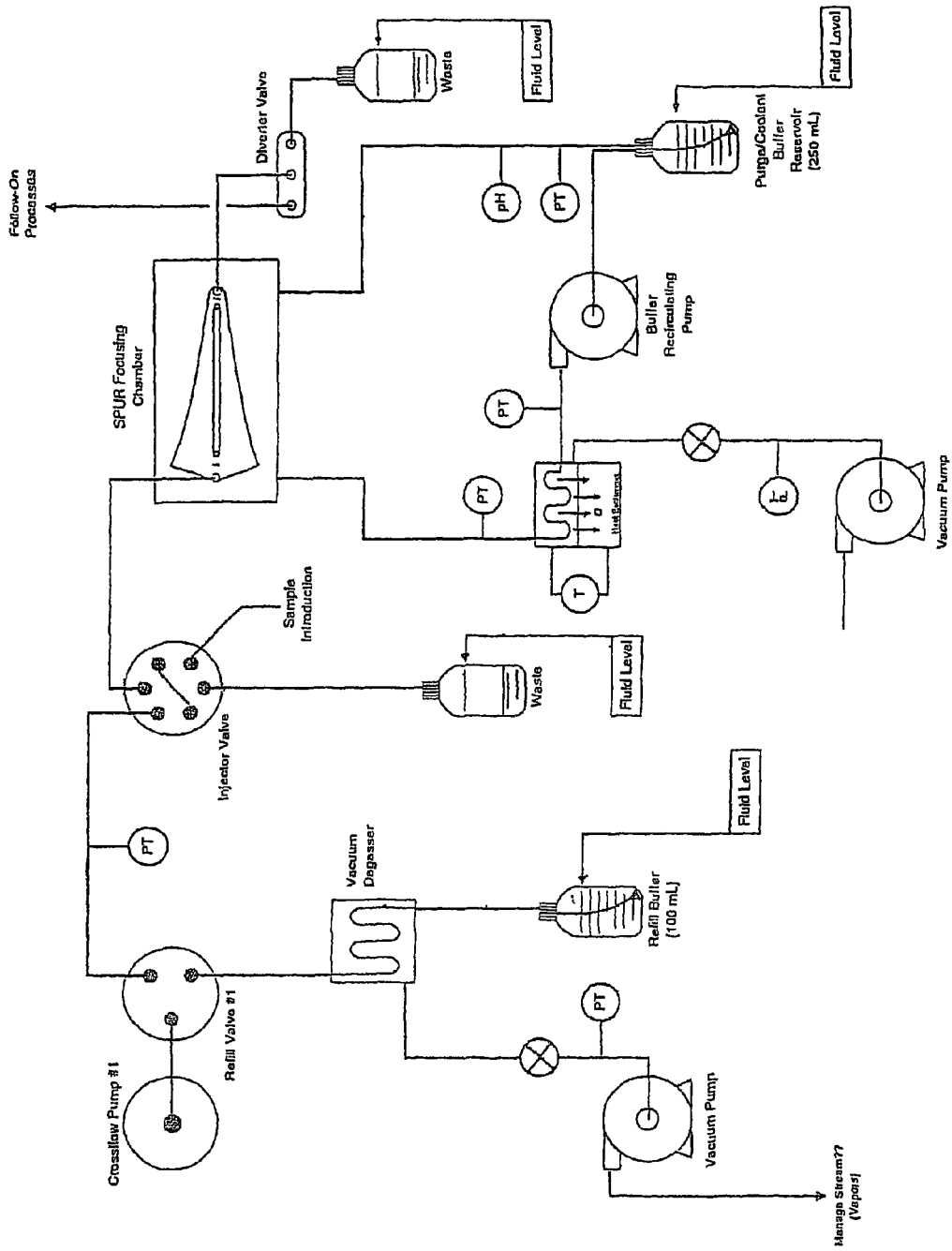
FIG. 17 is a schematic of an exemplary system.
Figure 18:
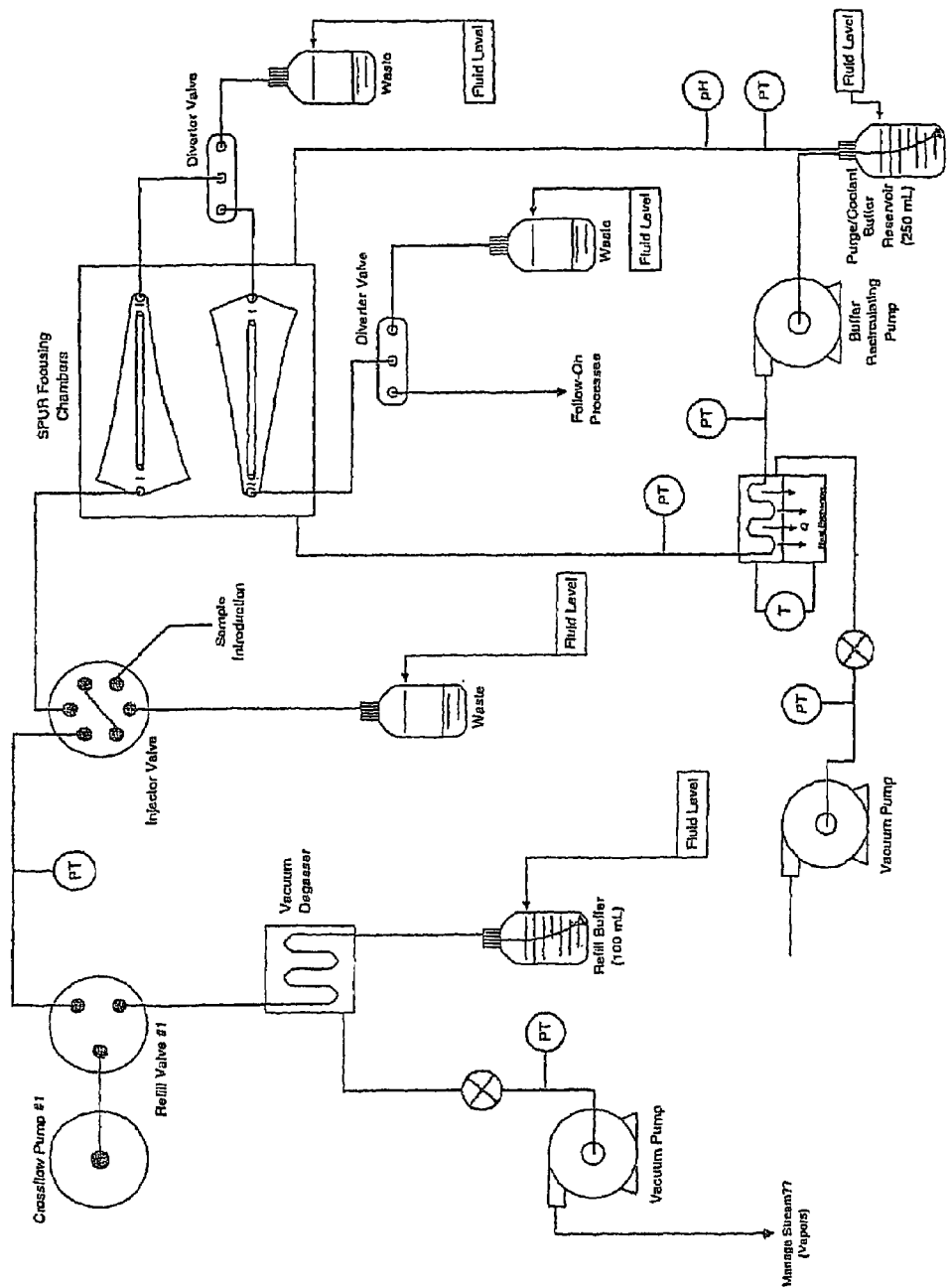
FIG. 18 is a schematic of an exemplary dual-device system.
Figure 19:
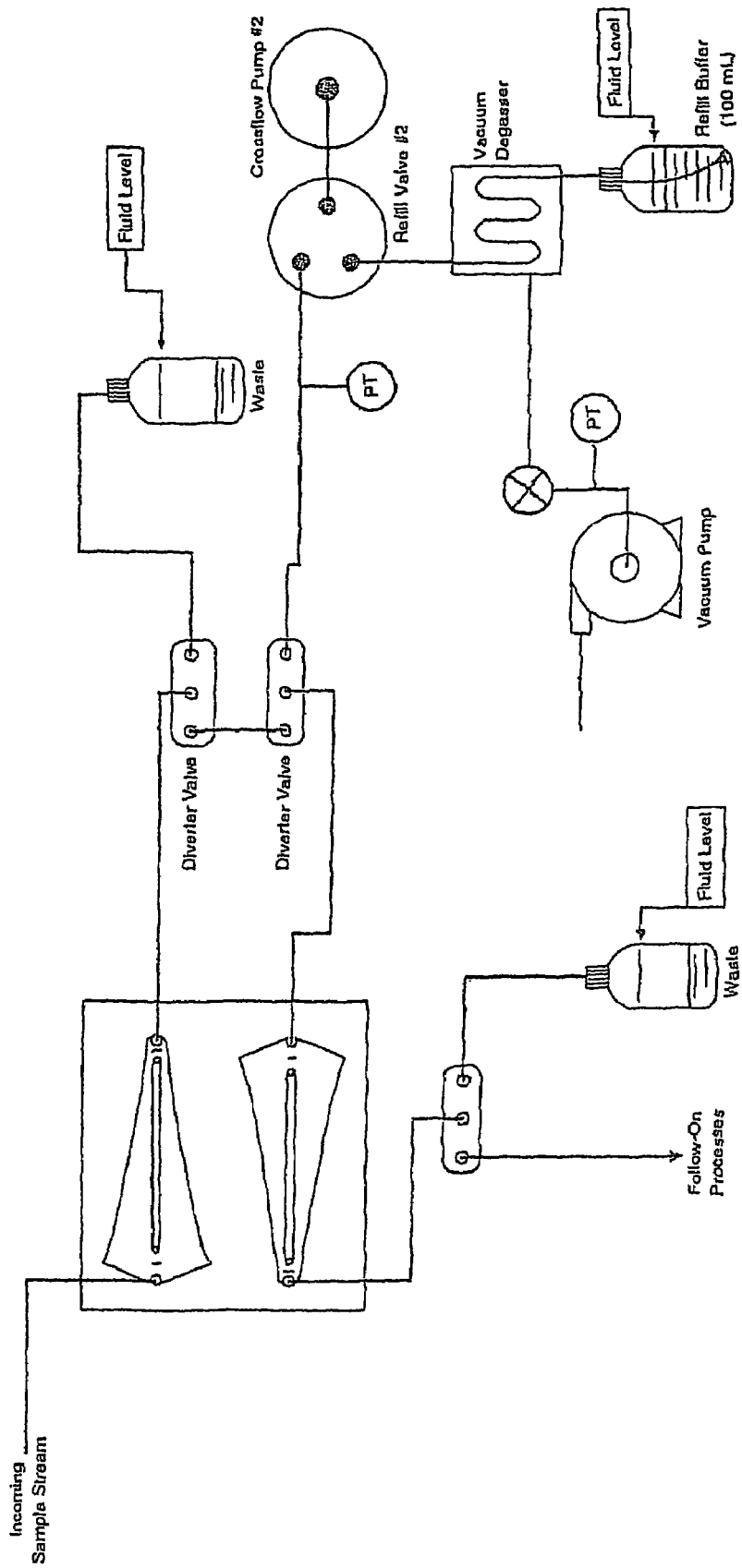
FIG. 19 is a schematic of an alternative dual-device system.

FIGS. 17, 18 and 19 are schematic illustrations showing exemplary apparatuses, with FIG. 17 representing a single electrophoretic device and FIGS. 18 and 19 representing apparatuses containing two electrophoretic devices. The devices can be controlled via RS-232, LAN, or contact closure interfaces and advantageously can be used with commercially available liquid handlers to allow unattended analyte preconcentration. Fluidic samples, for example, aqueous-phase samples, are injected into the first analytical or separation chamber with the trapping electric field turned on, and the sample is allowed to separate and focus into one or more bands of focused analyte. The electric field is then lowered to allow a low mobility band of analyte to exit or be eluted from the chamber. The eluted band can then pass to a follow-on process or processes as exemplified in FIG. 17, or into the second electrophoretic chamber via a diverter valve as exemplified in FIGS. 18 and 19. As described above, bands can be located within either chamber by separately manipulating the strength of the electric field in each chamber. Such a design is advantageous in that it permits the removal of bands of intermediate mobility while allowing the apparatus to retain bands of higher and lower mobility in the electrophoretic chambers. For example, desired bands of low mobility can be eluted from the first chamber and permitted to flow into the second chamber and then to a follow-on process or processes as desired. Typical operating parameters of an apparatus of this type with a 1-inch chamber are as described in Table 1 above. Advantageously, the dual-chamber apparatus further comprises a second crossflow pump, such as that found in the apparatus of FIG. 19, to provide flow through the second (downstream) electrophoretic device while the diverter valve separating the first (upstream) device from the second device is open to waste. The apparatus illustrated in FIG. 19 further provides for parallel operation of the pair of electrophoretic chambers, such that a sample can be split previous to injection and injected simultaneously onto each of the electrophoretic devices by appropriate manipulation of the pair of diverter valves. A second sample introduction site, for example, located downstream of refill valve #2, would permit the introduction of sample onto the second electrophoresis device, while an additional diverter valve located between the first diverter valve following the first device and the waste would allow diversion of desired bands to follow-on processes in a fashion similar to that found after the electrophoretic chamber of the single-chamber apparatus of FIG. 17. Further, such a configuration would allow the simultaneous treatment of two different samples, which need not be related. Such would effectively double the output of the apparatus by effectively allowing it to function as two distinct apparatuses. Other suitable configurations will be readily apparent to those of skill in the art, given the benefit of this disclosure.

As exemplified in FIGS. 17 and 18, certain preferred embodiments utilize a buffer recirculating pump, a vacuum pump and a heat exchanger to circulate buffer through the electrode chambers of each electrophoretic device. In this way, the buffer serves to transmit the electric field gradient to the separation chambers and to remove heat and gas generated by the electrodes. The actual connections to the electrode chambers are omitted for clarity purposes. Such a configuration would also typically be present in the apparatus illustrated in FIG. 19, and is omitted from FIG. 19 for clarity purposes. Other suitable electrode chamber fluid handling systems will be readily apparent to those skilled in the art, given the benefit of this disclosure.

In each of FIGS. 17, 18 and 19, sample is introduced via an injector valve. The samples may be directly injected, or in certain preferred embodiments may be brought into the injector valve directly or indirectly from the output of a preceding instrument, such as, for example, and HPLC instrument. In this fashion, the apparatus can be used to link up separate instruments in a hyphenated fashion, whereby the sample flows directly from one instrument into the apparatus and then into the follow-on instrument. Other suitable injection devices, for example, sample loops, etc., will be readily apparent to those skilled in the art given the benefit of the present disclosure.

Additional sample injections may be used in certain preferred embodiments to accumulate or concentrate low abundance materials while holding previous samples in either the first or, where one is present, the second chamber. Alternatively, continuous flow of sample may be so used, or a combination of continuous flow and additional injections. Further, additional such electrophoretic devices may be used in serial or in parallel networks to provide additional separation flexibility for accumulating multiple analytes for collection or analysis. Additional peripherals may be added for a specific test. Other suitable apparatus designs will be readily apparent to those of skill in the art, given the benefit of this disclosure.

Figure 23:
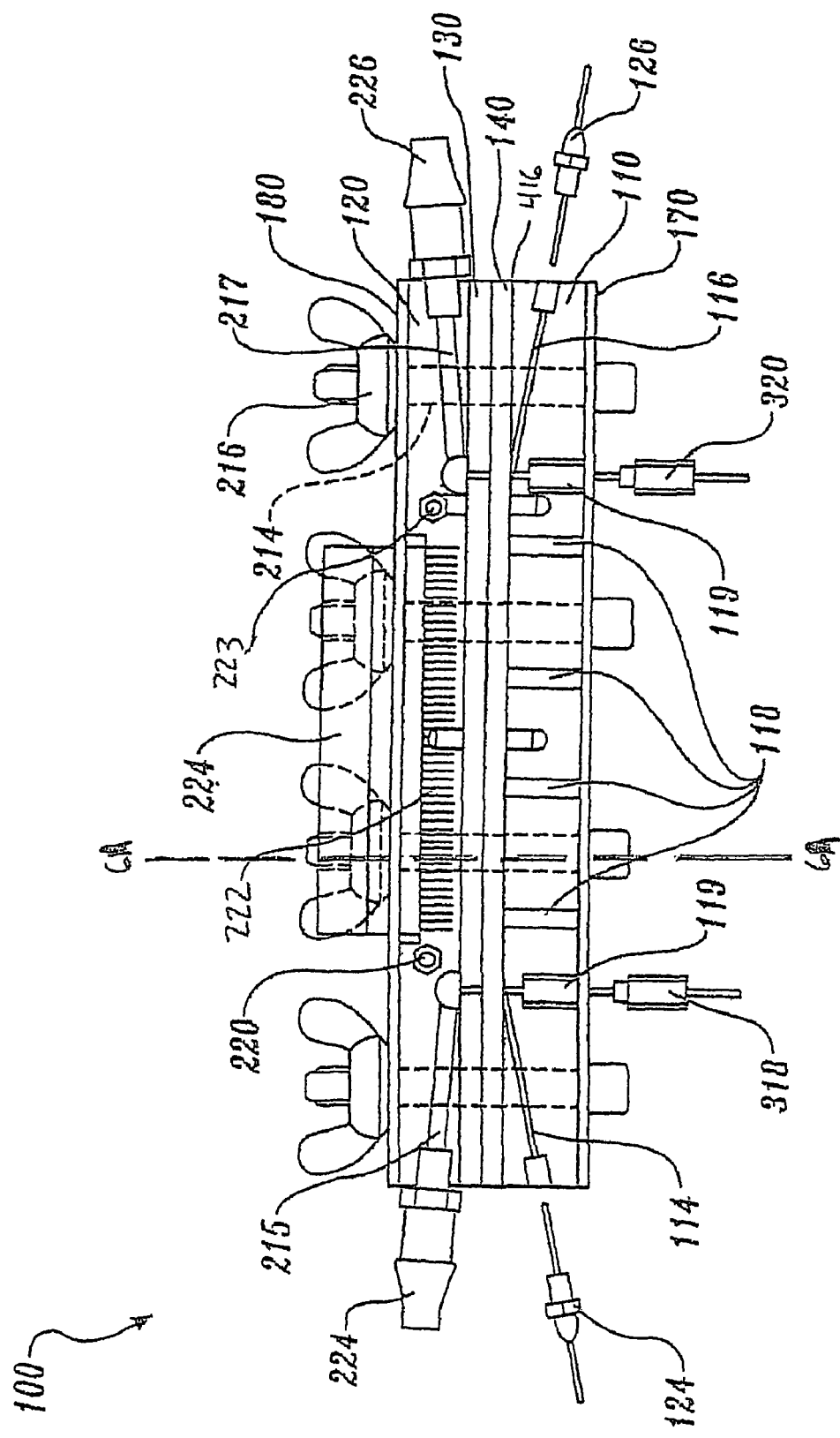
FIG. 23 is an elevation view, partly in section, of the device of FIGS. 22A-22E in assembly.
Figures 24A, 24B:
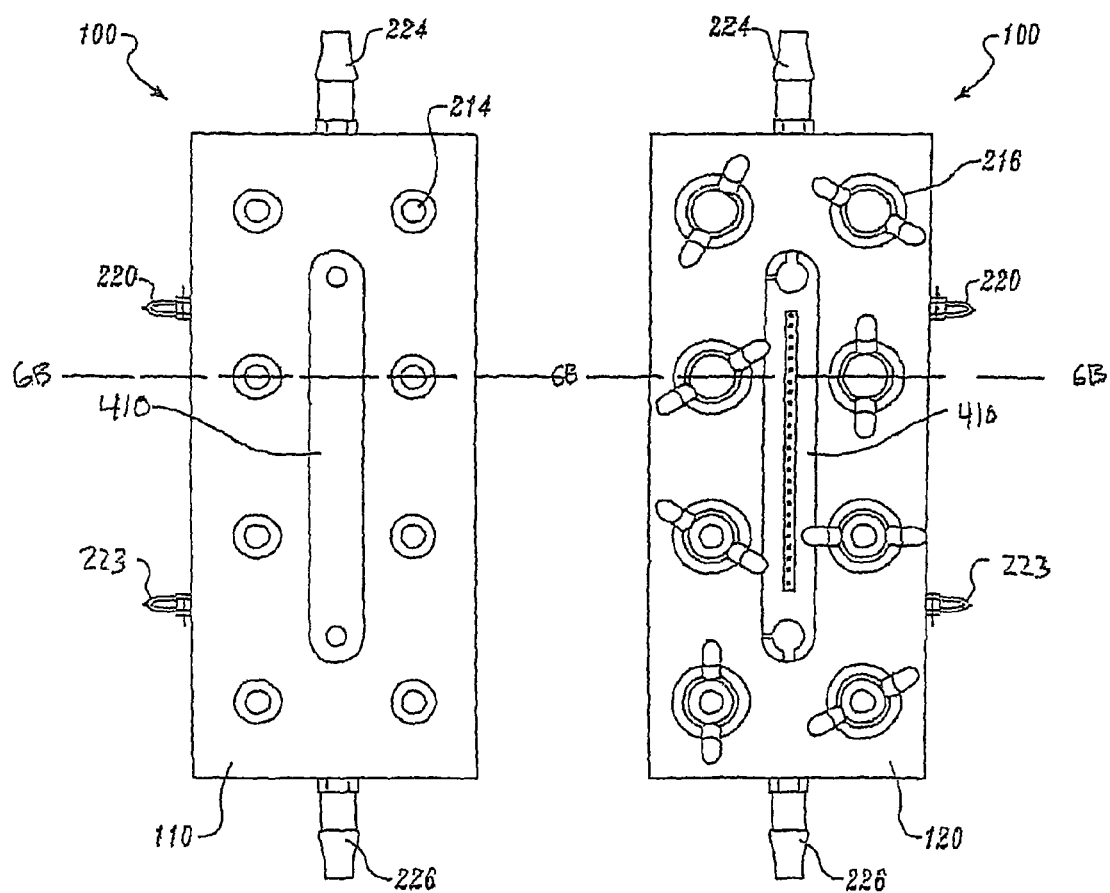
FIGS. 24A and 24B are front and back plan views, respectively, of the device of FIGS. 22A-22E and 23 in assembly.

A representative electrophoretic device including a focusing chamber as described above is shown in FIGS. 23-25. An elevation view of the device is shown in FIG. 23, and forward and rear plan views of the device as illustrated in FIGS. 24A and 24B, respectively. A cross-sectional view of a portion of a representative device illustrating the separation chamber, permeable membrane, and electrode chamber is shown in FIG. 25.

Figure 25A:
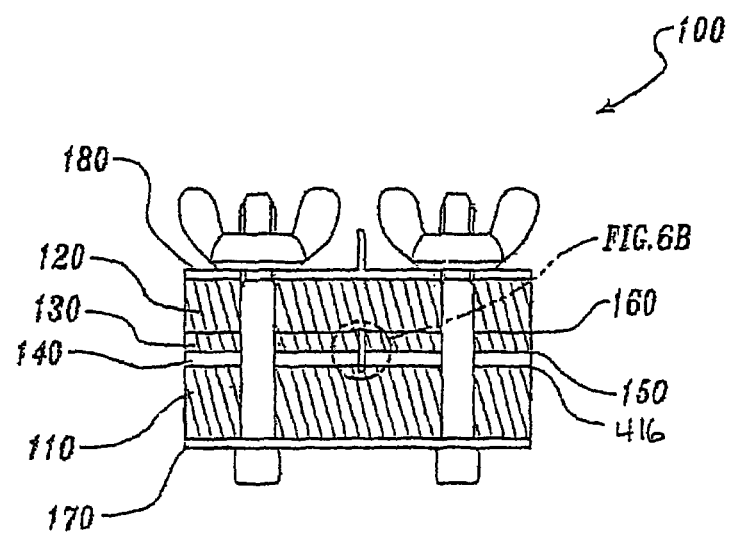
FIGS. 25A and 25B are views, partially in section, of the device of FIGS. 22A-22E, 23 and 24A-24B, in assembly, taken through line 6A-6A in FIG. 23 and line 6B-6B in FIGS. 24A and 24B, respectively.
Figure 25B:
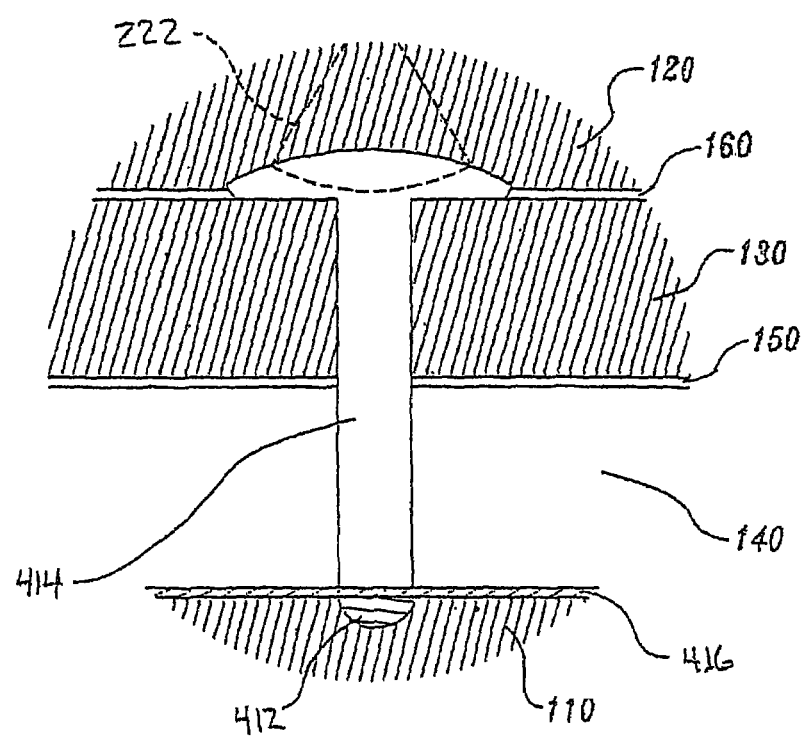
Figure 26A:
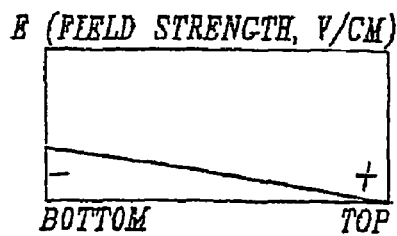
FIGS. 26A-26F present schematic representations and graphical representations of two approaches for conducting electric field gradient focusing in accordance with certain embodiments of the devices and methods disclosed here.
Figure 26B:
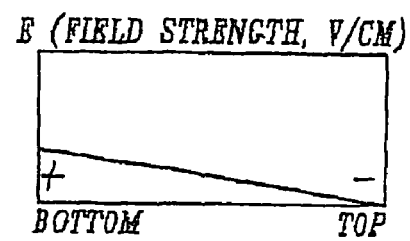
Figure 26C:
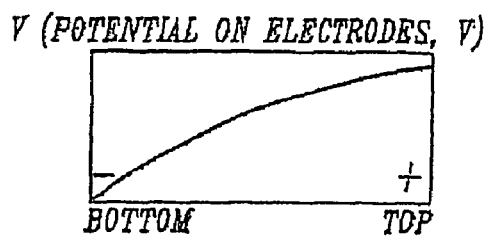
Figure 26D:
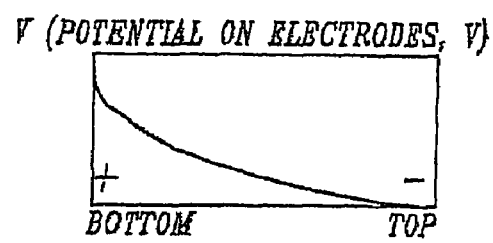
Figure 26E:
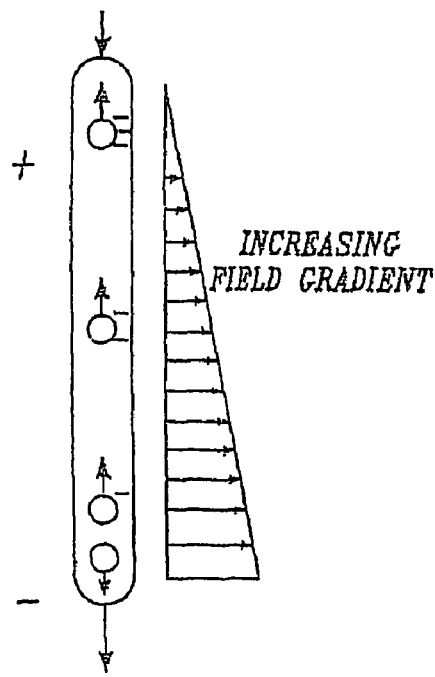
Figure 26F:
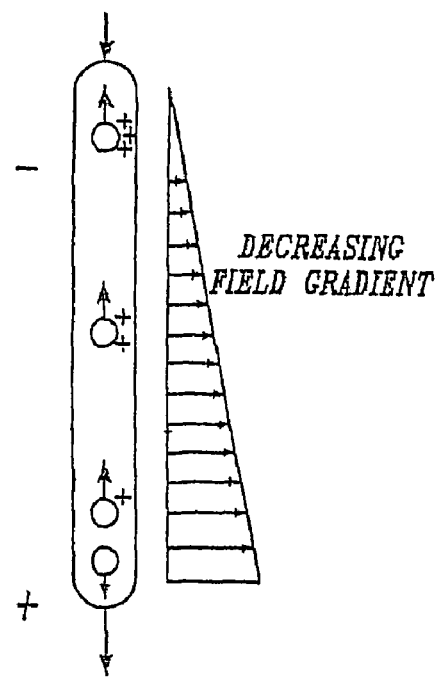

Referring to FIG. 23, device 100 includes blocks 110 and 120 and sheets 130 and 140, and permeable member 16. Conduits 114, 116, 215, and 217, noted above, are illustrated along with connecting devices 124, 126, 224, and 226, respectively, which serve to connect the focusing chamber with its respective supplies. Inlet connection device 318 and outlet connecting device 320 are illustrated and communicate with channels 119 and separation chamber inlet 418 and outlet 420, respectively. Connector 224 leads to the device's controller and provides current to the electrode array. The representative device further includes first and second plates 170 and 180, respectively, which overlie the outward surfaces of blocks 110 and 120, respectively. Plates 170 and 180 can reinforce the assembly. Plates 170 and 180 are preferably steel plates. FIGS. 25A and 25B are cross-sectional views of a portion of the representative device described above, taken through line 6A-6A in FIG. 23 and through line 6B-6B in FIG. 24. Referring to FIG. 25B, device 100 includes blocks 110 and 120 and sheets 130 and 140. Intermediate block 110 and sheet 140 is permeable membrane 416 which divides the focusing chamber into separation chamber 412 and electrode chamber 414. Sheet 140 serves as a spacer for adjusting the depth of electrode chamber 414 and, accordingly, the thickness of sheet 140 can be varied as desired. Sheet 140 is a resilient sheet and also serves to seal block 110 to the remaining components of the assembly.

Intermediate sheet 140 and sheet 130 is sealant layer 150. Sealant layer 150 includes a sealant that effectively joins sheet 140 to sheet 130 and prevents liquid from escaping the electrode chamber. Intermediate block 120 and sheet 130 is adhesive layer 160. Adhesive layer 160 includes an adhesive that effectively joins sheet 130 to block 120.

While various preferred embodiments of the methods and devices have been illustrated and described, it will be appreciated that various modifications and additions can be made to such embodiments without departing from the spirit and scope of the methods and devices as defined by the following claims.

What is claimed is:

1. An electrophoretic device comprising:
   a separation chamber having a fluid inlet port and a fluid outlet port, with a flow path from the fluid inlet port to the fluid outlet port defining a fluid flow direction through the separation chamber, and
   electrodes positioned in an electrode chamber and operative when energized to generate an electric field gradient in the separation chamber,
   wherein the separation chamber has a non-uniform configuration along at least a portion of the flow path.

2. The electrophoretic device of claim 1, wherein the separation chamber has a non-uniform width and a non-uniform height.

3. The electrophoretic device of claim 1, wherein the separation chamber comprises walls of substantially hyperbolic shape in the axial direction.

4. The electrophoretic device of claim 1, further comprising the electrode chamber separated from the separation chamber by a permeable membrane, the electrodes being positioned in the electrode chamber.

5. The electrophoretic device of claim 4, wherein the electrode chamber has a non-uniform cross-section flow channel.

6. The electrophoretic device of claim 4, wherein the electrode chamber is defined by one or more non-linear walls.

7. The electrophoretic device of claim 6, wherein the one or more non-linear walls of the electrode chamber are curved in the direction of flow along the flow path.

8. The electrophoretic device of claim 1, further comprising molecular sieve in the separation chamber operative to shift the location at which a stationary focused band of charged analyte forms under a given set of focusing process parameters.

9. The electrophoretic device of claim 8, wherein the molecular sieve comprises a gel.

10. The electrophoretic device of claim 8, wherein the molecular sieve comprises zeolites.

11. The electrophoresis device of claim 1, wherein the electrodes comprise an electrode array.

12. A method for focusing a analyte comprising:
    providing a device for focusing a charged analyte comprising:
      a non-uniform separation chamber having a fluid inlet port and a fluid outlet port;
      with a flow path from the fluid inlet port to the fluid outlet port defining a fluid flow direction through the separation chamber; and
      electrodes separated from the separation chamber and operative when energized to generate an electric field gradient in the separation chamber, wherein the electrodes comprise an electrode array;
    introducing a fluid comprising at least one analyte into the separation chamber via the inlet port; and
    energizing the electrodes to establish an electric field gradient in the separation chamber to focus at least a portion of the analyte at a location along the flow path.

13. The method of claim 12, wherein the electric field gradient is changed during the course of focusing the charged analyte.

14. The method of claim 12, wherein the charged analyte comprises an uncharged material sorbed into a charged carrier.

15. The method of claim 12, wherein the separation chamber contains molecular sieve operative to shift the location at which a stationary focused band of a charged analyte forms under a given set of focusing process parameters.

16. The method of claim 12, wherein the charged analyte comprises DNA.

17. The method of claim 12, wherein the charged analyte comprises protein.

18. The method of claim 12, wherein additional fluid comprising charged analyte is introduced into the separation chamber and focused.

19. The method of claim 12, wherein the electric field gradient is dynamically controlled.

20. An electrophoretic device comprising:
- a separation chamber having a fluid inlet port and a fluid outlet port, with a flow path from the fluid inlet port to the fluid outlet port defining a fluid flow direction through the separation chamber, and
- electrodes positioned in an electrode chamber and operative when energized to generate an electric field gradient in the separation chamber,
- wherein the separation chamber has a non-uniform configuration along at least a portion of the flow path; and
- further comprising molecular sieve in the separation chamber operative to shift the location at which a stationary focused band of charged analyte forms under a given set of focusing process parameters;
- wherein the molecular sieve comprises zeolites.

21. An electrophoretic device comprising:
- a separation chamber having a fluid inlet port and a fluid outlet port, with a flow path from the fluid inlet port to the fluid outlet port defining a fluid flow direction through the separation chamber, and
- electrodes positioned in an electrode chamber and operative when energized to generate an electric field gradient in the separation chamber,
- wherein the separation chamber has a non-uniform configuration along at least a portion of the flow path; and
- wherein the electrodes comprise an electrode array.

* * * * *